(12) United States Patent
Budzik et al.

(10) Patent No.: US 8,288,412 B2
(45) Date of Patent: *Oct. 16, 2012

(54) COMPOUNDS WHICH HAVE ACTIVITY AT $M_1$ RECEPTOR AND THEIR USES IN MEDICINE

(75) Inventors: Brian Budzik, Collegeville, PA (US); David Gwyn Cooper, Harlow (GB); Ian Thomson Forbes, Harlow (GB); Vincenzo Garzya, Harlow (GB); Jian Jin, Collegeville, PA (US); Dongchuan Shi, Collegeville, PA (US); Paul William Smith, Harlow (GB); Graham Walker, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 1176 days.

This patent is subject to a terminal disclaimer.

(21) Appl. No.: 12/088,451

(22) PCT Filed: Sep. 27, 2006

(86) PCT No.: PCT/GB2006/003595
§ 371 (c)(1),
(2), (4) Date: Mar. 28, 2008

(87) PCT Pub. No.: WO2007/036718
PCT Pub. Date: Apr. 5, 2007

(65) Prior Publication Data
US 2008/0293770 A1    Nov. 27, 2008

(30) Foreign Application Priority Data

Sep. 30, 2005  (GB) .................. 0519949.2
Feb. 13, 2006  (GB) .................. 0602856.7

(51) Int. Cl.
*A61K 31/454* (2006.01)
*C07D 405/04* (2006.01)

(52) U.S. Cl. .................. 514/322; 546/199
(58) Field of Classification Search .......... 514/322; 546/199
See application file for complete search history.

(56) References Cited

U.S. PATENT DOCUMENTS

| | | | |
|---|---|---|---|
| 3,161,645 A | 12/1964 | Janssen | |
| 3,989,707 A * | 11/1976 | Janssen et al. | 546/199 |
| 4,292,321 A | 9/1981 | Pattison | |
| 4,470,989 A * | 9/1984 | Henning et al. | 514/322 |
| 5,574,044 A | 11/1996 | Thompson et al. | |
| 5,691,323 A * | 11/1997 | Thompson et al. | 514/94 |
| 5,718,912 A | 2/1998 | Thomspon et al. | |
| 5,977,134 A | 11/1999 | Ciccarone et al. | |
| 6,162,804 A | 12/2000 | Bilodeau et al. | |
| 6,465,484 B1 | 10/2002 | Bilodeau et al. | |
| 6,872,733 B2 | 3/2005 | Goehring et al. | |
| 6,951,849 B2 | 10/2005 | Kelly et al. | |
| 7,087,593 B2 | 8/2006 | Kelly et al. | |
| 7,598,393 B2 | 10/2009 | Kon-I et al. | |
| 7,776,885 B2 | 8/2010 | Katsu et al. | |
| 2002/0019395 A1 | 2/2002 | Zhu et al. | |
| 2003/0008886 A1 | 1/2003 | Goehring et al. | |
| 2003/0040513 A1 | 2/2003 | Baxter et al. | |
| 2003/0100545 A1 | 5/2003 | Kelly et al. | |
| 2003/0171360 A1 | 9/2003 | Gross et al. | |
| 2004/0067931 A1 | 4/2004 | Kelly et al. | |
| 2005/0020575 A1 | 1/2005 | Cole et al. | |
| 2005/0192307 A1 | 9/2005 | Goehring et al. | |
| 2006/0025402 A1 | 2/2006 | Kelly et al. | |

(Continued)

FOREIGN PATENT DOCUMENTS

EP        0068261 A1     1/1983

(Continued)

OTHER PUBLICATIONS

Sur et al. "Seletive targting of Muscarinic . . . " Current Neuropharm. v. 3 p. 63-71 (2005).*

(Continued)

*Primary Examiner* — Celia Chang
(74) *Attorney, Agent, or Firm* — Linda E. Hall; John L. Lemanowicz

(57) ABSTRACT

Compounds of formula (I) and salts are provided:

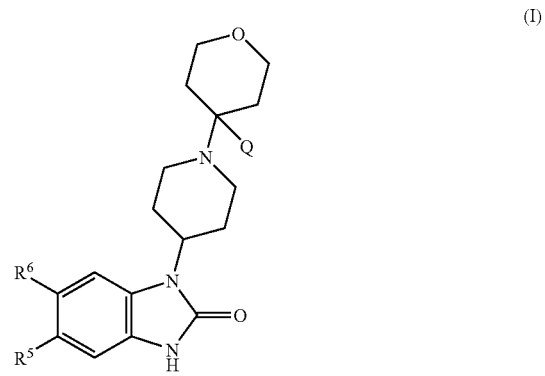

(I)

wherein $R^5$ is selected from halogen, $C_{1-6}$alkyl, $C_{1-6}$alkyl substituted with one or more fluorine atoms, $C_{1-6}$ alkoxy, $C_{1-6}$ alkoxy substituted with one or more fluorine atoms, and cyano; $R^6$ is selected from halogen, $C_{1-6}$alkyl, $C_{1-6}$alkyl substituted with one or more fluorine atoms, $C_{3-6}$cycloalkyl, $C_{3-6}$cycloalkyl substituted with one or more fluorine atoms, $C_{1-6}$ alkoxy, $C_{1-6}$ alkoxy substituted with one or more fluorine atoms, and cyano; and Q is hydrogen or $C_{1-6}$alkyl. The compounds are $M_1$ agonists and are useful for therapy, for example in the treatment of psychotic disorders and cognitive impairment.

10 Claims, No Drawings

U.S. PATENT DOCUMENTS

| | | |
|---|---|---|
| 2006/0199799 A1 | 9/2006 | Kelly et al. |
| 2006/0205785 A1 | 9/2006 | Kelly et al. |
| 2006/0258707 A1 | 11/2006 | Kelly et al. |
| 2008/0103178 A1 | 5/2008 | Hashimoto et al. |
| 2008/0255195 A1 | 10/2008 | Budzik et al. |
| 2008/0293770 A1 | 11/2008 | Budzik et al. |
| 2008/0306112 A1 | 12/2008 | Budzik et al. |

FOREIGN PATENT DOCUMENTS

| | | |
|---|---|---|
| EP | 0 491 212 A1 | 6/1992 |
| EP | 1221443 A1 | 7/2002 |
| EP | 1386920 A1 | 2/2004 |
| EP | 1491212 A | 12/2004 |
| WO | WO96/13262 A | 5/1996 |
| WO | WO97/16186 A | 5/1997 |
| WO | WO 99/32481 | 7/1999 |
| WO | WO03/105781 A | 12/2003 |
| WO | WO 2004/054974 A | 7/2004 |
| WO | WO2004/089942 | 10/2004 |
| WO | WO2007/036711 A | 4/2007 |
| WO | WO2007/036715 A | 4/2007 |
| WO | WO2007/036718 A | 4/2007 |
| WO | WO2008/119711 | 10/2008 |
| WO | WO2008/119712 | 10/2008 |
| WO | WO2008/119713 | 10/2008 |
| WO | WO2008/119714 | 10/2008 |
| WO | WO 2008/119715 | 10/2008 |
| WO | WO2008/119716 | 10/2008 |
| WO | WO2008/119717 | 10/2008 |
| WO | WO2008/119718 | 10/2008 |
| WO | WO2008/119719 | 10/2008 |
| WO | WO2008/119720 | 10/2008 |
| WO | WO2008/119721 | 10/2008 |
| WO | WO2008/0293770 | 11/2008 |

OTHER PUBLICATIONS

Jassen et al. "Benzimidazolinon . . . " CA84:135657 (1976).*

Henniung et al. "N-oxazyclyl alkylpiperidine . . . " CA98:160727 (1983).*

Burgey et al, "Benzodiazepine calcitonin gene-related peptide (CGRP) receptor antagonists: Optimization of the 4-substituted piperidine" Bioorganic & Medicinal Chemistry Letters, vol. 16, No. 19, Oct. 1, 2006 pp. 5052-5056.

Gustin D. J. et al: "Discovery and SAR studies of a novel series of noncovalent cathepsin S inhibitors" Bioorganic & Medicinal Chemistry Letters, vol. 15, No. 6, Mar. 15, 2005 pp. 1687-1691.

Hennings, R., et al: "Synthesis and neuroleptic activity of a series of 1-[1-(benzo-1,4-dioxan-2-ylmethyl)-4-piperidinyl] benzimidazolone derivatives". Journal of Medicinal Chemistry, vol. 30, No. 5, May 1987 pp. 814-819.

Poulain R., et al.: "From hit to lead. Analyzing structure-profile relationships" Journal of Medicinal Chemistry, vol. 44, Sep. 11, 2001, pp. 3391-3401.

Poulain, R., et al: "From hit to lead." Journal of Medicinal Chemistry, vol. 44 No. 21, Oct 2001, pgs. 3378-3390.

Rossi, A., et al: "Benzimidazol-Derivate and verwandte Heterocyclen V. Die Kondensation von o-Phenylendiamine mit aliphatischen and alicyclischen beta-Ketoestern" Helvetica Chimica Acta, vol. 43, No. 5, Aug. 1, 1960, pp. 1298-1313.

\* cited by examiner

COMPOUNDS WHICH HAVE ACTIVITY AT M₁ RECEPTOR AND THEIR USES IN MEDICINE

This invention relates to novel compounds, pharmaceutical compositions containing them and their use in therapy, in particular as antipsychotic agents.

Muscarinic acetylcholine receptors are members of the G protein coupled receptor superfamily which mediate the actions of the neurotransmitter acetylcholine in both the central and peripheral nervous system. Five muscarinic receptor subtypes have been cloned, $M_1$ to $M_5$. The muscarinic $M_1$ receptor is predominantly expressed in the cerebral cortex and hippocampus, although it is also expressed in the periphery e.g. exocrine glands.

Muscarinic receptors in the central nervous system, especially $M_1$, play a critical role in mediating higher cognitive processing. Diseases associated with cognitive impairments, such as Alzheimer's disease, are accompanied by loss of cholinergic neurons in the basal forebrain. Furthermore, in animal models, blockade or lesion of central cholinergic pathways results in profound cognitive deficits.

Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to side effects resulting from stimulation of peripheral muscarinic receptors including disturbed gastrointestinal motility and nausea.

The dopamine hypothesis of schizophrenia suggests that excess dopaminergic stimulation is responsible for the positive symptoms of the disease, hence the utility of dopamine receptor antagonists to reduce psychotic symptoms. However, conventional dopamine receptor antagonists can cause extrapyramidal side effects (EPS) in patients, including tremor and tardive dyskinesias.

$M_1$ receptor agonists have been sought for the symptomatic treatment of cognitive decline. More recently, a number of groups have shown that muscarinic receptor agonists display an atypical antipsychotic-like profile in a range of pre-clinical paradigms. The muscarinic agonist, xanomeline, reverses a number of dopamine driven behaviours, including amphetamine induced locomotion in rats, apomorphine induced climbing in mice, dopamine agonist driven turning in unilateral 6-OH-DA lesioned rats and amphetamine-induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile.

Xanomeline has also been shown to reduce psychotic symptoms such as suspiciousness, hallucinations and delusions in Alzheimer's patients. However, the relatively non-selective nature of the compound gives rise to dose-limiting peripheral cholinergic side effects.

Selective $M_1$ receptor agonists have the potential utility to ameliorate positive and cognitive symptoms of psychotic disorders such as schizophrenia, schizo-affective disorders, schizophreniform diseases, psychotic depression, mania, acute mania, paranoid and delusional disorders, and cognitive impairment including memory disorders such as Alzheimer's disease without peripheral cholinergic side effects mediated predominantly through $M_2$ and $M_3$ receptors.

$M_1$ receptor agonists may also be suitable for combination with other typical and atypical antipsychotics and other actives such as mood stabilisers, antidepressants, anxiolytics, drugs for extrapyrimidal side effects and cognitive enhancers, to provide improved treatment of psychotic disorders.

We have now found a novel group of compounds which are useful for the treatment of psychotic disorders.

In a first aspect therefore, the invention provides a compound of formula (I) or a salt or solvate thereof:

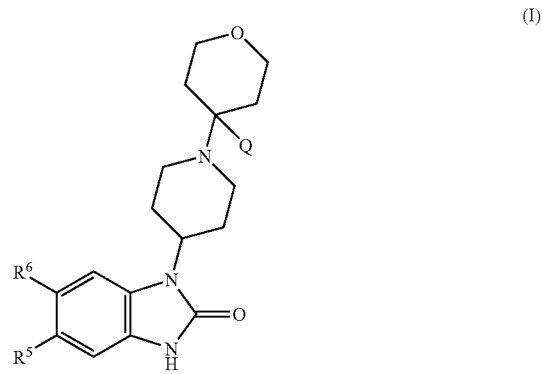

(I)

wherein:
  $R^5$ is selected from halogen, $C_{1-6}$alkyl, $C_{1-6}$alkyl substituted with one or more fluorine atoms, $C_{1-6}$ alkoxy, $C_{1-6}$ alkoxy substituted with one or more fluorine atoms, and cyano;
  $R^6$ is selected from halogen, $C_{1-6}$alkyl, $C_{1-6}$alkyl substituted with one or more fluorine atoms, $C_{3-6}$cycloalkyl, $C_{3-6}$cycloalkyl substituted with one or more fluorine atoms, $C_{1-6}$ alkoxy, $C_{1-6}$ alkoxy substituted with one or more fluorine atoms, and cyano; and
  Q is hydrogen or $C_{1-6}$alkyl.

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. $C_{1-3}$alkyl means a straight or branched alkyl containing at least 1, and at most 3, carbon atoms. Examples of "alkyl" as used herein include, but are not limited to, methyl, ethyl, n-propyl, n-butyl, n-pentyl, n-hexyl, isobutyl, isopropyl, t-butyl and 1,1-dimethylpropyl.

As used herein, the term "alkoxy" refers to a straight or branched alkoxy group containing the specified number of carbon atoms. For example, $C_{1-6}$alkoxy means a straight or branched alkoxy group containing at least 1, and at most 6, carbon atoms. Examples of "alkoxy" as used herein include, but are not limited to, methoxy, ethoxy, propoxy, prop-2-oxy, butoxy, but-2-oxy, 1-methylethyl-oxy, 2-methylprop-1-oxy, 2-methylprop-2-oxy, pentoxy or hexyloxy.

As used herein, the term "cycloalkyl" refers to a non-aromatic hydrocarbon ring containing the specified number of carbon atoms. For example, $C_{3-6}$cycloalkyl means a non-aromatic ring containing at least three, and at most six, ring carbon atoms. Examples of "cycloalkyl" as used herein include, but are not limited to, cyclopropyl, cyclobutyl, cyclopentyl and cyclohexyl.

As used herein, the term "halogen" (or the abbreviated form "halo") refers to the elements fluorine (which may be abbreviated to "fluoro"), chlorine (which may be abbreviated to "chloro"), bromine (which may be abbreviated to "bromo") and iodine (which may be abbreviated to "iodo"). Examples of halogens are fluorine, chlorine and bromine.

As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. The solvent used may be water and the solvate may also be referred to as a hydrate.

As used herein, the term "substituted" refers to substitution with the named substituent or substituents, multiple degrees of substitution being allowed unless otherwise stated. For example, there may be 1, 2, 3 or 4 substituents on a given substituted group. For example, if $R^6$ is a $C_{1-6}$alkyl group, it may be substituted by 1, 2, 3 or 4 fluoro groups; and if $R^6$ is a $C_{1-6}$alkoxy group, it may be substituted by 1, 2, 3 or 4 fluoro groups. For example, $R^6$ may be a $C_{1-6}$alkyl group substituted by 3 fluoro groups; and $R^6$ may be a $C_{1-6}$alkoxy group substituted by 3 fluoro groups. For example, $R^6$ may be $CF_3$. Similarly, if $R^5$ is a $C_{1-6}$alkyl group substituted by one or more fluoro groups, it may be substituted by 1, 2, 3 or 4 fluoro groups; and if $R^5$ is a $C_{1-6}$alkoxy group, it may be substituted by 1, 2, 3 or 4 fluoro groups. For example, $R^5$ may be a $C_{1-6}$alkyl group substituted by 3 fluoro groups; and $R^5$ may be a $C_{1-6}$alkoxy group substituted by 3 fluoro groups. For example, $R^5$ may be $CF_3$ or $CH_2F$.

In one embodiment, $R^5$ is selected from halogen, $C_{1-6}$alkyl, $C_{1-6}$alkyl substituted with one, two or three fluorine atoms, $C_{1-6}$alkoxy, $C_{1-6}$alkoxy substituted with one, two or three fluorine atoms, and cyano.

In one embodiment of the invention, $R^5$ is selected from halogen, $C_{1-4}$alkyl, $C_{1-4}$alkyl substituted with one or more fluorine atoms, $C_{1-4}$alkoxy, $C_{1-4}$alkoxy substituted with one or more fluorine atoms, and cyano.

In one embodiment of the invention, $R^5$ is selected from halogen, $C_{1-4}$alkyl, $C_{1-4}$alkyl substituted with one, two or three fluorine atoms, $C_{1-4}$alkoxy, $C_{1-4}$alkoxy substituted with one, two or three fluorine atoms, and cyano.

In one embodiment of the invention, $R^5$ is selected from fluoro, chloro, bromo, methyl, methoxy, methylethyloxy, cyano, difluoromethyl and trifluoromethyl.

In one embodiment of the invention, $R^5$ is selected from chloro, bromo, fluoro, $C_{1-4}$alkyl, $C_{1-4}$alkyl substituted with one or more fluorine atoms, and $C_{1-4}$alkoxy.

In one embodiment of the invention, $R^5$ is selected from chloro, bromo, fluoro, $C_{1-4}$alkyl, $C_{1-4}$alkyl substituted with one, two or three fluorine atoms, and $C_{1-4}$alkoxy.

In a further embodiment of the invention, $R^5$ is selected from chloro, bromo, fluoro, methyl, ethyl, methoxy and trifluoromethyl. In one embodiment, $R^5$ is selected from chloro, bromo and methyl.

In one embodiment of the invention, $R^6$ is selected from chloro, bromo, fluoro, $C_{1-4}$alkyl, $C_{1-4}$alkyl substituted with one or more fluorine atoms, $C_{3-6}$cycloalkyl, $C_{1-4}$alkoxy, and $C_{1-4}$alkoxy substituted with one or more fluorine atoms.

In another embodiment of the invention, $R^6$ is selected from chloro, bromo, fluoro, $C_{1-4}$alkyl, $C_{1-4}$alkyl substituted with one, two or three fluorine atoms, $C_{3-6}$cycloalkyl, $C_{1-4}$alkoxy, and $C_{1-4}$alkoxy substituted with one, two or three fluorine atoms.

In one embodiment of the invention, $R^6$ is selected from chloro, bromo, fluoro, $C_{1-4}$alkyl, $C_{1-4}$alkyl substituted with one or more fluorine atoms, $C_{1-4}$alkoxy, and $C_{1-4}$alkoxy, substituted with one or more fluorine atoms.

In one embodiment of the invention, $R^6$ is selected from chloro, bromo, fluoro, $C_{1-4}$alkyl, $C_{1-4}$alkyl substituted with one, two or three fluorine atoms, $C_{1-4}$alkoxy, and $C_{1-4}$alkoxy substituted with one, two or three fluorine atoms.

In one embodiment of the invention, $R^6$ is selected from chloro, bromo, fluoro, methyl, ethyl, isopropyl, cyclopropyl, methoxy, methylethyloxy, trifluoromethoxy and trifluoromethyl. For example, $R^6$ is selected from chloro, fluoro and methyl.

In an embodiment of the invention $R^6$ is selected from chloro, bromo, fluoro, methyl, ethyl, isopropyl, methoxy, trifluoromethoxy and trifluoromethyl. In one embodiment, $R^6$ is selected from chloro, fluoro and methyl.

In an embodiment of the invention, $R^5$ is selected from fluoro, methyl or chloro and $R^6$ is methyl.

In an embodiment of the invention, Q is selected from hydrogen and $C_{1-3}$alkyl. In a further embodiment, Q is selected from hydrogen, methyl, ethyl and propyl. In one embodiment, Q represents hydrogen or methyl. In one embodiment, Q is hydrogen.

The present invention also provides a compound of formula (Ia):

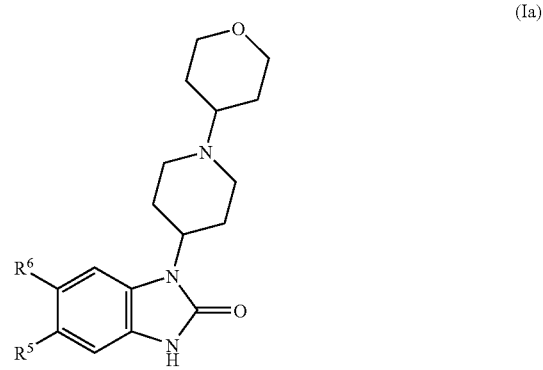

(Ia)

wherein:
  $R^5$ is selected from halogen, $C_{1-6}$alkyl, $C_{1-6}$alkyl substituted with one or more fluorine atoms, $C_{1-6}$ alkoxy, and $C_{1-6}$ alkoxy substituted with one or more fluorine atoms;
  $R^6$ is selected from halogen, $C_{1-6}$alkyl, $C_{1-6}$alkyl substituted with one or more fluorine atoms, $C_{3-6}$cycloalkyl, $C_{3-6}$cycloalkyl substituted with one or more fluorine atoms, $C_{1-6}$ alkoxy, and $C_{1-6}$ alkoxy substituted with one or more fluorine atoms or a pharmaceutically acceptable salt or solvate thereof.

The present invention also provides a compound of formula (Ib):

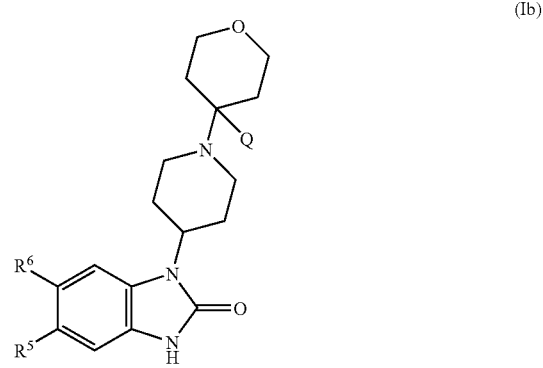

(Ib)

wherein:
  $R^5$ is selected from halogen, $C_{1-6}$alkyl, $C_{1-6}$alkyl substituted with one or more fluorine atoms, $C_{1-6}$ alkoxy, and $C_{1-6}$ alkoxy substituted with one or more fluorine atoms;

R⁶ is selected from halogen, $C_{1-6}$alkyl, $C_{1-6}$alkyl substituted with one or more fluorine atoms, $C_{3-6}$cycloalkyl, $C_{3-6}$cycloalkyl substituted with one or more fluorine atoms, $C_{1-6}$ alkoxy, and $C_{1-6}$ alkoxy substituted with one or more fluorine atoms; and Q is hydrogen or $C_{1-6}$alkyl;

or a pharmaceutically acceptable salt or solvate thereof.

All features and embodiments for formula (I) apply to compounds of formula (Ia) and (Ib) mutatis mutandis. Hereinafter, all references to compounds of formula (I) include compounds of formula (Ia) and compounds of formula (Ib).

It will be appreciated that for use in medicine the salts of formula (I) should be pharmaceutically acceptable. Suitable salts will be apparent to those skilled in the art and include for example acid salts, for example sodium, potassium, calcium, magnesium and tetraalkylammonium and the like, or mono- or di-basic salts formed with inorganic acids e.g. hydrochloric, hydrobromic, sulfuric, nitric or sulfamic phosphoric acid; and organic acids e.g. succinic, maleic, malic, mandelic, acetic, isethionic fumaric, glutamic, lactic, citric, tartaric, benzoic, lactobionic benzenesulfonic, p-toluenesulfonic, methanesulfonic ethanesulfonic or naphthalenesulfonic acid. Examples of salts further include trifluoroacetate salts and formate salts. Other non-pharmaceutically acceptable salts e.g. oxalates, may be used, for example in the isolation of compounds of formula (I) and are included within the scope of this invention.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Certain of the compounds of formula (I) may form acid addition salts with less than one (for example, 0.5 equivalent of a dibasic acid) or one or more equivalents of an acid. The present invention includes within its scope all possible stoichiometric and non-stoichiometric forms thereof.

Certain compounds of formula (I) may exist in stereoisomeric forms (e.g. they may contain one or more asymmetric carbon atoms). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Likewise, it is understood that compounds of formula (I) may exist in tautomeric forms other than that shown in the formula and these are also included within the scope of the present invention.

The present invention includes within the scope all pharmaceutically acceptable derivatives of the compounds of formula (I). As used herein, the term "pharmaceutically acceptable derivative", means any pharmaceutically acceptable salt, solvate, or prodrug e.g. ester, of a compound of formula (I), which upon administration to the recipient is capable of providing (directly or indirectly) a compound of formula (I), or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention. Examples of suitable protecting groups for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention. Suitable prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Particular compounds according to the invention include those specifically exemplified in the Examples section and named hereinafter including, without limitation:—

6-Chloro-5-fluoro-1-[1-(tetrahydro-2H-pyran-4-yl)-4-piperidinyl]-1,3-dihydro-2H-benzimidazol-2-one 6-Chloro-5-methyl-1-[1-(tetrahydro-2H-pyran-4-yl)-4-piperidinyl]-1,3-dihydro-2H-benzimidazol-2-one 6-Chloro-1-[1-(tetrahydro-2H-pyran-4-yl)-4-piperidinyl]-5-(trifluoromethyl)-1,3-dihydro-2H-benzimidazol-2-one 6-Methyl-5-(methyloxy)-1-[1-(tetrahydro-2H-pyran-4-yl)-4-piperidinyl]-1,3-dihydro-2H-benzimidazol-2-one 5-Chloro-6-methyl-1-[1-(tetrahydro-2H-pyran-4-yl)-4-piperidinyl]-1,3-dihydro-2H-benzimidazol-2-one 5-Fluoro-6-methyl-1-[1-(tetrahydro-2H-pyran-4-yl)-4-piperidinyl]-1,3-dihydro-2H-benzimidazol-2-one 5,6-Dimethyl-1-[1-(tetrahydro-2H-pyran-4-yl)-4-piperidinyl]-1,3-dihydro-2H-benzimidazol-2-one 5-Bromo-6-methyl-1-[1-(tetrahydro-2H-pyran-4-yl)-4-piperidinyl]-1,3-dihydro-2H-benzimidazol-2-one 5,6-Dichloro-1-[1-(tetrahydro-2H-pyran-4-yl)-4-piperidinyl]-1,3-dihydro-2H-benzimidazol-2-one 5-Chloro-6-methoxy-1-[1-(tetrahydro-2H-pyran-4-yl)-4-piperidinyl]-1,3-dihydro-2H-benzimidazol-2-one 5-Fluoro-6-bromo-1-[1-(tetrahydro-2H-pyran-4-yl)-4-piperidinyl]-1,3-dihydro-2H-benzimidazol-2-one 6-Chloro-5-trifluoromethyl-1-[1-(tetrahydro-2H-pyran-4-yl)-4-piperidinyl]-1,3-dihydro-2H-benzimidazol-2-one 6-Bromo-1-[1-(tetrahydro-2H-pyran-4-yl)-4-piperidinyl]-5-(trifluoromethyl)-1,3-dihydro-2H-benzimidazol-2-one 6-Methyl-1-[1-(tetrahydro-2H-pyran-4-yl)-4-piperidinyl]-5-(trifluoromethyl)-1,3-dihydro-2H-benzimidazol-2-one 6-Chloro-1-[1-(4-methyltetrahydro-2H-pyran-4-yl)-4-piperidinyl]-5-(trifluoromethyl)-1,3-dihydro-2H-benzimidazol-2-one 6-Bromo-1-[1-(4-methyltetrahydro-2H-pyran-4-yl)-4-piperidinyl]-5-(trifluoromethyl)-1,3-dihydro-2H-benzimidazol-2-one 6-Methyl-1-[1-(4-methyltetrahydro-2H-pyran-4-yl)-4-piperidinyl]-5-(trifluoromethyl)-1,3-dihydro-2H-benzimidazol-2-one 5-Fluoro-6-methyl-1-[1-(4-methyltetrahydro-2H-pyran-4-yl)piperidin-4-yl]-1,3-dihydro-2H-benzimidazol-2-one 6-Methyl-5-[(1-methylethyl)oxy]-1-[1-(tetrahydro-2H-pyran-4-yl)-4-piperidinyl]-1,3-dihydro-2H-benzimidazol-2-one
6-Ethyl-5-fluoro-1-[1-(tetrahydro-2H-pyran-4-yl)-4-piperidinyl]-1,3-dihydro-2H-benzimidazol-2-one
6-Cyclopropyl-5-fluoro-1-[1-(tetrahydro-2H-pyran-4-yl)-4-piperidinyl]-1,3-dihydro-2H-benzimidazol-2-one
5-Chloro-6-[(1-methylethyl)oxy]-1-[1-(tetrahydro-2H-pyran-4-yl)-4-piperidinyl]-1,3-dihydro-2H-benzimidazol-2-one
5,6-Difluoro-1-[1-(tetrahydro-2H-pyran-4-yl)-4-piperidinyl]-1,3-dihydro-2H-benzimidazol-2-one
6-Methyl-2-oxo-1-[1-(tetrahydro-2H-pyran-4-yl)-4-piperidinyl]-2,3-dihydro-1H-benzimidazole-5-carbonitrile
6-Chloro-5-(difluoromethyl)-1-[1-(tetrahydro-2H-pyran-4-yl)-4-piperidinyl]-1,3-dihydro-2H-benzimidazol-2-one
5,6-Dimethyl-1-[1-(4-methyltetrahydro-2H-pyran-4-yl)-4-piperidinyl]-1,3-dihydro-2H-benzimidazol-2-one
and salts and solvates thereof, for example the hydrochloride salt, the trifluoroacetate salt or the formate salt of any of the above compounds.

Specific examples of salts of the present invention include:
6-Chloro-5-fluoro-1-[1-(tetrahydro-2H-pyran-4-yl)-4-piperidinyl]-1,3-dihydro-2H-benzimidazol-2-one hydrochloride
6-Chloro-5-methyl-1-[1-(tetrahydro-2H-pyran-4-yl)-4-piperidinyl]-1,3-dihydro-2H-benzimidazol-2-one hydrochloride
6-Chloro-1-[1-(tetrahydro-2H-pyran-4-yl)-4-piperidinyl]-5-(trifluoromethyl)-1,3-dihydro-2H-benzimidazol-2-one hydrochloride
6-Methyl-5-(methyloxy)-1-[1-(tetrahydro-2H-pyran-4-yl)-4-piperidinyl]-1,3-dihydro-2H-benzimidazol-2-one hydrochloride
5-Chloro-6-methyl-1-[1-(tetrahydro-2H-pyran-4-yl)-4-piperidinyl]-1,3-dihydro-2H-benzimidazol-2-one hydrochloride
5-Fluoro-6-methyl-1-[1-(tetrahydro-2H-pyran-4-yl)-4-piperidinyl]-1,3-dihydro-2H-benzimidazol-2-one hydrochloride
5,6-Dimethyl-1-[1-(tetrahydro-2H-pyran-4-yl)-4-piperidinyl]-1,3-dihydro-2H-benzimidazol-2-one hydrochloride
5-Bromo-6-methyl-1-[1-(tetrahydro-2H-pyran-4-yl)-4-piperidinyl]-1,3-dihydro-2H-benzimidazol-2-one hydrochloride
5,6-Dichloro-1-[1-(tetrahydro-2H-pyran-4-yl)-4-piperidinyl]-1,3-dihydro-2H-benzimidazol-2-one hydrochloride
5-Chloro-6-methoxy-1-[1-(tetrahydro-2H-pyran-4-yl)-4-piperidinyl]-1,3-dihydro-2H-benzimidazol-2-one hydrochloride
5-Fluoro-6-bromo-1-[1-(tetrahydro-2H-pyran-4-yl)-4-piperidinyl]-1,3-dihydro-2H-benzimidazol-2-one hydrochloride
6-Chloro-5-trifluoromethyl-1-[1-(tetrahydro-2H-pyran-4-yl)-4-piperidinyl]-1,3-dihydro-2H-benzimidazol-2-one hydrochloride
6-Bromo-1-[1-(tetrahydro-2H-pyran-4-yl)-4-piperidinyl]-5-(trifluoromethyl)-1,3-dihydro-2H-benzimidazol-2-one hydrochloride
6-Methyl-1-[1-(tetrahydro-2H-pyran-4-yl)-4-piperidinyl]-5-(trifluoromethyl)-1,3-dihydro-2H-benzimidazol-2-one hydrochloride
6-Chloro-1-[1-(4-methyltetrahydro-2H-pyran-4-yl)-4-piperidinyl]-5-(trifluoromethyl)-1,3-dihydro-2H-benzimidazol-2-one hydrochloride
6-Bromo-1-[1-(4-methyltetrahydro-2H-pyran-4-yl)-4-piperidinyl]-5-(trifluoromethyl)-1,3-dihydro-2H-benzimidazol-2-one hydrochloride
6-Methyl-1-[1-(4-methyltetrahydro-2H-pyran-4-yl)-4-piperidinyl]-5-(trifluoromethyl)-1,3-dihydro-2H-benzimidazol-2-one hydrochloride
5-Fluoro-6-methyl-1-[1-(4-methyltetrahydro-2H-pyran-4-yl)piperidin-4-yl]-1,3-dihydro-2H-benzimidazol-2-one hydrochloride
6-Methyl-5-[(1-methylethyl)oxy]-1-[1-(tetrahydro-2H-pyran-4-yl)-4-piperidinyl]-1,3-dihydro-2H-benzimidazol-2-one hydrochloride
6-Ethyl-5-fluoro-1-[1-(tetrahydro-2H-pyran-4-yl)-4-piperidinyl]-1,3-dihydro-2H-benzimidazol-2-one hydrochloride
6-Cyclopropyl-5-fluoro-1-[1-(tetrahydro-2H-pyran-4-yl)-4-piperidinyl]-1,3-dihydro-2H-benzimidazol-2-one hydrochloride
5-Chloro-6-[(1-methylethyl)oxy]-1-[1-(tetrahydro-2H-pyran-4-yl)-4-piperidinyl]-1,3-dihydro-2H-benzimidazol-2-one hydrochloride
5,6-Difluoro-1-[1-(tetrahydro-2H-pyran-4-yl)-4-piperidinyl]-1,3-dihydro-2H-benzimidazol-2-one hydrochloride
6-Methyl-2-oxo-1-[1-(tetrahydro-2H-pyran-4-yl)-4-piperidinyl]-2,3-dihydro-1H-benzimidazole-5-carbonitrile hydrochloride
6-Chloro-5-(difluoromethyl)-1-[1-(tetrahydro-2H-pyran-4-yl)-4-piperidinyl]-1,3-dihydro-2H-benzimidazol-2-one hydrochloride and
5,6-Dimethyl-1-[1-(4-methyltetrahydro-2H-pyran-4-yl)-4-piperidinyl]-1,3-dihydro-2H-benzimidazol-2-one hydrochloride.

In a further aspect, the invention provides a general process (A1) for preparing compounds of formula (I), in which Q=H, which process comprises:

coupling a compound of formula (II)

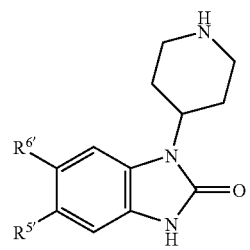

(II)

with a compound of formula (III)

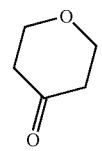

(III)

wherein
$R^{5'}$ is a group $R^5$ as previously defined, or a group convertible to $R^5$ and $R^{6'}$ is a group $R^6$ as previously defined, or a group convertible to $R^6$.

The reaction is carried out under conditions suitable for reductive alkylation. The reductive alkylation reaction is typically carried out using sodium triacetoxyborohydride in dichloroethane, optionally in the presence of triethylamine, and optionally in the presence of titanium tetraisopropoxide. Alternatively sodium cyanoborohydride can be used as the reducing reagent in solvents such as methanol or ethanol, or the reductive alkylation can be effected under catalytic hydrogenation conditions using a palladium catalyst. In a further variation, the compounds (II) and (III) can be condensed under dehydrating conditions e.g. molecular sieves or magnesium sulfate, and the resultant imine or enamine reduced using for example sodium borohydride or by catalytic hydrogenation.

A modification of general process (A1) is required where $Q=C_{1-6}$ alkyl. Thus, in general process (A2), a compound of formula (II) can be reacted with a compound of formula (III) in the presence of a source of cyanide, e.g. potassium cyanide or acetone cyanohydrin, to form the cyano intermediate (XXXX) which can be reacted with an alkyl Grignard reagent QMgX to form compounds of formula (I).

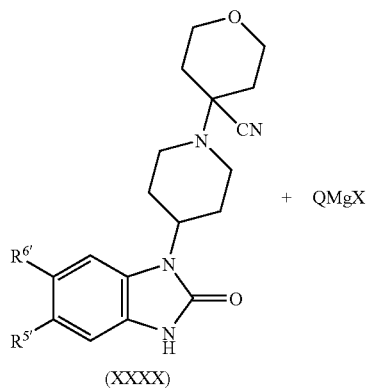

(XXXX)     + QMgX wherein
$R^{5'}$ is a group $R^5$ as previously defined, or a group convertible to $R^5$ and $R^{6'}$ is a group $R^6$ as previously defined, or a group convertible to $R^6$, Q is hydrogen or $C_{1-6}$alkyl, and X is chloro, bromo or iodo.

The reaction is carried out using conditions similar to those described in the literature (Arch Pharm (Weinheim), 1987, 320 (4), 348-361). The piperidine and ketone components are treated with potassium cyanide in water at pH3 or reacted with acetone cyanohydrin in dimethylacetamide at elevated temperature to form the adduct (XXXX). Reaction of the adduct (XXXX) with the alkyl Grignard reagent QMgX in ether or tetrahydrofuran provides compounds of formula (I).

In a further aspect, the invention provides a general process (B) for preparing compounds of formula (I) which process comprises:
coupling a compound of formula (IV)

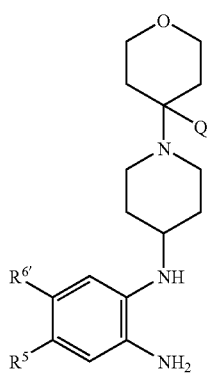

(IV)

with a compound of formula (V)

(V)

wherein $R^{5'}$ is a group $R^5$ as previously defined, or a group convertible to $R^5$ and $R^{6'}$ is a group $R^6$ as previously defined, or a group convertible to $R^6$, Q is hydrogen or $C_{1-6}$alkyl and X and Y both represent leaving groups. X and Y can be the same or different and examples are Cl, PhO, EtO, imidazole. When X and Y are both Cl, i.e. phosgene, this reagent can be generated in situ e.g. from diphosgene or triphosgene.

The above reaction is carried out using standard methodology e.g. reacting the diamine (IV) with the reagent (V) in an inert solvent for example dichloromethane or toluene or dimethylformamide, optionally in the presence of a base such as triethylamine or potassium carbonate, and optionally with heating.

In a further aspect, the invention provides a general process (C) for preparing compounds of formula (I) which process comprises:
treatment of a compound of formula (VI)

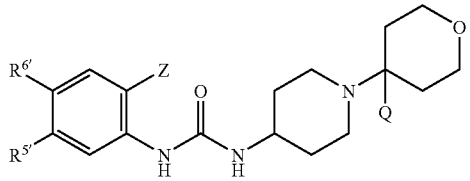

(VI)

with a palladium or copper catalyst (VII) to effect an intramolecular cyclisation
wherein $R^{5'}$ is a group $R^5$ as previously defined, or a group convertible to $R^5$ and $R^{6'}$ is a group $R^6$ as previously defined, or a group convertible to $R^6$, Q is hydrogen or $C_{1-6}$alkyl and Z is a leaving group such as bromo, iodo, chloro or triflate.

The cyclisation reaction can be carried out using a variety of palladium or copper reagents as described in the literature (JACS, 2003, 125, 6653, Tet. Lett., 2004, 45, 8535, or JACS, 2002, 124, 7421.)

In a further aspect, the invention provides a general process (D) for preparing compounds of formula (I) which process comprises:

coupling a compound of formula (VIII)

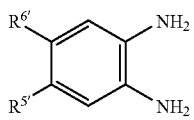
(VIII)

with a compound of formula (IX)

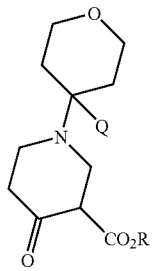
(IX)

wherein $R^{5'}$ is a group $R^5$ as previously defined, or a group convertible to $R^5$ and $R^{6'}$ is a group $R^6$ as previously defined, or a group convertible to $R^6$, Q is hydrogen or $C_{1-6}$alkyl and R is a $C_{1-5}$ alkyl group.

This condensation and cyclisation reactions can be carried out under reaction conditions similar to those described in the literature for an analogous process (U.S. Pat. No. 3,161,645) (heating in an inert solvent, for example xylene) followed by reduction of the piperidine double bond using for example catalytic hydrogenation over palladium or Raney nickel.

In a further aspect, the invention provides a general process (E) for preparing compounds of formula (I) which process comprises:
reaction of a compound of formula (X)

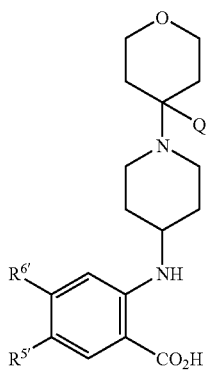
(X)

with diphenylphosphoryl azide or other reagent/combination of reagents to effect the Curtius rearrangement of compound (X), followed by intramolecular cyclisation.
wherein $R^{5'}$ is a group $R^5$ as previously defined, or a group convertible to $R^5$ and $R^{6'}$ is a group $R^6$ as previously defined, or a group convertible to $R^6$, and Q is hydrogen or $C_{1-6}$alkyl.

The Curtius rearrangement is typically carried out by mixing the two reactants in an inert solvent such as toluene, optionally with heating.

In a further aspect, the invention provides a general process (F) for preparing compounds of formula (I) which process comprises:
coupling a compound of formula (XI)

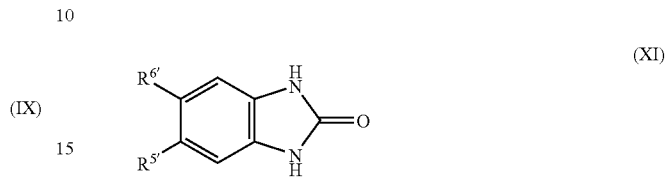
(XI)

with a compound of formula (XII)

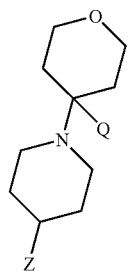
(XII)

wherein $R^{5'}$ is a group $R^5$ as previously defined, or a group convertible to $R^5$ and $R^{6'}$ is a group $R^6$ as previously defined, or a group convertible to $R^6$, Q is hydrogen or $C_{1-6}$alkyl and Z is hydroxy or a leaving group such as chloro, bromo or iodo, or alkyl/aryl sulfonate.

The alkylation reaction (Z=a leaving group) can be carried out under classical alkylation or Mitsunobu reaction (Z=OH) conditions. Using classical alkylation conditions, the benzimidazolone intermediate (XI) can be deprotonated using a base such as sodium hydride in an inert solvent such as dimethylformamide, and then treated with the alkylating reagent (XII), optionally with heating. The Mitsunobu reaction with (XII) Z=OH can be carried out using standard conditions e.g. triphenylphosphine and diethylazodicarboxylate in an inert solvent such as dichloromethane or tetrahydrofuran at room temperature Conversion of $R^{6'}$ to $R^6$ or interconversions or $R^6$ may be accomplished as indicated below:

for example, when $R^{6'}$ is a halogen, it can be converted to an alkoxy or trifluoromethyl group by copper catalysed reaction, using an alcohol, or methyl fluorosulfonyl(difluoro)acetate, respectively. It may alternatively be converted to an alkyl group with an organometallic reagent, for example an alkylstannane.

as another example, when $R^{6'}$ is hydroxy, it may be converted to alkoxy by reaction with an alkyl halide or sulfonate, or to trifluoromethoxy by conversion to the xanthate followed by oxidation in the presence of fluoride ion.

as a further example, when R$^{6'}$ is methyl, it may be converted to trifluoromethyl by chlorination or bromination followed by displacement of the introduced halogens with fluoride.

Conversion of R$^{5'}$ to R$^5$ or interconversions or R$^5$ may be accomplished in a manner similar to that indicated for conversion of R$^5$ to R$^6$ or interconversions or R$^6$.

Compounds of formula (II) are generally known in the literature or can be prepared by a range of different processes for example:

(a) displacement of an ortho-fluoro or ortho-chloro nitrobenzene intermediate (XIII) with the amine (XIV), wherein R$^{5'}$ is a group R$^5$ as previously defined, or a group convertible to R$^5$ and R$^{6'}$ is a group R$^6$ as previously defined, or a group convertible to R$^6$, and P represents a nitrogen protecting group e.g. Boc, acetyl, trifluoroacetyl, ethoxycarbonyl, benzyloxycarbonyl, to give (XXIII), followed by reduction of the nitro group, cyclisation using phosgene or a phosgene equivalent, and deprotection of the piperidine nitrogen using standard literature conditions (Scheme 1).

Compounds of formula (XIII) are commercially available or can be prepared by standard methodology. The compound (XIV) in which P=Boc is commercially available (b) metal catalysed cyclisation of an intermediate (XV) followed by deprotection of the piperidine nitrogen, wherein R$^{5'}$ is a group R$^5$ as previously defined, or a group convertible to R$^5$ and R$^{6'}$ is a group R$^6$ as previously defined, or a group convertible to R$^6$, P represents a nitrogen protecting group e.g. Boc, acetyl, trifluoroacetyl, benzyloxycarbonyl, and Z represents a leaving group such as bromo, iodo, chloro or triflate. Reaction conditions for the Buchwald cyclisation are summarised in Process C. The urea (XV) can be prepared using any of the classical methods for urea formation as illustrated in Scheme 2. The starting materials for this process are commercially available or can be prepared using standard methodology.

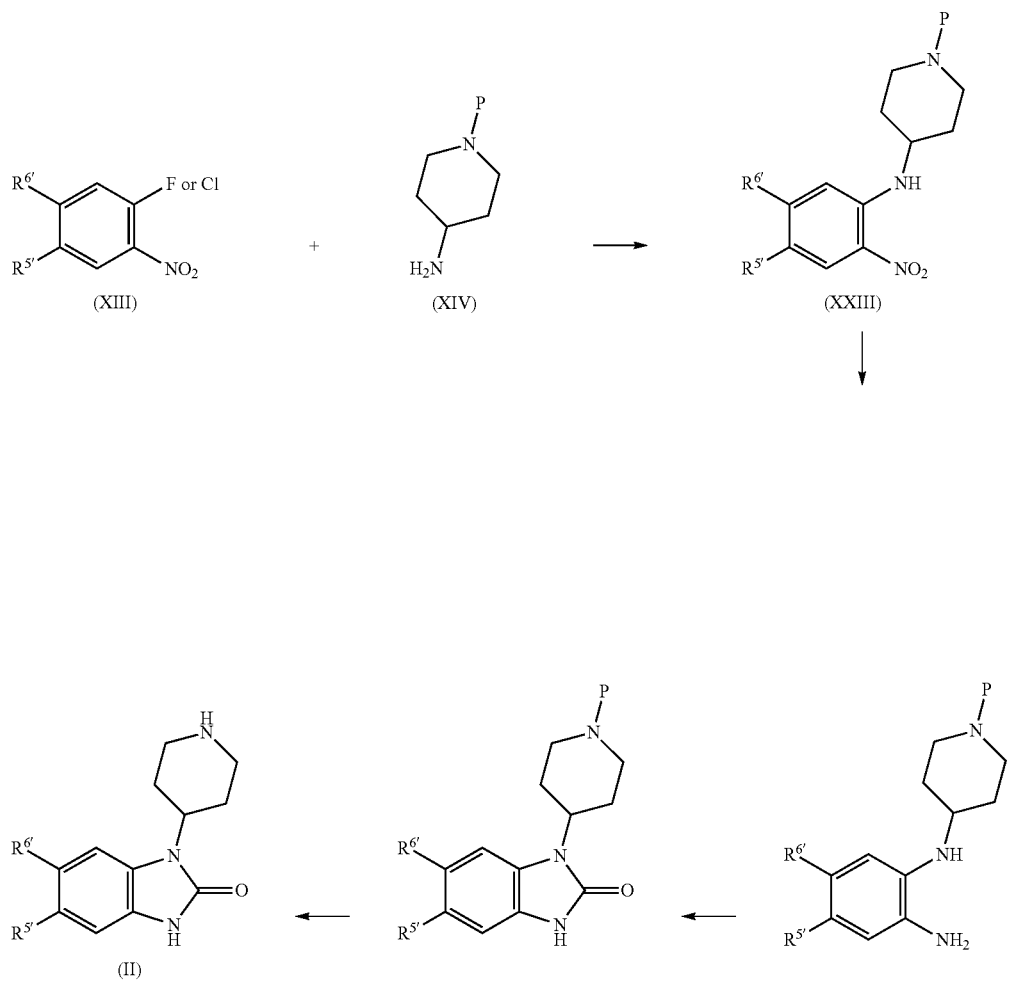

Scheme 1.

Scheme 2.

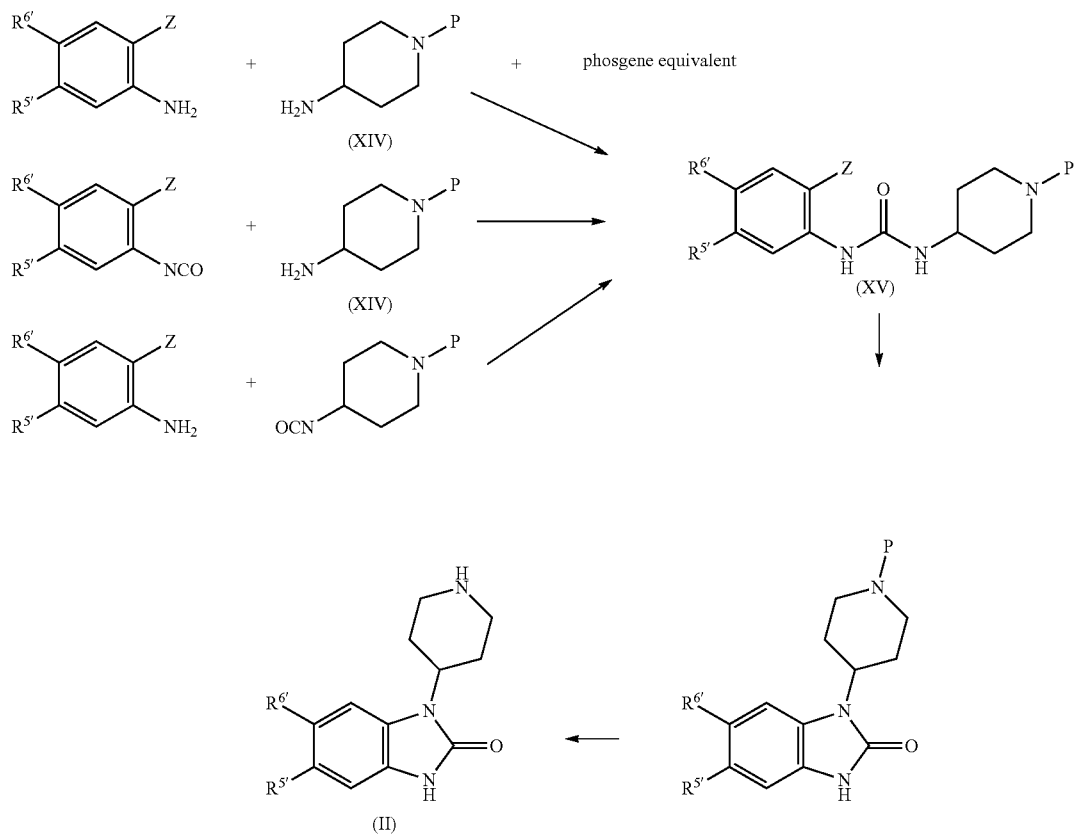

(c) Curtius rearrangement of an intermediate (XVI), wherein $R^{5'}$ is a group $R^5$ as previously defined, or a group convertible to $R^5$ and $R^{6'}$ is a group $R^6$ as previously defined, or a group convertible to $R^6$, P represents a nitrogen protecting group e.g. Boc, acetyl, trifluoroacetyl, benzyloxycarbonyl, and R represents H or a $C_{1-5}$ alkyl group e.g. methyl or ethyl, followed by intramolecular cyclisation and deprotection of the piperidine nitrogen (Scheme 3). The anthranilic acid or ester starting materials (XVII) are commercially available or can be made by standard methodology. The piperidone starting material (R=Boc or benzyl) is commercially available. The Curtius rearrangement can be effected using the conditions described under process E.

Scheme 3.

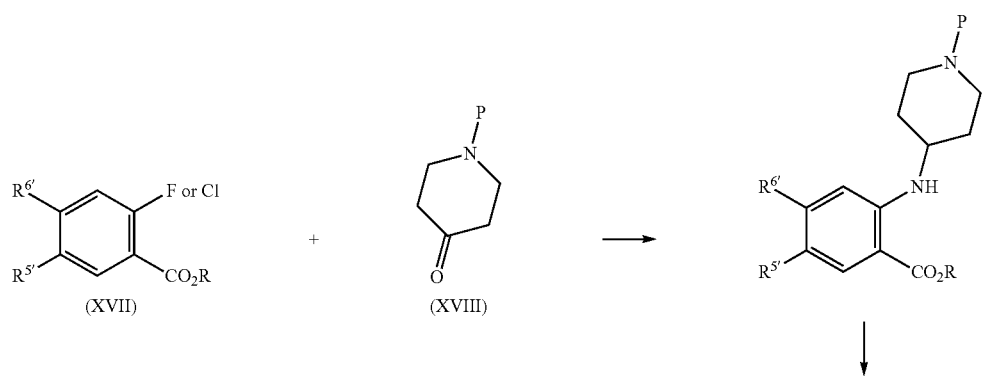

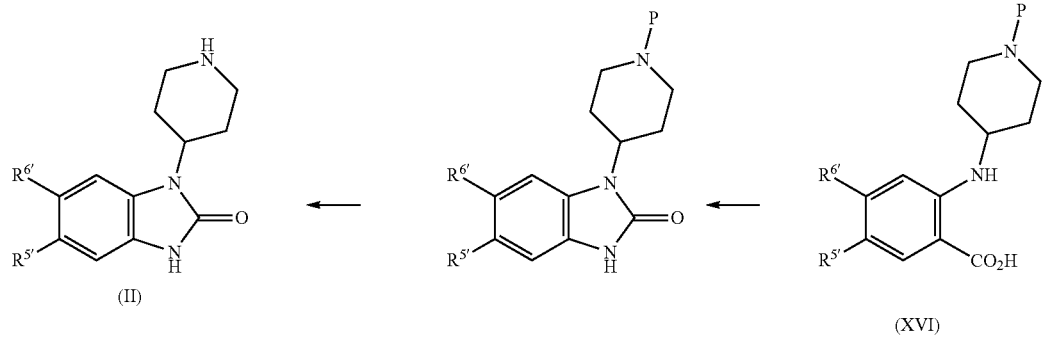

(d) Condensation of an orthophenylenediamine (VIII) with a 3-alkoxycarbonyl-4-piperidone (XX), wherein $R^{5'}$ is a group $R^5$ as previously defined, or a group convertible to $R^5$ and $R^{6'}$ is a group $R^6$ as previously defined, or a group convertible to $R^6$, P represents a nitrogen protecting group e.g. Boc, acetyl, trifluoroacetyl, benzyloxycarbonyl and R is a C1-5 alkyl group (Scheme 4), by heating in an inert solvent at elevated temperature, to afford the tetrahydropyridine intermediate (XXI). Hydrogenation of the double bond and deprotection of the piperidine nitrogen can be accomplished separately or concomitantly dependent on the precise nature of the protecting group P, to afford the desired product (II). Compounds of formula (VIII) are commercially available or can be prepared by standard methodology. Compounds of formula (XX) are commercially available or can be prepared by standard methodology.

(e) Reductive alkylation of an ortho nitroaniline (XXII) with an N-protected 4-piperidone (XVIII), wherein $R^{5'}$ is z group $R^5$ as previously defined, or a group convertible to $R^5$ and $R^{6'}$ is a group $R^6$ as previously defined, or a group convertible to $R^6$, and P represents a nitrogen protecting group e.g. Boc, acetyl, trifluoroacetyl, benzyloxycarbonyl, using for example sodium triacetoxyborohydride to give the intermediate (XXIII). Reduction of the nitro group, followed by cyclisation and deprotection as described hereinbefore provides the desired product (II) (Scheme 5). Compounds of formula (XXII) and (XVIII) are commercially available or can be prepared by standard methodology Scheme 4.

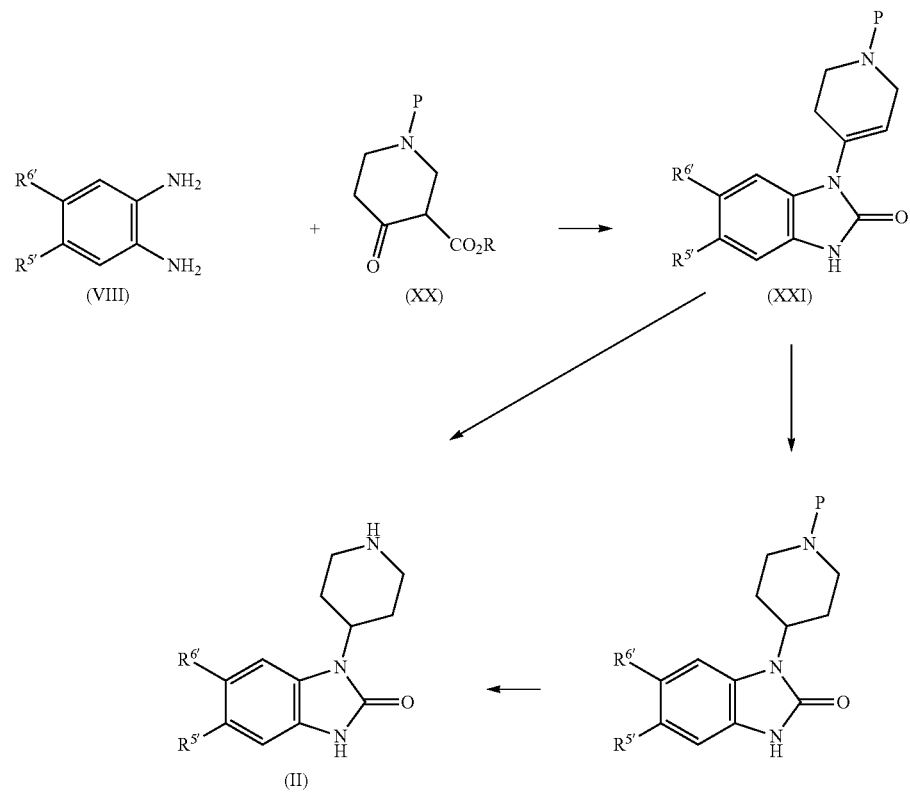

Scheme 5.

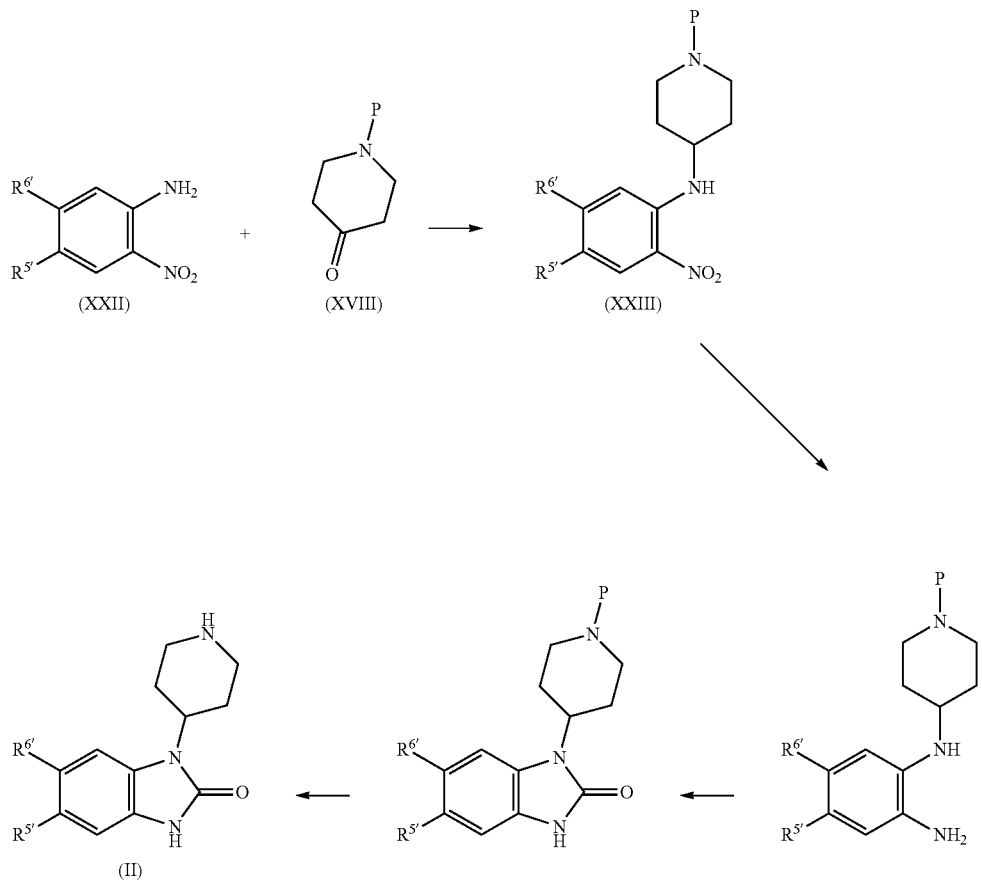

(f) metal catalysed reaction between the amine (XIV) and a suitably substituted nitrobenzene compound (XXIV) wherein $R^{5'}$ is a group $R^5$ as previously defined, or a group convertible to $R^5$ and $R^{6'}$ is a group $R^6$ as previously defined, or a group convertible to $R^6$, P represents a nitrogen protecting group e.g. Boc, acetyl, trifluoroacetyl, benzyloxycarbonyl, and Z represents a leaving group such as bromo, iodo, chloro or triflate (Scheme 6). This process generates intermediates of formula (XXIII) and subsequent reactions are similar to that for Scheme 5. Compounds of formula (XXIV) are commercially available or can be prepared by known methodology. The compound (XIV) in which P=Boc is commercially available Scheme 6.

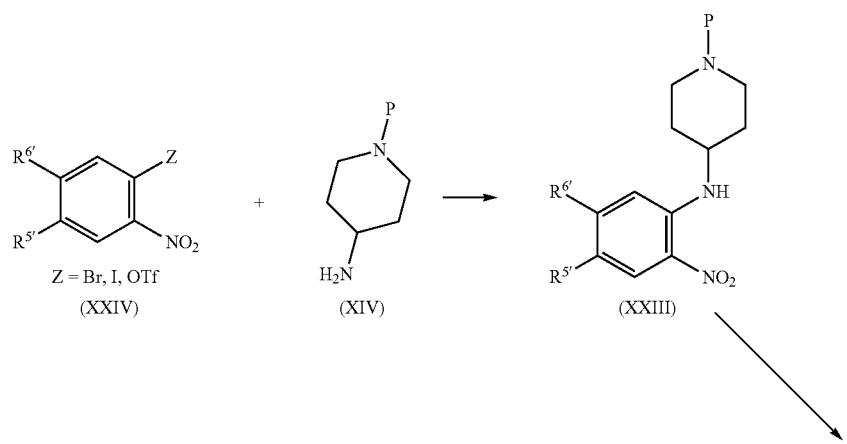

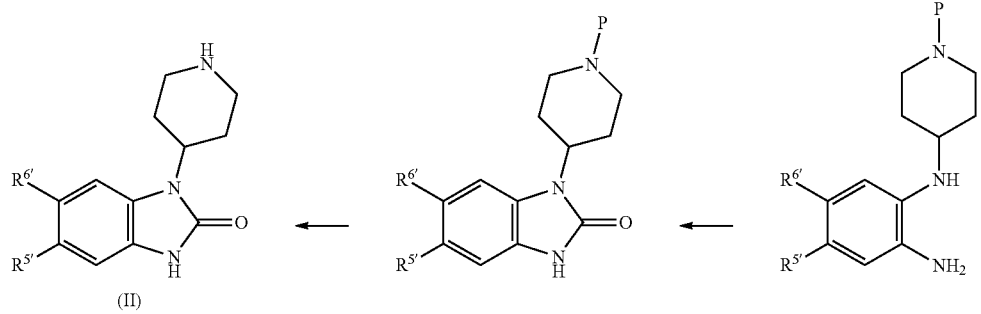

(g) metal catalysed reaction between the amine (XIV) and the protected aniline (XXV), wherein $R^{5'}$ is a group $R^5$ as previously defined, or a group convertible to $R^5$ and $R^{6'}$ is a group $R^6$ as previously defined, or a group convertible to $R^6$, P represents a nitrogen protecting group e.g. Boc, acetyl, trifluoroacetyl, benzyloxycarbonyl, and Z represents a leaving group such as bromo, iodo, chloro or triflate, to give the intermediate (XXVI) (Scheme 7) Deprotection of the aniline followed by the same reaction sequence as in Scheme 6 affords the desired intermediate (II). Compounds of formula (XXV) are commercially available or can be prepared by known methodology e.g. halogenation ortho to the aniline group. The compound (XIV) in which P=Boc is commercially available The compound of formula (III) is commercially available.

Compounds of formula (IV) can be prepared by a number of different processes e.g.

(h) displacement of an ortho-fluoro or ortho-chloro nitrobenzene intermediate (XIII) with the amine (XXVII) to afford compound (XXVIII), wherein $R^{5'}$ is a group $R^5$ as previously defined, or a group convertible to $R^5$ and $R^{6'}$ is a group $R^6$ as previously defined, or a group convertible to $R^6$, and Q is hydrogen or $C_{1-6}$alkyl, followed by reduction of the nitro group using standard conditions e.g. hydrogenation over palladium or Raney nickel (Scheme 8). Compounds of formula (XIII) are commercially available or can be prepared by standard methodology.

Scheme 7.

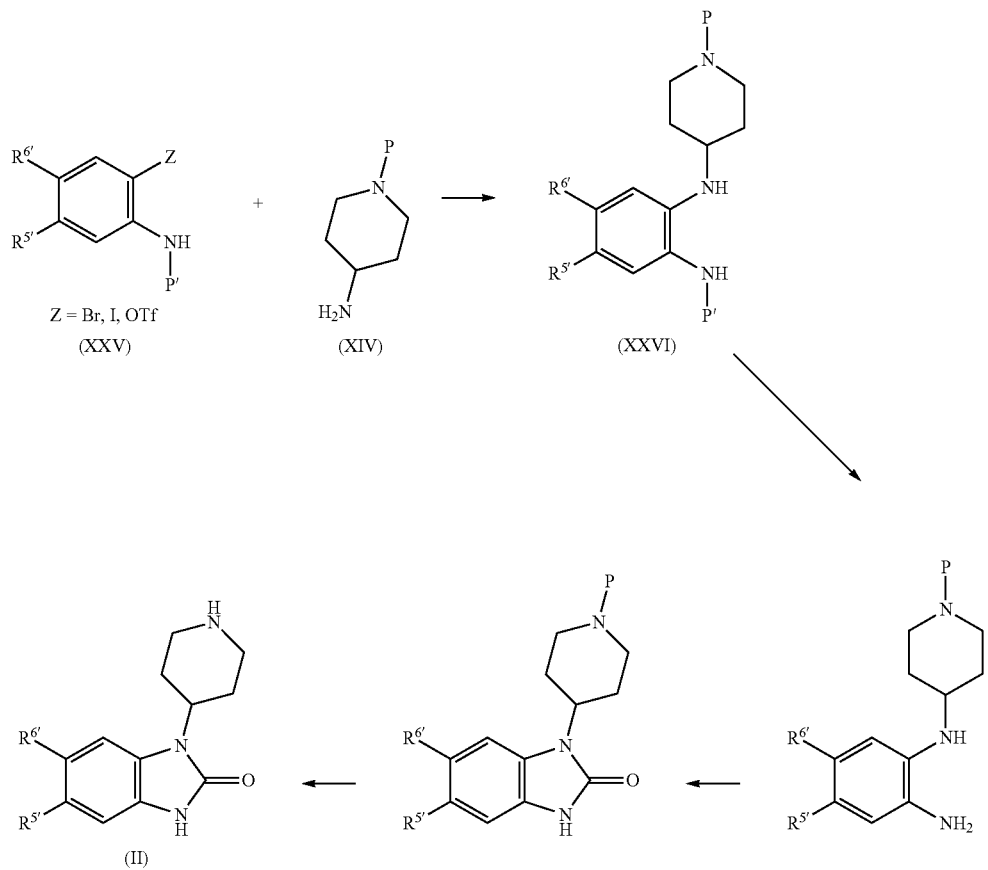

Scheme 8.

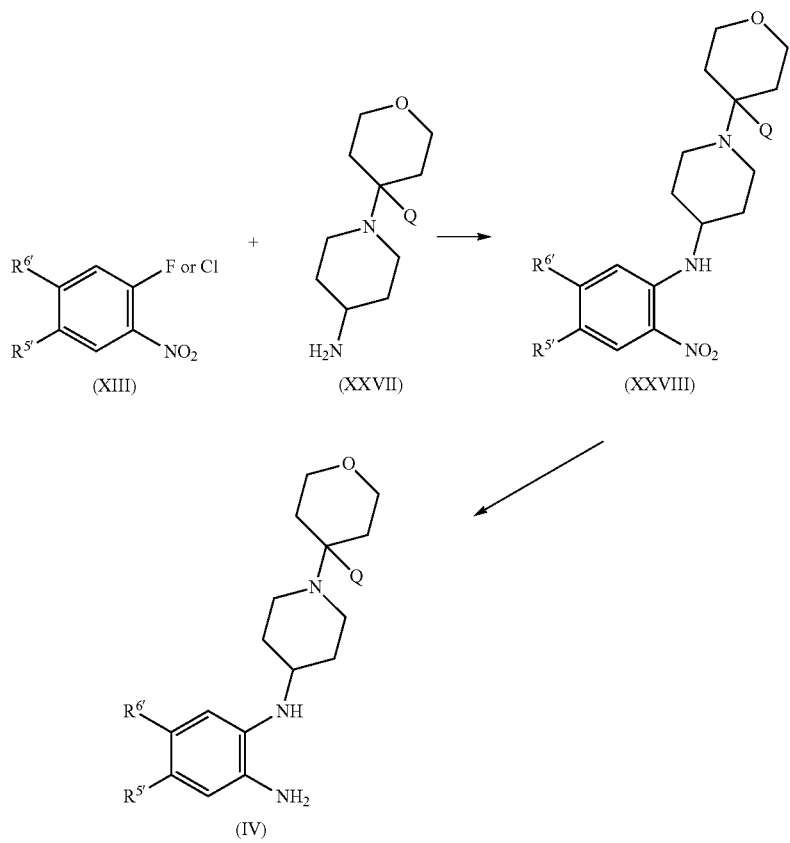

(i) metal catalysed reaction of the amine (XXVII) with the ortho substituted nitrobenzene (XXIX) to afford compound (XXVIII) wherein $R^{5'}$ is a group $R^5$ as previously defined, or a group convertible to $R^5$ and $R^{6'}$ is a group $R^6$ as previously defined, or a group convertible to $R^6$ (Scheme 9), and Q is hydrogen or $C_{1-6}$alkyl, followed by the same reactions as illustrated in Scheme 8. Compounds of formula (XXIX) are commercially available or can be prepared by standard methodology.

Scheme 9.

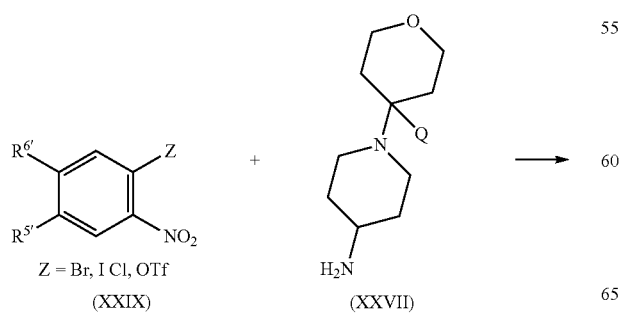

-continued

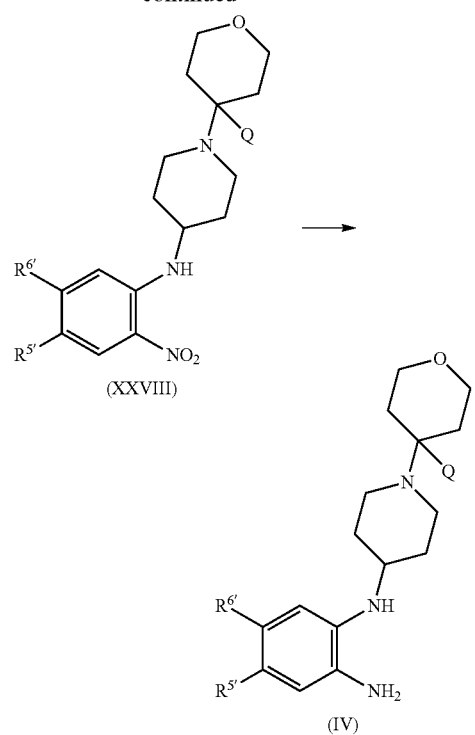

(j) metal catalysed reaction of the amine (XXVII) with the protected aniline derivative (XXV), wherein $R^{5'}$ is a group $R^5$ as previously defined, or a group convertible to $R^5$ and $R^{6'}$ is a group $R^6$ as previously defined, or a group convertible to $R^6$, Q is hydrogen or $C_{1-6}$alkyl, and P represents a nitrogen protecting group such as acetyl, trifluoroacetyl, Boc, phthalimide, to afford compound (XXXI) (Scheme 10) followed by deprotection of the aniline group. Compounds of formula (XXV) are commercially available or can be prepared by standard methodology.

(k) Reductive alkylation of an ortho nitroaniline (XXII) with the piperidone (XXXII) wherein $R^{5'}$ is a group $R^5$ as previously defined, or a group convertible to $R^5$ and $R^{6'}$ is a group $R^6$ as previously defined, or a group convertible to $R^6$, and Q is hydrogen or $C_{1-6}$alkyl, using for example sodium triacetoxyborohydride in dichloroethane to give the intermediate (XXVIII) (Scheme 11). Reduction of the nitro group using, for example, palladium on carbon or Raney nickel affords the desired intermediate (IV).

Scheme 10.

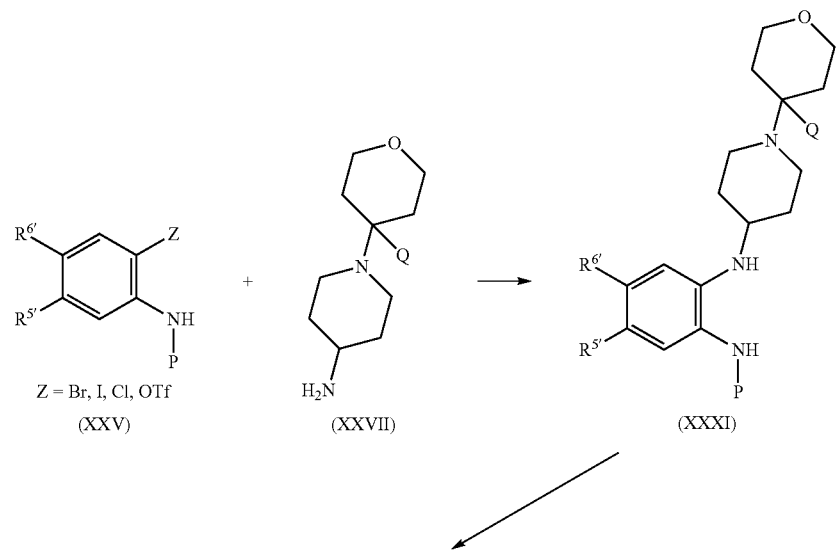

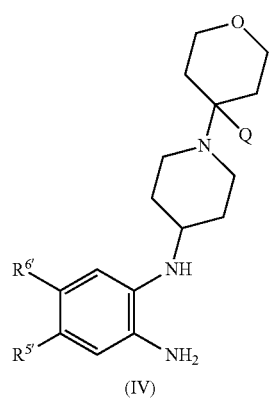

(IV)

Scheme 11.

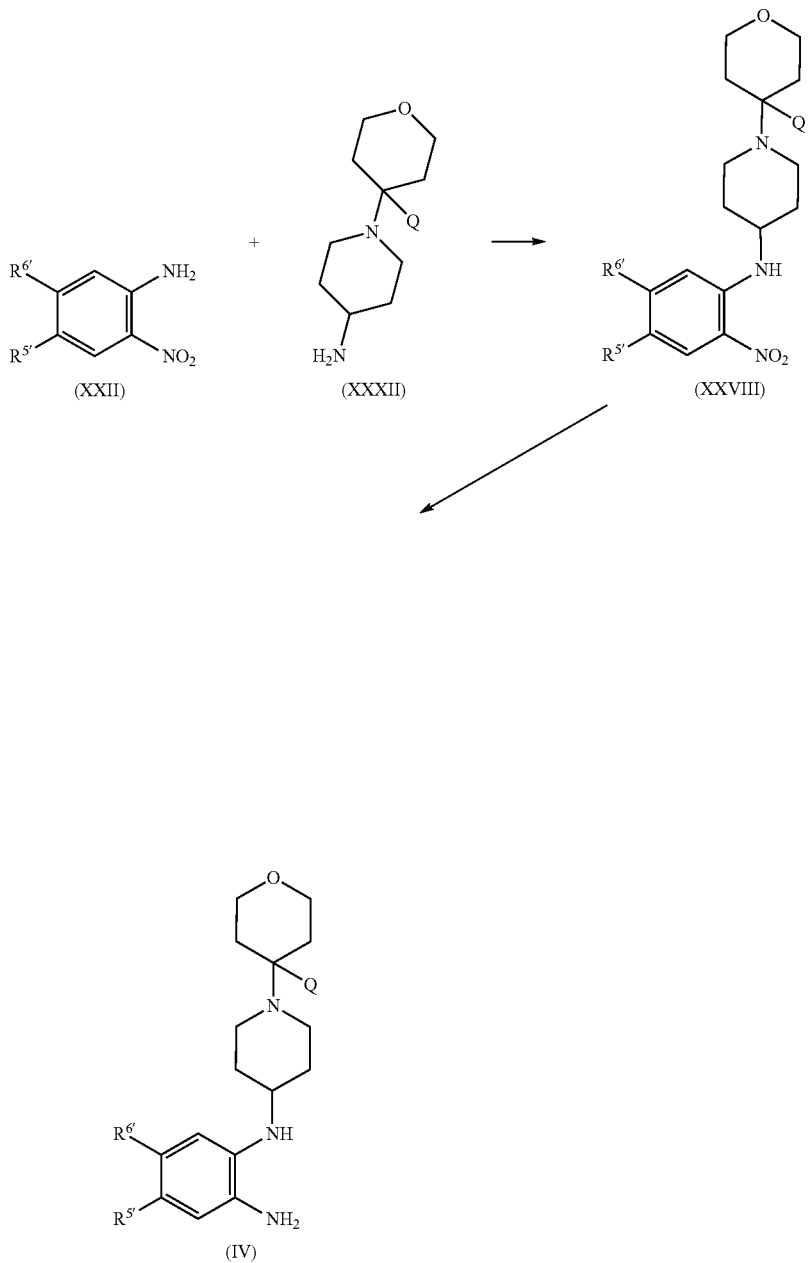

Compounds of formula (V) are commercially available e.g. carbonyl diimidazole, phosgene, phosgene solution in toluene, diphosgene, triphosgene, phenyl chloroformate, diethyl carbonate.

Compounds of formula (VI) can be prepared by a variety of processes e.g. urea formation can be achieved as shown in Scheme 12 by combining the two amines (XXXIV) and (XXVII) with phosgene or a phosgene equivalent using standard conditions Phosgene equivalents include carbonyl diimidazole, diphosgene, triphosgene, phenyl chloroformate reacting the amine (XXVII) with the isocyanate (XXXV)

reacting the amine (XXXIV) with the isocyanate (XXXVI)

Both isocyanates (XXXV) and (XXXIV), wherein $R^{5'}$ is a group $R^5$ as previously defined, or a group convertible to $R^5$ and $R^{6'}$ is a group $R^6$ as previously defined, or a group convertible to $R^6$, and Q is hydrogen or $C_{1-6}$alkyl, can be prepared from the corresponding amines using standard methodology for isocyanate formation.

Scheme 12.

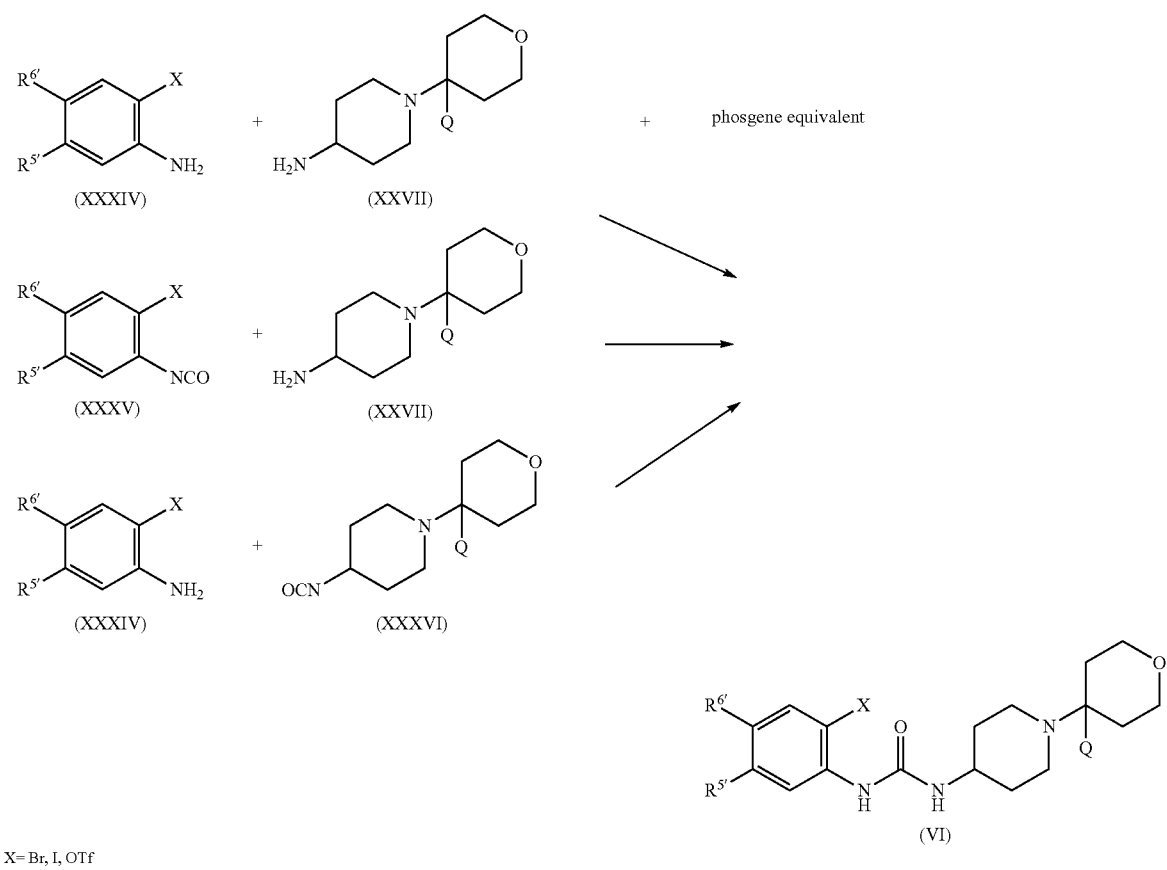

X= Br, I, OTf

Palladium and copper catalysts (VII) are commercially available or can be prepared as described in the literature (see references in Process C).

Compounds of formula (VIII) are commercially available or can be prepared by known literature routes e.g. reduction of a mono or dinitrobenzene precursor.

Compounds of formula (IX) can be prepared by reductive alkylation of the 3-alkoxycarbonyl-4-piperidone with tetrohydropyran-4-one.

Compounds of formula (X) wherein $R^{5'}$ is a group $R^5$ as previously defined, or a group convertible to $R^5$ and $R^{6'}$ is a group $R^6$ as previously defined, or a group convertible to $R^6$, and Q is hydrogen or $C_{1-6}$alkyl, can be prepared as shown in Scheme 13. Reductive alkylation of an anthranilic acid or ester (XVII) with the ketone (XXXII), followed if appropriate by hydrolysis of the ester group.

Scheme 13.

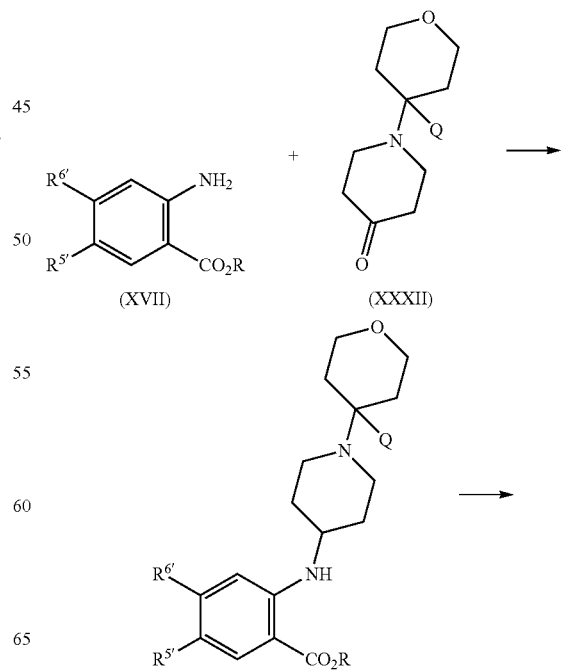

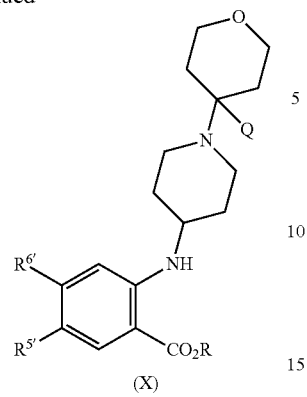

(X)

Compounds of formula (XI) are commercially available or can be prepared by literature processes.

Compounds of formula (XII) can be prepared as shown in Scheme 14, by reductive alkylation of (XXXVII) where Z' represents Z or a group convertible to Z with the ketone (III), and Q=H. Conversion of a Z' hydroxy group to Z=chloro or bromo can be accomplished using standard methodology e.g. treatment with thionyl chloride or triphenylphosphine/carbon tetrabromide.

Scheme 14.

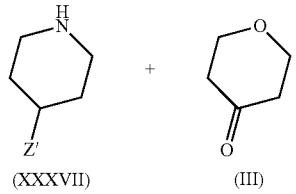

(XXXVII)   (III)   (XII)

The compound (XXVII) where Q=H can be prepared as shown in Scheme 15. Reductive alkylation of the commercially available amine (XXXVIII) with tetrahydropyran-4-one (III) using for example sodium triacetoxyborohydride in dichloroethane provides the intermediate (XXXIX) which is deprotected using HCl in ethanol or trifluoroacetic acid to afford the primary amine (XXVII).

Scheme 15.

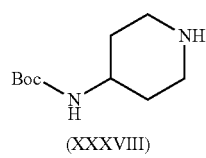    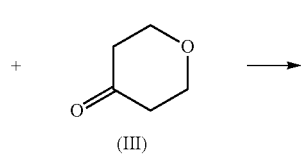

(XXXVIII)        (III)

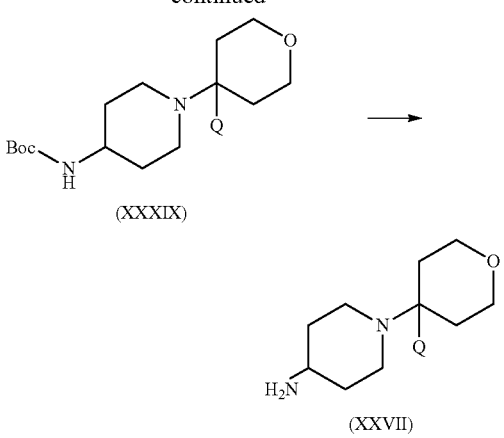

(XXXIX)

(XXVII)

The invention accordingly further provides compounds of formula (II)

(II)

a compound of formula (IV)

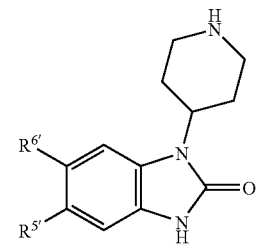

(IV)

a compound of formula (VI)

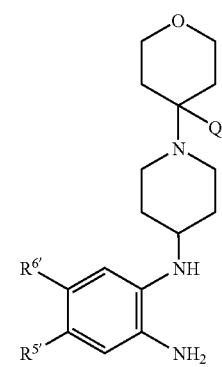

(VI)

and a compound of formula (X)

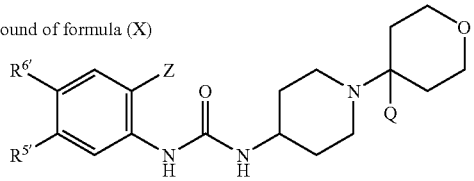

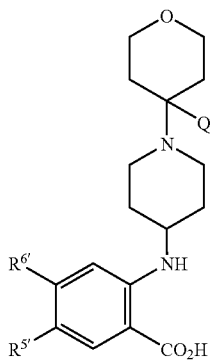
(X)

wherein R⁵' is a group R⁵ as previously defined, or a group convertible to R⁵ and R⁶' is a group R⁶ as previously defined, or a group convertible to R⁶, Q is hydrogen or $C_{1-6}$alkyl and Z is a leaving group, for example such as bromo, iodo, chloro or triflate.

Compounds (II), (IV), (VI) and (X) are useful as intermediates in the synthesis of compounds of formula (I).

The compounds of formula (I) are expected to be useful in the treatment of psychotic disorders or cognitive impairment.

The terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term psychotic disorder includes Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9);

Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-induced Mood Disorder (including the subtypes With Depressive Features, With Manic Features and With Mixed Features) and Mood Disorder Not Otherwise Specified (296.90);

Anxiety disorders including Social Anxiety Disorder, Panic Attack, Agoraphobia, Panic Disorder, Agoraphobia Without History of Panic Disorder (300.22), Specific Phobia (300.29) including the subtypes Animal Type, Natural Environment Type, Blood-Injection-Injury Type, Situational Type and Other Type), Social Phobia (300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-induced Anxiety Disorder and Anxiety Disorder Not Otherwise Specified (300.00);

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-induced Persisting Dementia, Substance-Induced Persisting Amnestic Disorder, Substance-Induced Psychotic Disorder, Substance-Induced Mood Disorder, Substance-Induced Anxiety Disorder, Substance-induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-induced Psychotic Disorder, Alcohol-Induced Mood Disorder, Alcohol-induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-induced Anxiety Disorder, Caffeine-induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-induced Persisting Dementia, Inhalant-induced Psychotic Disorder, Inhalant-induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide;

Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition; and Substance-Induced Sleep Disorder including the subtypes Insomnia Type, Hypersomnia Type, Parasomnia Type and Mixed Type;

Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; and Eating Disorder Not Otherwise Specified (307.50);

Autistic Disorder (299.00); Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23);

Personality Disorders including the subtypes Paranoid Personality Disorder (301.0), Schizoid Personality Disorder (301.20), Schizotypal Personality Disorder (301.22), Antisocial Personality Disorder (301.7), Borderline Personality Disorder (301.83), Histrionic Personality Disorder (301.50), Narcissistic Personality Disorder (301.81), Avoidant Personality Disorder (301.82), Dependent Personality Disorder (301.6), Obsessive-Compulsive Personality Disorder (301.4) and Personality Disorder Not Otherwise Specified (301.9); and Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

The compounds of Formula (I) are also expected to be useful for the enhancement of cognition, including both the treatment of cognitive impairment on its own and the treatment of cognition impairment in other diseases such as schizophrenia, bipolar disorder, depression, other psychiatric disorders and psychotic conditions associated with cognitive impairment.

Within the context of the present invention, the term cognitive impairment includes, for example, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Alzheimer's disease, Huntington's disease, Pick disease, Aids-related dementia or other dementia states such as Multiinfarct dementia, alcoholic dementia, hypothyroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, mild cognitive impairment, age related cognitive impairment, autism related cognitive impairment, Down's syndrome, cognitive deficit related to psychosis, and post-electroconvulsive treatment related cognitive disorders; and dyskinetic disorders such as Parkinson's disease, neuroleptic-induced parkinsonism, and tardive dyskinesias.

The therapy of the present invention may also be used as a memory and/or cognition enhancer in healthy humans with no cognitive and/or memory deficit.

In a further aspect therefore, the invention provides a compound of formula (I) as hereinbefore described or a salt or solvate thereof for use in therapy.

In another aspect, the invention provides a compound of formula (I) or a salt or solvate thereof for use in the treatment of a condition which requires agonism of a muscarinic $M_1$ receptor.

In another aspect, the invention provides a compound of formula (I) as hereinbefore described or a salt or solvate thereof for use in the treatment of a psychotic disorder. The invention also provides a compound of formula (I) as hereinbefore described or a salt or solvate thereof for use in the treatment of cognitive impairment.

In another aspect, the invention provides the use of a compound of formula (I) as hereinbefore described or a salt or solvate thereof in the manufacture of a medicament for the treatment of a condition which requires agonism of a muscarinic $M_1$ receptor.

In another aspect, the invention provides the use of a compound of formula (I) as hereinbefore described or a salt or solvate thereof in the manufacture of a medicament for the treatment of a psychotic disorder. The invention also provides the use of a compound of formula (I) as hereinbefore described or a salt or solvate thereof in the manufacture of a medicament for the treatment of cognitive impairment.

In another aspect, the invention provides a method of treating a condition which requires agonism of a muscarinic $M_1$ receptor, which comprises administering to a mammal in need thereof an effective amount of a compound of formula (I) as hereinbefore described or a salt or solvate thereof.

In another aspect, the invention provides a method of treating a psychotic disorder which comprises administering to a mammal in need thereof an effective amount of a compound of formula (I) as hereinbefore described or a salt or solvate thereof. The invention also provides a method of treating cognitive impairment, which comprises administering to a mammal in need thereof an effective amount of a compound of formula (I) as hereinbefore described or a salt or solvate thereof.

The compounds of formula (I) and their salts and solvates thereof may also be suitable for combination with other actives, such as typical and atypical antipsychotics, mood stabilisers, antidepressants, anxiolytics, drugs for extrapyrimidal side effects and cognitive enhancers to provide improved treatment of psychotic disorders.

The combination therapies of the invention are, for example, administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of formula (I) or a salt or solvate thereof and at least one antipsychotic agent, a mood stabiliser, an antidepressant, an anxiolytic, a drug for extrapyrimidal side effects or a cognitive enhancer are within the scope of the current invention. In one embodiment of adjunctive therapeutic administration as described herein, a patient is typically stabilised on a therapeutic administration of one or more of the components for a period of time and then receives administration of another component. The compounds of formula (I) or a salt or solvate thereof may be administered as adjunctive therapeutic treatment to patients who are receiving administration of at least one antipsychotic agent, a mood stabiliser, an antidepressant, an anxiolytic, a drug for extrapyrimidal side effects or a cognitive enhancer, but the scope of the invention also includes the adjunctive therapeutic administration of at least one antipsychotic agent, a mood stabiliser, an antidepressant, an anxiolytic, a drug for extrapyrimidal side effects or a cognitive enhancer to patients who are receiving administration of compounds of formula (I) or a salt or solvate thereof.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

In a further aspect therefore, the invention provides a method of treatment of a psychotic disorder by adjunctive therapeutic administration of compounds of formula (I) or a salt or solvate thereof to a patient receiving therapeutic administration of at least one antipsychotic agent. In a further aspect, the invention provides the use of compounds of formula (I) or a salt or solvate thereof in the manufacture of a medicament for adjunctive therapeutic administration for the treatment of a psychotic disorder in a patient receiving therapeutic administration of at least one antipsychotic agent. The invention further provides compounds of formula (I) or a salt or solvate thereof for use for adjunctive therapeutic administration for the treatment of a psychotic disorder in a patient receiving therapeutic administration of at least one antipsychotic agent.

In a further aspect, the invention provides a method of treatment of a psychotic disorder by adjunctive therapeutic administration of at least one antipsychotic agent to a patient receiving therapeutic administration of compounds of formula (I) or a salt or solvate thereof. In a further aspect, the invention provides the use of at least one antipsychotic agent in the manufacture of a medicament for adjunctive therapeutic administration for the treatment of a psychotic disorder in a patient receiving therapeutic administration of compounds of formula (I) or a salt or solvate thereof. The invention further provides at least one antipsychotic agent for adjunctive therapeutic administration for the treatment of a psychotic disorder in a patient receiving therapeutic administration of compounds of formula (I) or a salt or solvate thereof.

In a further aspect, the invention provides a method of treatment of a psychotic disorder by simultaneous therapeutic administration of compounds of formula (I) or a salt or solvate thereof in combination with at least one antipsychotic agent. The invention further provides the use of a combination of compounds of formula (I) or a salt or solvate thereof and at least one antipsychotic agent in the manufacture of a medicament for simultaneous therapeutic administration in the treatment of a psychotic disorder. The invention further provides the use of compounds of formula (I) or a salt thereof in the manufacture of a medicament for simultaneous therapeutic administration with at least one antipsychotic agent in the treatment of a psychotic disorder. The invention further provides compounds of formula (I) or a salt thereof for use for simultaneous therapeutic administration with at least one antipsychotic agent in the treatment of a psychotic disorder. The invention further provides the use of at least one antipsychotic agent in the manufacture of a medicament for simultaneous therapeutic administration with compounds of formula (I) or a salt thereof in the treatment of a psychotic disorder.

In a further aspect, the invention provides a kit-of-parts for use in the treatment of a psychotic disorder comprising a first dosage form comprising compounds of formula (I) or a salt or solvate thereof and one or more further dosage forms each comprising a antipsychotic agent for simultaneous therapeutic administration.

In another aspect, the invention provides a method of treatment of a psychotic disorder by adjunctive therapeutic administration of a compound of the present invention to a patient receiving therapeutic administration of an active ingredient selected from the group consisting of: a mood stabiliser, an antidepressant, an anxiolytic, a drug for extrapyrimidal side effects and a cognitive enhancer.

In a further aspect, the invention provides the use of a compound of the present invention in the manufacture of a medicament for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyrimidal side effects and a cognitive enhancer.

The invention also provides the use of a compound of the present invention in adjunctive therapeutic administration for the treatment of a psychotic disorder in a patient receiving therapeutic administration of an active ingredient selected from the group consisting of: a mood stabiliser, an antidepressant, an anxiolytic, a drug for extrapyrimidal side effects and a cognitive enhancer.

The invention further provides the use of a compound of the present invention for use for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyrimidal side effects and a cognitive enhancer.

In a further aspect, the invention provides a method of treatment of a psychotic disorder by adjunctive therapeutic administration of an active ingredient selected from the group consisting of: a mood stabiliser, an antidepressant, an anxiolytic, a drug for extrapyrimidal side effects and a cognitive enhancer to a patient receiving therapeutic administration of a compound of the present invention.

In a further aspect, the invention provides the use of an active ingredient selected from the group consisting of: a mood stabiliser, an antidepressant, an anxiolytic, a drug for extrapyrimidal side effects and a cognitive enhancer in the manufacture of a medicament for adjunctive therapeutic administration for the treatment of a psychotic disorder in a patient receiving therapeutic administration of a compound of the present invention.

The invention also provides the use of an active ingredient selected from the group consisting of: a mood stabiliser, an antidepressant, an anxiolytic, a drug for extrapyrimidal side effects and a cognitive enhancer for adjunctive therapeutic administration for the treatment of a psychotic disorder in a patient receiving therapeutic administration of a compound of the present invention In a further aspect, the invention provides a method of treatment of a psychotic disorder by simultaneous therapeutic administration of a compound of the present invention in combination with an active ingredient selected from the group consisting of: a mood stabiliser, an antidepressant, an anxiolytic, a drug for extrapyrimidal side effects and a cognitive enhancer.

The invention further provides the use of a combination of a compound of the present invention and an active ingredient selected from the group consisting of: a mood stabiliser, an antidepressant, an anxiolytic, a drug for extrapyrimidal side effects and a cognitive enhancer in the manufacture of a medicament for simultaneous therapeutic administration in the treatment of a psychotic disorder.

The invention further provides the use of a combination of a compound of the present invention and an active ingredient selected from the group consisting of: a mood stabiliser, an antidepressant, an anxiolytic, a drug for extrapyrimidal side effects and a cognitive enhancer for simultaneous therapeutic administration in the treatment of a psychotic disorder.

The invention further provides the use of a compound of the present invention in the manufacture of a medicament for simultaneous therapeutic administration with an active ingredient selected from the group consisting of: a mood stabiliser, an antidepressant, an anxiolytic, a drug for extrapyrimidal side effects and a cognitive enhancer in the treatment of a psychotic disorder.

The invention further provides the use of a compound of the present invention for simultaneous therapeutic administration with an active ingredient selected from the group consisting of: a mood stabiliser, an antidepressant, an anxiolytic, a drug for extrapyrimidal side effects and a cognitive enhancer in the treatment of a psychotic disorder.

The invention further provides a compound of the present invention for use for simultaneous therapeutic administration with an active ingredient selected from the group consisting of: a mood stabiliser, an antidepressant, an anxiolytic, a drug for extrapyrimidal side effects and a cognitive enhancer in the treatment of a psychotic disorder.

The invention further provides the use of an active ingredient selected from the group consisting of: a mood stabiliser, an antidepressant, an anxiolytic, a drug for extrapyrimidal side effects and a cognitive enhancer in the manufacture of a medicament for simultaneous therapeutic administration with a compound of the present invention in the treatment of a psychotic disorder.

The invention further provides the use of an active ingredient selected from the group consisting of: a mood stabiliser, an antidepressant, an anxiolytic, a drug for extrapyrimidal side effects and a cognitive enhancer for simultaneous therapeutic administration with a compound of the present invention in the treatment of a psychotic disorder.

In a further aspect, the invention provides a kit-of-parts for use in the treatment of a psychotic disorder comprising a first dosage form comprising a compound of the present invention and one or more further dosage forms each comprising an active ingredient selected from the group consisting of: a mood stabiliser, an antidepressant, an anxiolytic, a drug for extrapyrimidal side effects and a cognitive enhancer for simultaneous therapeutic administration.

Examples of antipsychotic drugs that may be useful in the present invention include, but are not limited to: sodium channel blockers; mixed 5HT/dopamine receptor antagonists; mGluR5 positive modulators; D3 antagonists; 5HT6 antagonists; nicotinic alpha-7 modulators; glycine transporter GlyT1 inhibitors; D2 partial agonist/D3 antagonist/H3 antagonists; AMPA modulators; NK3 antagonists such as osanetant and talnetant; an atypical antipsychotic, for example clozapine, olanzapine, risperidone, quetiapine, aripirazole, ziprasidone and amisulpride; butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazine, and acetophenazine; thioxanthenes, such as thiothixene and chlorprothixene; thienobenzodiazepines; dibenzodiazepines; benzisoxazoles; dibenzothiazepines; imidazolidinones; benzisothiazolyl-piperazines; triazine such as lamotrigine; dibenzoxazepines, such as loxapine;

dihydroindolones, such as molindone; aripiprazole; and derivatives thereof that have antipsychotic activity.

Examples of tradenames and suppliers of selected antipsychotic drugs that may be suitable for use in the present invention are as follows: clozapine (available under the tradename CLOZARIL®, from Mylan, Zenith Goldline, UDL, Novartis); olanzapine (available under the tradename ZYPREXA®, from Lilly; ziprasidone (available under the tradename GEODON®, from Pfizer); risperidone (available under the tradename RISPERDAL®, from Janssen); quetiapine fumarate (available under the tradename SEROQUEL®, from AstraZeneca); sertindole (available under the tradename SERLECT®); amisulpride (available under the tradename SOLION®, from Sanofi-Synthelabo); haloperidol (available under the tradename HALDOL®, from Ortho-McNeil); haloperidol decanoate (available under the tradename HALDOL Decanoate®); haloperidol lactate (available under the tradenames HALDOL® and INTENSOL®); chlorpromazine (available under the tradename THORAZINE®, from SmithKline Beecham (GSK); fluphenazine (available under the tradename PROLIXIN®, from Apothecon, Copley, Schering, Teva, and American Pharmaceutical Partners, Pasadena); fluphenazine decanoate (available under the tradename PROLIXIN Decanoate®); fluphenazine enanthate (available under the tradename PROLIXIN®); fluphenazine hydrochloride (available under the tradename PROLIXIN®); thiothixene (available under the tradename NAVANE®; from Pfizer); thiothixene hydrochloride (available under the tradename NAVANE®); trifluoperazine (10-[3-(4-methyl-1-piperazinyl)propyl]-2-(trifluoromethyl)phenothiazine dihydrochloride, available under the tradename STELAZINE®, from SmithKline Beckman; perphenazine (available under the tradename TRILAFON®; from Schering); perphenazine and amitriptyline hydrochloride (available under the tradename ETRAFON TRILAFON®); thioridazine (available under the tradename MELLARIL®; from Novartis, Roxane, HiTech, Teva, and Alpharma); molindone (available under the tradename MOBAN®, from Endo); molindone hydrochloride (available under the tradename MOBAN®); loxapine (available under the tradename LOXITANE®; from Watson); loxapine hydrochloride (available under the tradename LOXITANE®); and loxapine succinate (available under the tradename LOXITANE®). Furthermore, benperidol (Glianimon®), perazine (Taxilan®) or melperone (Eunerpan®)) may be used.

Other suitable antipsychotic drugs include promazine (available under the tradename SPARINE®), triflurpromazine (available under the tradename VESPRIN®), chlorprothixene (available under the tradename TARACTAN®), droperidol (available under the tradename INAPSINE®), acetophenazine (available under the tradename TINDAL®), prochlorperazine (available under the tradename COMPAZINE®), methotrimeprazine (available under the tradename NOZINAN®), pipotiazine (available under the tradename PIPOTRIL®), iloperidone, pimozide and flupenthixol.

The antipsychotic drugs listed above by Tradename may also be available from other suppliers under a different Tradename.

In one further aspect of the invention, suitable antipsychotic agents include olanzapine, risperidone, quetiapine, aripiprazole, haloperidol, clozapine, ziprasidone, talnetant and osanetant.

Mood stabilisers which may be used in the therapy of the present invention include lithium, sodium valproate/valproic acid/divalproex, carbamazepine, lamotrigine, gabapentin, topiramate, oxcarbazepine and tiagabine.

Antidepressant drugs which may be used in the therapy of the present invention include serotonin antagonists, CRF-1 antagonists, Cox-2 inhibitor/SSRI dual antagonists; dopamine/noradrenaline/serotonin triple reuptake inhibitors; NK1 antagonists; NK1 and NK2 dual antagonists; NK1/SSRI dual antagonists; NK2 antagonists; serotonin agonists (such as rauwolscine, yohimbine and metoclopramide); serotonin reuptake inhibitors (such as citalopram, escitalopram, fluoxetine, fluvoxamine, femoxetine, indalpine, zimeldine, paroxetine and sertraline); dual serotonin/noradrenaline reuptake inhibitors (such as venlafaxine, reboxetine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); 5HT3 antagonists (such as example ondansetron and granisetron); and others (such as bupropion, amineptine, radafaxine, mianserin, mirtazapine, nefazodone and trazodone).

Anxiolytics which may be used in the therapy of the present invention include V1b antagonists, 5HT7 antagonists and benzodiazepines such as alprazolam and lorazepam.

Drugs for extrapyramidal side effects which may be used in the therapy of the present invention include anticholinergics (such as benztropine, biperiden, procyclidine and trihexyphenidyl), antihistamines (such as diphenhydramine) and dopaminergics (such as amantadine).

Cognitive enhancers which may be used in the therapy of the present invention include example cholinesterase inhibitors (such as tacrine, donepezil, rivastigmine and galantamine), H3 antagonists and muscarinic M1 agonists (such as cevimeline).

In one embodiment, the active ingredient for use in combination with a compound of the present invention, is an atypical antipsychotic, for example clozapine, olanzapine, risperidone, quetiapine, aripirazole, ziprasidone or amisulpride.

In one embodiment, the active ingredient for use in combination with a compound of the present invention is a typical antipsychotic, for example chlorpromazine, thioridazine, mesoridazine, fluphenazine, perphenazine, prochlorperazine, trifluoperazine, thiothixine, haloperidol, thiflurpromazine, pimozide, droperidol, chlorprothixene, molindone or loxapine.

In another embodiment, the active ingredient for use in combination with a compound of the present invention is a mood stabiliser, for example lithium, sodium valproate/valproic acid/divalproex, carbamazepine, lamotrigine, gabapentin, topiramate, oxcarbazepine or tiagabine.

In another embodiment, the active ingredient for use in combination with a compound of the present invention is an antidepressant, for example a serotonin agonist (such as rauwolscine, yohimbine or metoclopramide); a serotonin reuptake inhibitor (such as citalopram, escitalopram, fluoxetine, fluvoxamine, femoxetine, indalpine, zimeldine, paroxetine or sertraline); a dual serotonin/noradrenaline reuptake inhibitor (such as venlafaxine, reboxetine, duloxetine or milnacipran); a noradrenaline reuptake inhibitors (such as reboxetine); a tricyclic antidepressants (such as amitriptyline, clomipramine, imipramine, maprotiline, nortriptyline or trimipramine); a monoamine oxidase inhibitor (such as isocarboxazide, moclobemide, phenelzine or tranylcypromine); or other (such as bupropion, amineptine, radafaxine, mianserin, mirtazapine, nefazodone or trazodone).

In another embodiment, the active ingredient for use in combination with a compound of the present invention is an anxiolytic, for example a benzodiazepine such as alprazolam or lorazepam.

For use in medicine, the compounds of the present invention are usually administered as a standard pharmaceutical composition. The present invention therefore provides in a further aspect a pharmaceutical composition comprising a compound of formula (I) as hereinbefore described or a salt or solvate thereof and a pharmaceutically acceptable carrier. The pharmaceutical composition can be for use in the treatment of any of the conditions described herein.

The compounds of formula (I) may be administered by any convenient method, for example by oral, parenteral (e.g. intravenous), buccal, sublingual, nasal, rectal or transdermal administration and the pharmaceutical compositions adapted accordingly.

The compounds of formula (I) as hereinbefore described and their salts or solvates which are active when given orally can be formulated as liquids or solids, for example syrups, suspensions or emulsions, tablets, capsules and lozenges.

A liquid formulation will generally consist of a suspension or solution of the compound or salt or solvate in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or salt or solvate in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochloro-hydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches. The composition may be in unit dose form such as a tablet, capsule or ampoule.

Each dosage unit for oral administration contains, for example, from 1 to 250 mg (and for parenteral administration contains, for example, from 0.1 to 25 mg) of a compound of the formula (I) or a salt thereof calculated as the free base.

The compounds of the invention will normally be administered in a daily dosage regimen (for an adult patient) of, for example, an oral dose of between 1 mg and 500 mg, such as between 10 mg and 400 mg, e.g. between 10 and 250 mg or an intravenous, subcutaneous, or intramuscular dose of between 0.1 mg and 100 mg, such as between 0.1 mg and 50 mg, e.g. between 1 and 25 mg of the compound of the formula (I) or a salt thereof calculated as the free base, the compound being administered 1 to 4 times per day. Suitably the compounds will be administered for a period of continuous therapy, for example for a week or more.

The antipsychotic agent component or components used in the adjunctive therapy of the present invention may also be administered in their basic or acidic forms as appropriate or, where appropriate, in the form of a salt or other derivative. All solvates and all alternative physical forms of the antipsychotic agent or agents or their salts or derivatives as described herein, including but not limited to alternative crystalline forms, amorphous forms and polymorphs, are also within the scope of this invention. In the case of the antipsychotic agent or agents, the forms and derivatives are, for example, those which are approved for therapeutic administration as monotherapies, including those mentioned above, but all references to antipsychotic agents herein include all salts or other derivatives thereof, and all solvates and alternative physical forms thereof.

For adjunctive therapeutic administration according to the invention, compounds of formula (I) or salts or solvates and the antipsychotic agent or agents or their salts, derivatives or solvates may each be administered in pure form, but each of the components will, for example, be formulated into any suitable pharmaceutically acceptable and effective composition which provides effective levels of the respective component in the body. The choice of the most appropriate pharmaceutical compositions for each component is within the skill of the art, and may be the same form or different forms for each of the components. Suitable formulations include, but are not limited to tablets, capsules, powders, granules, lozenges, suppositories, reconstitutable powders, or liquid preparations such as oral or sterile parenteral solutions or suspensions.

For simultaneous administration as a combined composition of compounds of formula (I) and the antipsychotic agent or agents according to the invention, compounds of formula (I) or their salts or solvates and the antipsychotic agent or agents and their salts, derivatives or solvates may be administered together in pure form, but the combined components will, for example, be formulated into any suitable pharmaceutically acceptable and effective composition which provides effective levels of each of the components in the body. The choice of the most appropriate pharmaceutical compositions for the combined components is within the skill of the art. Suitable formulations include, but are not limited to tablets, sub-lingual tablets, buccal compositions, capsules, powders, granules, lozenges, suppositories, reconstitutable powders, or liquid preparations such as oral or sterile parenteral solutions or suspensions.

In order to obtain consistency of adjunctive administration, the compositions of each of the components, or of the combination of the components is, for example, in the form of a unit dose.

The term "treatment" includes prophylaxis, where this is appropriate for the relevant condition(s).

Biological Test Methods

FLIPR Experiments on $M_1$ Receptor to Determine Agonist/Antagonist Potency

Compounds of the invention were characterized in a functional assay to determine their ability to activate the intracellular calcium pathway in CHO cells with stable expression of human muscarinic receptors using FLIPR (Fluorometric Imaging Plate Reader) technology. Briefly, CHO-M1 cells were plated (20,000/well) and allowed to grow overnight at 37 degrees. Media was removed and 30 uL loading buffer containing FLIPR Calcium 3 dye (Molecular Devices Co., Sunnyvale, Calif.) was added according to manufacturer's instructions. After incubation at 37 degrees for 45-60 minutes, 10 uL of the assay buffer containing test compounds was added to each well on FLIPR instrument. Calcium response was monitored to determine agonism. Plates were then incubated for another 10-15 minutes before 10 uL of assay buffer containing acetylcholine was added as the agonist challenge. Calcium response was then monitored again to determine compound's antagonism to acetylcholine. Concentration-response curves of both agonism and antagonism on M1 receptors were performed for each compound. Results were imported into ActivityBase data analysis suite (ID Business Solution Inc., Parsippany, N.J.) where the curves were analysed by non-linear curve fitting and the resulting pEC50/pIC50 were calculated.

FLIPR Experiments on $M_1$ Receptor to Determine Agonist Intrinsic Activity

To determine the intrinsic activities of M1 agonist compounds, compounds of the invention were characterized in FLIPR experiments on U2OS cells with transient expression of human muscarinic M1 receptors. Briefly, U2OS cells were transduced with M1 BacMam virus (#) in $2 \times 10e^5$/mL cell suspension with 0.1% virus/cell ratio (v/v). The virus to cell ratio was determined in separate experiments by functional titration to be most appropriate to measure intrinsic activities of partial agonists. After mixing with virus in suspension, cells were then plated (10,000/well) and allowed to grow overnight at 37 degrees. FLIPR experiment was then carried out next day using the same protocol as described above for CHO-M1 cells. Results were imported into ActivityBase data analysis suite where the curves were analysed by non-linear curve fitting and the resulting pEC50 values were calculated. The intrinsic activities of agonist compounds were calculated as percentage of maximum FLIPR response induced by acetylcholine added as control on the same compound plates, and converted to a fraction between 0 and 1.

: Ames, R S; Fornwald, J A; Nuthulaganti, P; Trill, J J; Foley, J J; Buckley, P T; Kost, T A; Wu, Z and Romanos, M A. (2004) Use of BacMam recombinant baculoviruses to support G protein-coupled receptor drug discovery. Receptors and Channels 10 (3-4): 99-109

The exemplified compounds have a $pEC_{50}$ value of >6.0 at the muscarinic $M_1$ receptor, and intrinsic activity >0.5.

FLIPR Experiments on $M_{2-5}$ Receptor to Determine Receptor Subtype Selectivity To determine selectivity of compounds of the invention against other muscarinic receptor subtypes, compounds were characterized in FLIPR experiments in CHO cells with stable expression of human muscarinic receptors, M2, M3, M4 or M5. In the case of M2 and M4 receptors, chimeric G-protein Gqi5 was also co-expressed to couple receptors to the calcium signaling pathway. Briefly, cells were plated (20,000/well) and allowed to grow overnight at 37 degrees. FLIPR experiment was then carried out next day using the same protocol as described above for CHO-M1 cells. Results were imported into ActivityBase data analysis suite where the curves were analysed by non-linear curve fitting and the resulting pEC50/pIC50 values were calculated.

The exemplified compounds are selective for the M1 receptor over M2, M3, M4 and M5 receptors, with typical selectivity (ratio of pEC50's) of ≧10-fold, and in certain cases ≧100-fold.

The invention is further illustrated by the following non-limiting examples.

MDAP refers to mass-directed automated purification using reverse phase chromatography on $C_{18}$ stationary phase eluted with acetonitrile/water/0.1% formic acid.

SCX refers to a sulfonic acid ion exchange resin supplied by Varian.

All reactions were either done under argon or can be done under argon, unless stated otherwise (for example hydrogenation reactions).

DESCRIPTION 1

1-Chloro-2,5-difluoro-4-nitrobenzene (D1)

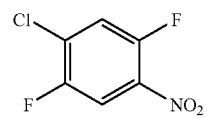

2-Chloro-1,4-difluorobenzene (1.34 mmol, 200 mg) was dissolved in concentrated sulphuric acid (1.7 ml) and cooled to 0° C.; $KNO_3$ (1 eq., 1.34 mmol, 135 mg) was added in one lot and the mixture was stirred at 0° C. for 1 hour and at room temperature for 2 hours. The crude mixture was poured onto ice and extracted with ethyl acetate (2×); the organics were combined dried over $Na_2SO_4$, filtered and the solvent was evaporated to afford the title compound which was purified by chromatography (EtOAc n-hexane) to afford the title product, 228 mg, 88%, volatile oil under high vacuum.

$^1$HNMR δ(DMSO, 400 MHz) 8.168 (1H, dd), 8.404 (1H, dd).

DESCRIPTION 2

1,1-Dimethylethyl 4-[(5-chloro-4-fluoro-2-nitrophenyl)amino]-piperidinecarboxylate (D2)

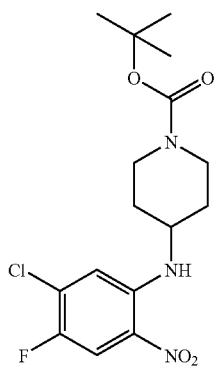

1-Chloro-2,5-difluoro-4-nitrobenzene (D1) (1.18 mmol, 228 mg) was dissolved in dry dimethylformamide (2 ml) and diisopropylethylamine (1 eq., 1.18 mmol, 0.209 ml), 1,1-dimethylethyl 4-amino-1-piperidinecarboxylate (1 eq., 1.18 mmol, 236 mg) were added at room temperature and the mixture was stirred at 50° C. overnight. The crude mixture was then cooled to room temperature and water (150 ml) was added; the aqueous solution was extracted with ethyl acetate (2×); organics were alternatively washed with brine and water (2×). The organics were combined dried over $Na_2SO_4$, filtered and the solvent was evaporated to afford the title compound, 340 mg, 80%, bright orange solid, $M^+–H=372$.

DESCRIPTION 3

1,1-Dimethylethyl 4-[(2-amino-5-chloro-4-fluorophenyl)amino]-1-piperidinecarboxylate (D3)

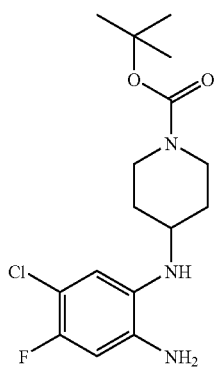

1,1-Dimethylethyl 4-[(5-chloro-4-fluoro-2-nitrophenyl)amino]-piperidinecarboxylate (D2) (0.91 mmol, 340 mg) was dissolved in ethanol (20 ml) and an aqueous suspension of Raney-Nickel (1 ml) was added at room temperature; the mixture was heated to 40° C. and hydrazine monohydrate (15 eq., 13.7 mmol, 0.424 ml) was added over 20 min at 40° C. The reaction mixture was then cooled to room temperature, filtered through celite and the solvent was evaporated to yield the title compound, which was purified by chromatography, complete conversion, 312 mg, $M^+–H=342$.

DESCRIPTION 4

1,1-Dimethylethyl 4-(6-chloro-5-fluoro-2-oxo-2,3-dihydro-1H-benzimidazol-1-yl)-1-piperidinecarboxylate (D4)

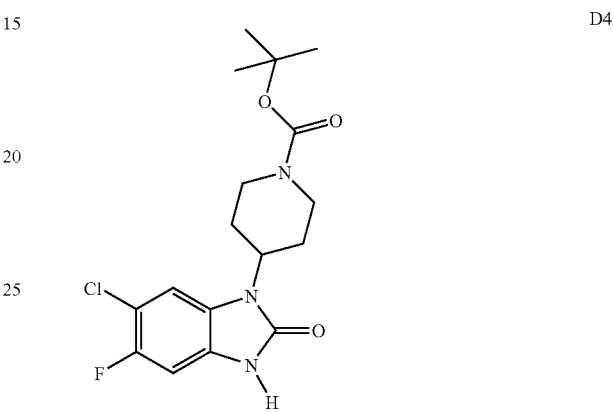

1,1-Dimethylethyl 4-[(2-amino-5-chloro-4-fluorophenyl)amino]-1-piperidinecarboxylate (D3) (0.87 mmol, 300 mg) was dissolved in 5 ml of tetrahydrofuran and carbonyldiimidazole (1,1'-(oxomethanediyl)bis-1H-imidazole) (3 eq., 2.6 mmol, 440 mg) was added at room temperature; the mixture was refluxed at 50° C. overnight. The mixture was cooled to room temperature, THF evaporated and it was diluted in ethyl acetate/$H_2O$/$NaHCO_3$ (saturated solution); the two layers were separated and the aqueous phase was extracted with ethyl acetate (2×); the organic phases were combined and washed with water and $NaHCO_3$ (saturated solution), they were dried over $Na_2SO_4$, filtered and the solvent was evaporated to afford the crude compound that was purified by chromatography (methanol-$NH_3$-dichloromethane) to yield the title compound, 170 mg 53%, $M^+–H=368$.

DESCRIPTION 5

6-Chloro-5-fluoro-1-(4-piperidinyl)-1,3-dihydro-2H-benzimidazol-2-one hydrochloride (D5)

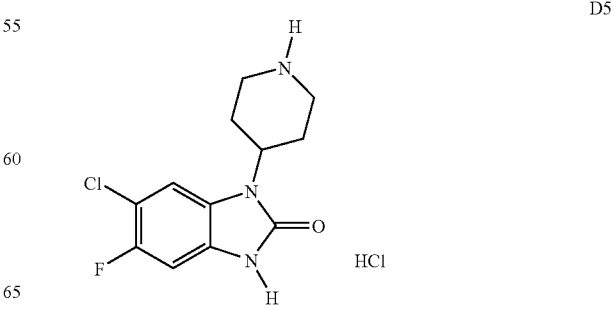

1,1-Dimethylethyl 4-(6-chloro-5-fluoro-2-oxo-2,3-dihydro-1H-benzimidazol-1-yl)-1-piperidinecarboxylate (D4) (0.460 mmol, 170 mg) was dissolved in dichloromethane-diethyl ether, and HCl (5 ml of a 4M solution in 1,4-dioxane) was added at room temperature; the mixture was shaken at room temperature overnight. Solvent was evaporated to afford the title compound, mono hydrochloride salt, complete conversion, $M^++H=270$.

DESCRIPTION 6

1,1-Dimethylethyl 4-[(5-chloro-4-methyl-2-nitrophenyl)amino]-1-piperidinecarboxylate (D6)

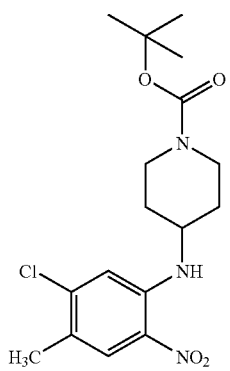

D6

1,5-Dichloro-2-methyl-4-nitrobenzene (2.42 mmol, 500 mg) was dissolved in dry dimethylformamide (5 ml) and diisopropylethylamine (1 eq., 2.42 mmol, 0.413 ml), 1,1-dimethylethyl 4-amino-1-piperidinecarboxylate (1 eq., 2.42 mmol, 484 mg) were added at room temperature and the mixture was stirred at 100° C. overnight. The crude mixture was then cooled to room temperature and water was added; the aqueous solution was extracted with ethyl acetate (3×); organics were alternatively washed with brine and water. The organics were combined, dried over $Na_2SO_4$, filtered and the solvent was evaporated to afford the crude compound that was purified by chromatography (ethyl acetate/hexane) to yield the title compound, 98 mg, 11%, bright orange solid.

$^1$HNMR δ (DMSO, 400 MHz) 1.407 (11H, s), 1.945 (2H, dd broad), 2.243 (3H, s), 2.950 (2H, s broad), 3.888 (3H, d broad), 7.291 (1H, s), 7.810 (1H, d), 8.071 (1H, s).

DESCRIPTION 7

1,1-Dimethylethyl 4-[(2-amino-5-chloro-4-methylphenyl)amino]-1-piperidinecarboxylate (D7)

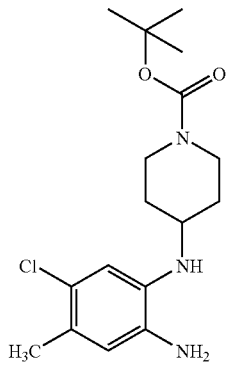

D7

1,1-Dimethylethyl 4-[(5-chloro-4-methyl-2-nitrophenyl)amino]-1-piperidinecarboxylate (D6) (0.270 mmol, 100 mg) was dissolved in ethanol (10 ml) and an aqueous suspension of Raney-Nickel (0.3 ml) was added at room temperature; the mixture was heated to 40-50° C. and hydrazine monohydrate (15 eq., 4 mmol, 0.14 ml) was added over 20-30 min; the reaction mixture was then heated at 40° C. for 10 extra minutes and then it was then cooled to room temperature, filtered through celite and the solvent was evaporated to yield the crude product. Crude product was subsequently purified by chromatography (ethyl acetate/hexane) to yield the title compound, 80 mg, 88%, $M^+$–Boc=240.

DESCRIPTION 8

1,1-Dimethylethyl 4-(6-chloro-5-methyl-2-oxo-2,3-dihydro-1H-benzimidazol-1-yl)-1-piperidinecarboxylate (D8)

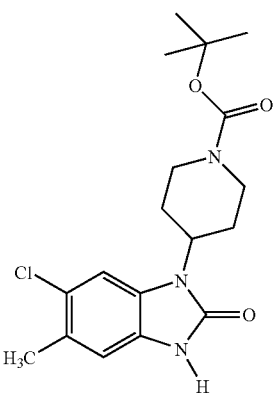

D8

1,1-Dimethylethyl 4-[(2-amino-5-chloro-4-methylphenyl)amino]-1-piperidinecarboxylate (D7) (0.292 mmol, 100 mg) was dissolved in 10 ml of dichloromethane and a 20% solution in toluene of phosgene (1.05 eq., 150 microliters) followed by triethylamine (2.1 eq., 85 microliters) were added at 0° C.; the reaction mixture was then stirred at 0° C. for 30 minutes and subsequently quenched with citric acid (10% aqueous solution). The reaction mixture was diluted with dichloromethane, the two phases were separated and the aqueous phase was extracted with dichloromethane (1×); the organic phases were combined, dried over $Na_2SO_4$, filtered and the solvent was evaporated to afford the crude compound that was purified by chromatography (ethyl acetate-hexane) to yield the title compound, 50 mg, 50%, $M^+$–H=364.

DESCRIPTION 9

6-Chloro-5-methyl-1-(4-piperidinyl)-1,3-dihydro-2H-benzimidazol-2-one hydrochloride (D9)

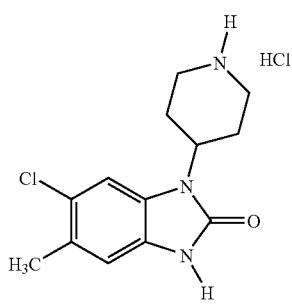

1,1-Dimethylethyl 4-(6-chloro-5-methyl-2-oxo-2,3-dihydro-1H-benzimidazol-1-yl)-1-piperidinecarboxylate (D8) (0.270 mmol, 100 mg) was treated with 8 ml of HCl (4M solution in 1,4-dioxane) at room temperature; the mixture was stirred at room temperature for 5 hours. Solvent was evaporated to afford the title compound, mono hydrochloride salt, 60 mg, 90%, $M^++H=266$.

DESCRIPTION 10

5-Chloro-2-iodo-4-(trifluoromethyl)aniline (D10)

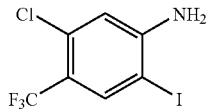

Iodine monochloride (1.5 g) was added in one portion to a mixture of 3-chloro-4-trifluoromethylaniline (1.7 g), sodium acetate trihydrate (2.2 g), and acetic acid (10 ml) at room temperature. After 30 min aqueous sodium bicarbonate/sodium sulfite was added and the mixture extracted with diethyl ether. The organic phase was dried over $Na_2SO_4$, filtered and evaporated. The residue was purified by chromatography (ethyl acetate-hexane) to afford the title compound, 2.2 g.

DESCRIPTION 11

1,1-Dimethylethyl 4-[({[5-chloro-2-iodo-4-(trifluoromethyl)phenyl]amino}carbonyl)amino]-1-piperidinecarboxylate (D11)

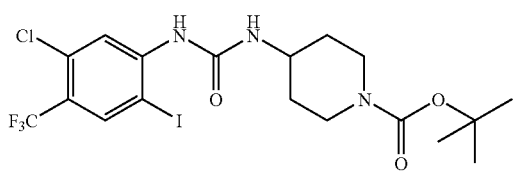

5-Chloro-2-iodo-4-(trifluoromethyl)aniline D10 (7.7 mmol, 2.2 g), bis(trichloromethyl) carbonate (0.35 eq., 2.7 mmol, 800 mg) were dissolved in 1,4-dioxane (10 ml) and the mixture was heated to 100° C. for 15 minutes; the mixture was then cooled to room temperature and it was filtered. The filtrate was concentrated to afford 1-chloro-4-iodo-5-isocyanato-2-(trifluoromethyl)benzene which was dissolved in dichloromethane (10 ml) and 1,1-dimethylethyl 4-amino-1-piperidinecarboxylate (2 eq., 11.4 mmol, 2.28 g) was added at room temperature; the mixture was stirred at room temperature for 1.5 hours. Solvent was subsequently evaporated and the crude obtained was purified by chromatography (ethyl acetate-n-hexane) to afford the title compound, 1.46 g, 46%, $M^+-H=546$.

DESCRIPTION 12

1,1-Dimethylethyl 4-[5-chloro-2-oxo-6-(trifluoromethyl)-2,3-dihydro-1H-benzimidazol-1-yl]-1-piperidinecarboxylate (D12)

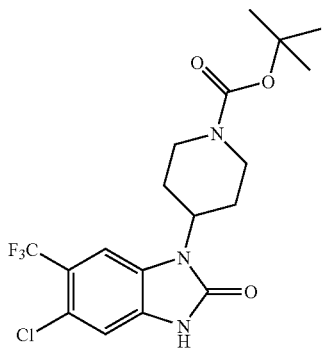

Under an argon atmosphere, dry 1,4-dioxane (5 ml), palladium 1,1'-bis(diphenyl-phosphino)ferrocene dichloride (10% mol, 0.268 mmol, 220 mg), $Na^tBuO$ (2 eq., 5.36 mmol, 520 mg) were mixed together and sonicated at room temperature for 10 minutes; 1,1-dimethylethyl 4-[({[5-chloro-2-iodo-4-(trifluoromethyl)phenyl]amino}carbonyl)amino]-1-piperidinecarboxylate D11 (2.68 mmol, 1.5 g) was then added at room temperature and the mixture was heated to 80° C. overnight. The reaction mixture was cooled to room temperature, quenched with $NH_4Cl$ (saturated solution) and the aqueous solution obtained was extracted with ethyl acetate; the organics were combined, dried over $Na_2SO_4$, filtered and the solvent was evaporated to afford the crude compound that was purified by chromatography (methanol-$NH_3$-dichloromethane) to yield the title compound, 115 mg, 10%, $M^+-H=418$.

DESCRIPTION 13

5-Chloro-1-(4-piperidinyl)-6-(trifluoromethyl)-1,3-dihydro-2H-benzimidazol-2-one hydrochloride (D13)

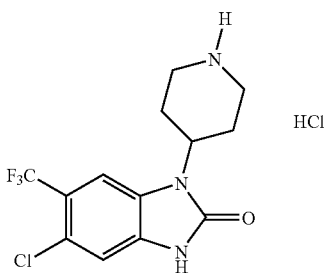

1,1-Dimethylethyl 4-[5-chloro-2-oxo-6-(trifluoromethyl)-2,3-dihydro-1H-benzimidazol-1-yl]-1-piperidinecarboxylate D12 (0.27 mmol, 115 mg) was treated with HCl (315 microliters of a 4M solution in 1,4-dioxane) at room temperature; the mixture was stirred at room temperature for 2.5 hours. Solvent was evaporated to afford the title compound, mono hydrochloride salt, 82 mg, 96%, M⁺+H=320.

DESCRIPTION 14

4-Fluoro-2-methylphenyl methyl carbonate (D14)

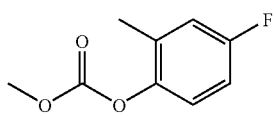

4-Fluoro-2-methylphenol (4 mmol, 504 mg) in tetrahydrofuran (10 mL) under argon was treated at 0 ° C. with pyridine (8.8 mmol, 700 mg, 2.2 eq) then methyl chloroformate (4.4 mmol, 415 mg, 1.1 eq). The mixture was allowed to warm to room temperature and to stir for 45 min. It was then concentrated and dissolved in dichloromethane (10 mL), and pyridine (8.8 mmol, 700 mg, 2.2 q) then methyl chloroformate (4.4 mmol, 415 mg, 1.1 eq) were added again and allowed to react for 30 min. Then dioxane (3 mL) was added to help solubility, then pyridine (8.8 mmol, 700 mg, 2.2 eq) and methyl chloroformate (4.4 mmol, 415 mg, 1.1 eq) again 3 times. LC/MS actually showed evolution in conversion of start material after every add, but also that reaction stopped 5 min later. Achieved conversion was 85% (UV). The mixture was concentrated under reduced pressure, dissolved in dichloromethane, washed with 1M HCl aqueous solution then 10% $Na_2CO_3$ aqueous solution. Organics were dried on $MgSO_4$ and concentrated under reduced pressure to give the title compound as an oil (2.5 mmol, 468 mg, 64% yield). M+H 185.08.

DESCRIPTION 15

4-Fluoro-2-methyl-5-nitrophenyl methyl carbonate (D15)

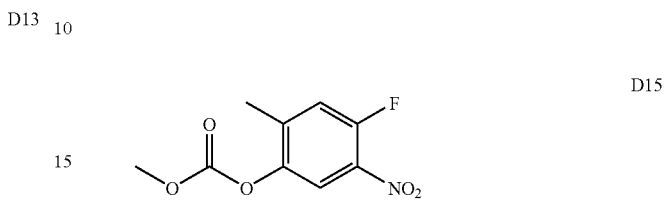

4-Fluoro-2-methylphenyl methyl carbonate (D14) (2.5 mmol, 468 mg) was dissolved in concentrated sulphuric acid under argon and cooled to 0° C. $KNO_3$ (2.5 mmol, 253 mg, 1 eq) was then added cautiously while keeping the temperature around 0° C. The mixture was then allowed to stir for 2 h while warming up to room temperature, then it was poured onto ice cautiously and extracted with ether twice. Organics were combined, dried on $MgSO_4$ and concentrated under reduced pressure to give the title compound as a light brown solid (2.36 mmol, 540 mg, 94% yield). $^1$H NMR δ($CDCl_3$) 7.92 (1H, d), 7.18 (1H, d), 3.95 (3H, s), 2.33 (3H, s).

DESCRIPTION 16

4-Fluoro-2-methyl-5-nitrophenol (D16)

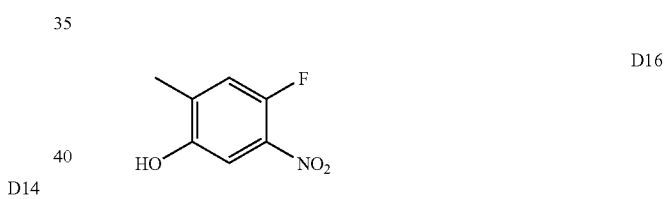

4-Fluoro-2-methyl-5-nitrophenyl methyl carbonate (D15) (2.36 mmol, 540 mg) was treated under argon with 6 mL of a 2M solution of ammonia in methanol (12 mmol $NH_3$, 5 eq) and was allowed to stir for 1.5 h. The mixture was concentrated under reduced pressure and purified by chromatography (0-25% ethyl acetate/petrol ether) to give the title compound as bright yellow solid (1.7 mmol, 290 mg, 72% yield). M−H=170.12, Rt 2.34 min, $^1$H NMR δ ($CDCl_3$) 7.48 (1H, d), 7.06 (1H, d), 5.15 (1H, s), 2.32 (3H, s).

DESCRIPTION 17

1-Fluoro-5-methyl-4-methoxy-2-nitrobenzene (D17)

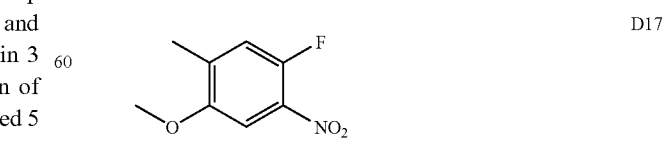

4-Fluoro-2-methyl-5-nitrophenol (D16) (0.85 mmol, 145 mg) in dimethylformamide (5 mL) under argon was treated with $K_2CO_3$ (0.85 mmol, 117 mg, 1 eq) then methyl iodide (1.7 mmol, 242 mg, 2 eq). The mixture was allowed to stir at room temperature for 1.5 h, concentrated under reduced pressure, treated with 10% $Na_2CO_3$ aqueous solution and extracted 3 times with ethyl acetate. Organics were combined, dried on $MgSO_4$ and concentrated under reduced pressure to give the title compound as a bright yellow solid (0.79 mmol, 146 mg, 93% yield). Rt=2.84 min.

DESCRIPTION 18

1,1-Dimethylethyl 4-{[5-methyl-4-methoxy-2-nitrophenyl]amino}-1-piperidinecarboxylate (D18)

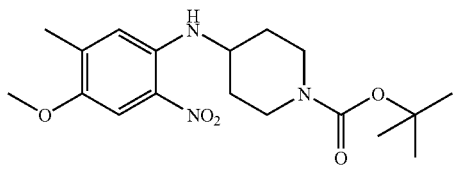

D18

1-Fluoro-5-methyl-4-methoxy-2-nitrobenzene (D17) (0.79 mmol, 146 mg) was treated under argon at room temperature with 1,1-dimethylethyl 4-amino-1-piperidinecarboxylate (0.8 mmol, 160 mg, 1 eq) and diisopropylethylamine (0.8 mmol, 103 mg, 1 eq) then stirred at 75° C. overnight. Completion was not observed, and the mixture was heated at higher temperature, 1,1-dimethylethyl 4-amino-1-piperidinecarboxylate (0.8 mmol, 160 mg, 1 eq) and diisopropylethylamine (0.8 mmol, 103 mg, 1 eq) were added again and allowed to react overnight at 100° C. The mixture was concentrated under reduced pressure, treated with 10% $Na_2CO_3$ aqueous solution and extracted twice with ether. Organics were combined, dried on $MgSO_4$, concentrated under reduced pressure and chromatographed (0-50% ethyl acetate/petrol ether) to give the title compound as an orange residue (0.33 mmol, 120 mg, 42% yield). M+H=310.1, main fragment (molecule has lost its tert-butyl group).

DESCRIPTION 19

1,1-Dimethylethyl 4-{[2-amino-5-methyl-4-methoxy-phenyl]amino}-1-piperidinecarboxylate (D19)

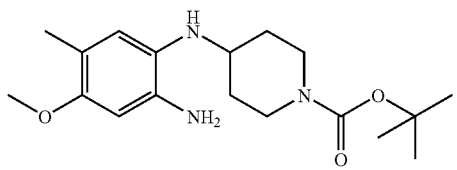

D19

The title compound was prepared from D18 in a similar manner as 1,1-dimethylethyl 4-[(2-amino-4-fluoro-5-methylphenyl)amino]-1-piperidinecarboxylate (D28), and 0.32 mmol (108 mg) of product was obtained, with 97% yield. M+H=336.18.

DESCRIPTION 20

1,1-Dimethylethyl 4-[6-methyl-5-methoxy-2-oxo-2,3-dihydro-1H-benzimidazol-1-yl]-1-piperidinecarboxylate (D20)

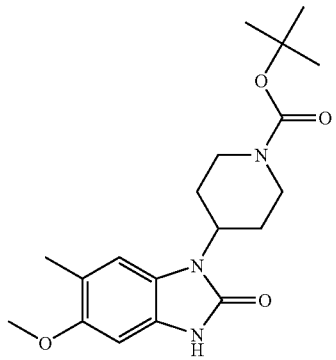

D20

The title compound was prepared from D19 in a similar manner as 1,1-dimethylethyl 4-(5-fluoro-6-methyl-2-oxo-2,3-dihydro-1H-benzimidazol-1-yl)-1-piperidine-carboxylate (D29), and 0.39 mmol (140 mg) of product was obtained. M−H=360.3.

DESCRIPTION 21

6-Methyl-5-methoxy-1-(4-piperidinyl)-1,3-dihydro-2H-benzimidazol-2-one (D21)

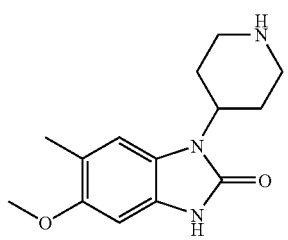

D21

The title compound was prepared from D20 in a similar manner as 5-fluoro-6-methyl-1-(4-piperidinyl)-1,3-dihydro-2H-benzimidazol-2-one (D30), and 0.35 mmol (92 mg) of product was obtained with 90% yield. M+H=262.04.

DESCRIPTION 22

1-Chloro-4-fluoro-2-methyl-5-nitrobenzene (D22)

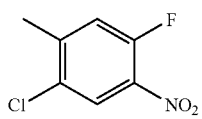

D22

1-Chloro-4-fluoro-2-methylbenzene (10 mmol, 1.44 g) was dissolved in concentrated sulphuric acid under argon and cooled to 0° C. KNO$_3$ (10 mmol, 1.01 g, 1 eq) was then added cautiously while keeping the temperature around 0° C. The mixture was then allowed to stir for 2 h while warming up to room temperature, then it was poured onto ice cautiously and extracted with ether twice. Organics were combined, dried on MgSO$_4$ and concentrated under reduced pressure to give an oil (9.1 mmol, 1.73 g, 91% yield), which was chromatographed (0-25% ethyl acetate/petrol ether) to give the title compound as a transparent oil (7 mmol, 1.3 g, 70% total yield). $^1$H NMR δ (CDCl$_3$) 8.09 (1H, d), 7.19 (1H, d), 2.46 (3H, s).

DESCRIPTION 23

1,1-Dimethylethyl 4-[(4-chloro-5-methyl-2-nitrophenyl)amino]-1-piperidine-carboxylate (D23)

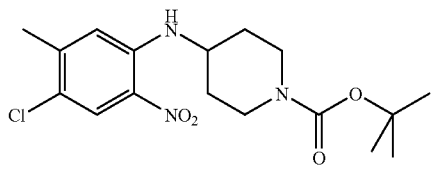

1-Chloro-4-fluoro-2-methyl-5-nitrobenzene (D22) (1.5 mmol, 284 mg) in dimethylformamide (5 mL) was treated under argon at room temperature with 1,1-dimethylethyl 4-amino-1-piperidinecarboxylate (1.5 mmol, 300.5 mg, 1 eq) and diisopropylethylamine (1.5 mmol, 194 mg, 1 eq) then stirred at 75° C. overnight. The mixture was concentrated under reduced pressure, treated with 10% Na$_2$CO$_3$ aqueous solution and extracted twice with ether. Organics were combined, dried on MgSO$_4$ and concentrated under reduced pressure to give the title compound as a clean orange solid (1.46 mmol, 539 mg, 97% yield). M−H=368.16.

DESCRIPTION 24

1,1-Dimethylethyl 4-[(2-amino-4-chloro-5-methylphenyl)amino]-1-piperidinecarboxylate (D24)

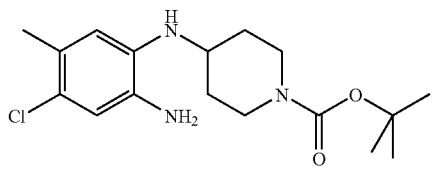

The title compound was prepared from (D23) in a similar manner as 1,1-dimethylethyl 4-[(2-amino-4-fluoro-5-methylphenyl)amino]-1-piperidinecarboxylate (D28), and 1.43 mmol (484 mg) of product was obtained, with 98% yield. M+H=340.14.

DESCRIPTION 25

1,1-Dimethylethyl 4-(5-chloro-6-methyl-2-oxo-2,3-dihydro-1H-benzimidazol-1-yl)-1-piperidine-carboxylate (D25)

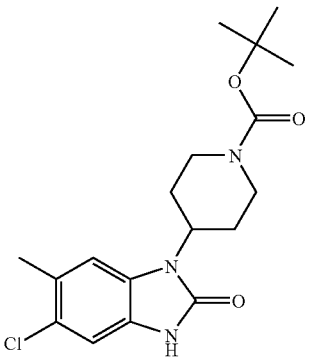

The title compound was prepared from D24 in a similar manner as 1,1-dimethylethyl 4-(5-fluoro-6-methyl-2-oxo-2,3-dihydro-1H-benzimidazol-1-yl)-1-piperidine-carboxylate (D29), and 0.89 mmol (324 mg) of product was obtained, with 62% yield. M−H=364.3

DESCRIPTION 26

5-Chloro-6-methyl-1-(4-piperidinyl)-1,3-dihydro-2H-benzimidazol-2-one (D26)

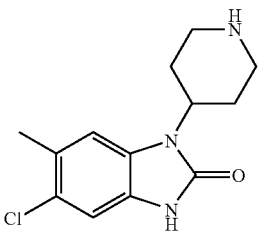

The title compound was prepared from D25 in a similar manner as 5-fluoro-6-methyl-1-(4-piperidinyl)-1,3-dihydro-2H-benzimidazol-2-one (D30), and 0.98 mmol (260 mg) of product was obtained, with 100% yield. M+H=266.2.

DESCRIPTION 27

1,1-Dimethylethyl 4-[(4-fluoro-5-methyl-2-nitrophenyl)amino]-1-piperidine-carboxylate (D27)

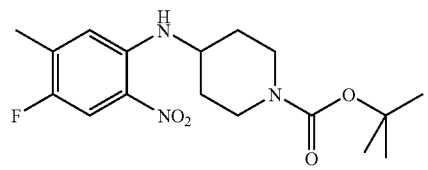

1,4-Difluoro-2-methyl-5-nitrobenzene (1.5 mol, 260 mg) in dimethylformamide (10 mL) was treated under argon at room temperature with 1,1-dimethylethyl 4-amino-1-piperidinecarboxylate (1.5 mmol, 300.5 mg, 1 eq) and diisopropylethylamine (1.5 mmol, 260 μL, 1 eq) then stirred at 70 (→80) °C. for 38 h. The mixture was concentrated under vacuum, treated with water and extracted twice with ether. Organics were combined, dried on MgSO₄ and concentrated under vacuum to give a red-brown residue which was chromatographed (0-25% ethyl acetate/petrol ether 6 CV) to give the title compound as a red solid (0.96 mmol, 340 mg, 64% yield). M+H=298.07, main fragment (molecule has lost its tert-butyl group).

DESCRIPTION 28

1,1-Dimethylethyl 4-[(2-amino-4-fluoro-5-methylphenyl)amino]-1-piperidinecarboxylate (D28)

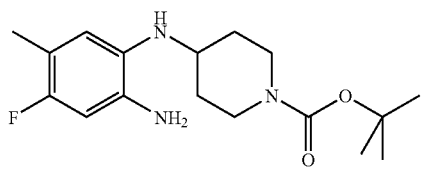

1,1-Dimethylethyl 4-[(4-fluoro-5-methyl-2-nitrophenyl)amino]-1-piperidinecarboxylate (D27) (0.96 mmol, 340 mg) in ethanol (20 mL) was treated under argon at room temperature with Raney Nickel (suspension, 50% in water, 0.5 mL) then dropwise with hydrazine hydrate (9.6 mmol, 10 eq) in ethanol over 15 min. The mixture was heated at 45° C. for 50 min. The Raney nickel was filtered off and washed with ethanol. The reaction mixture was concentrated under vacuum to give the title compound (0.88 mmol, 284 mg, 92% yield). M+H=324.16.

DESCRIPTION 29

1,1-Dimethylethyl 4-(5-fluoro-6-methyl-2-oxo-2,3-dihydro-1H-benzimidazol-1-yl)-1-piperidine-carboxylate (D29)

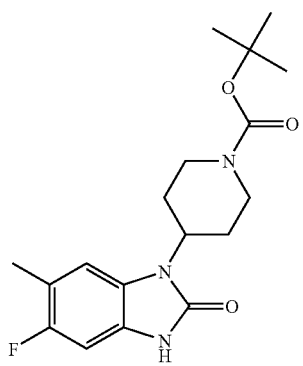

1,1-Dimethylethyl 4-[(2-amino-4-fluoro-5-methylphenyl)amino]-1-piperidinecarboxylate (D28) (0.88 mmol, 284 mg) in tetrahydrofuran (30 mL) was treated with N,N'-carbonyldiimidazole (0.88 mmol, 141 mg, 1 eq) under argon at room temperature and was stirred at room temperature overnight. The reaction mixture was then concentrated under vacuum and the residue dissolved in THF (5 ml) and stirred for 3 h then heated at 45° C. for 45 min, then N,N'-carbonyldiimidazole (0.44 mmol, 70 mg, 0.5 eq) was added and allowed to react for 40 min. The mixture was concentrated, partitioned between 10% Na₂CO₃ aqueous solution and ethyl acetate. Organics were dried on MgSO₄, concentrated and chromatographed (EtOAc/pet ether) to give the title compound (0.68 mmol, 239 mg, 77% yield). M−H=348.3.

DESCRIPTION 30

5-Fluoro-6-methyl-1-(4-piperidinyl)-1,3-dihydro-2H-benzimidazol-2-one (D30)

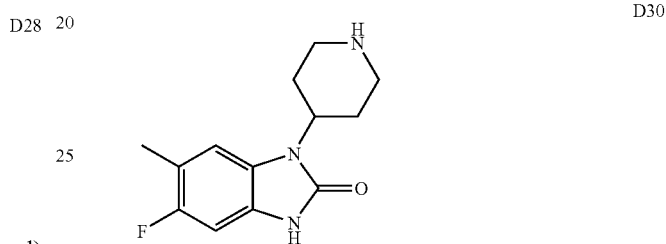

1,1-Dimethylethyl 4-(5-fluoro-6-methyl-2-oxo-2,3-dihydro-1H-benzimidazol-1-yl)-1-piperidine-carboxylate (D29) (0.68 mmol, 239 mg) in dichloromethane (5 mL) was treated under argon at room temperature with trifluoroacetic acid (1 mL) and allowed to stir for 1 h. The mixture was concentrated, treated with 10% Na₂CO₃ aqueous solution, extracted 3 times with ethyl acetate. Organics were combined, dried on MgSO₄, and concentrated under vacuum to give the title compound (0.64 mmol, 160 mg, 94% yield). M+H=250.2.

DESCRIPTION 31

5,6-Dimethyl-1-[1-(phenylmethyl)-1,2,3,6-tetrahydro-4-pyridinyl]-1,3-dihydro-2H-benzimidazol-2-one (D31)

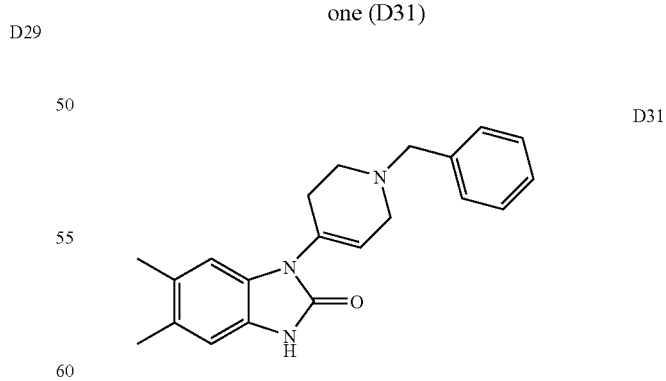

4,5-Dimethyl-1,2-benzenediamine (3 mmol, 408.6 mg) and ethyl 4-oxo-1-(phenylmethyl)-3-piperidinecarboxylate (3 mmol, 784 mg, 1 eq) were dissolved in xylene (20 mL) and heated under argon under reflux for 8 h and stood at room temperature overnight. The mixture was concentrated under reduced pressure, and the residue was recrystallised in ethyl acetate containing a trace of methanol to give the title compound as white crystals (1.39 mmol, 463 mg, 46% yield). M+H=334.3.

DESCRIPTION 32

5,6-Dimethyl-1-(4-piperidinyl)-1,3-dihydro-2H-benzimidazol-2-one—salt with acetic acid (D32)

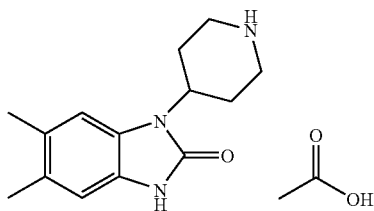

5,6-Dimethyl-1-[1-(phenylmethyl)-1,2,3,6-tetrahydro-4-pyridinyl]-1,3-dihydro-2H-benzimidazol-2-one (D31) (0.6 mmol, 200 mg) was dissolved in ethanol (10 mL) and acetic acid (2 mL), then Pd/charcoal (50 mg) was added under argon and the mixture was stirred under 50 PSI of hydrogen for 24 h at room temperature. The catalyst was filtered off and the filtrate was concentrated under reduced pressure to give title compound as the acetate salt (330 mg).

DESCRIPTION 33

1-Bromo-4-fluoro-2-methyl-5-nitrobenzene (D33)

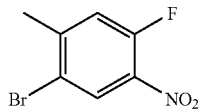

1-Bromo-4-fluoro-2-methylbenzene (10 mmol, 1.89 g) was dissolved in concentrated $H_2SO_4$ (sp. gr 1.18) (10 mL) under argon and the mixture cooled to 0° C. $KNO_3$ (10 mmol, 1.01 g) was added portion wise, maintaining the temperature around 0° C. The mixture was then allowed to stir at between 0° C. and 20° C. for 2 h. The reaction mixture was poured into ice and the product extracted with ether (×2). The organic layers were combined, dried ($MgSO_4$) and the solvent removed under reduced pressure to yield the product as an oil (9.4 mmol, 2.2 g, 94%)

$^1$H NMR: 400 MHz; $CDCl_3$: δ 3.5 (1H, s, 2-$CH_3$); 10.7 (1H, d, J=12 Hz, 3-H); 11.75 (2H, d, J=9 Hz, 6-H).

DESCRIPTION 34

1,1-Dimethylethyl-4-[(4-bromo-5-methyl-2-nitrophenyl)amino]-1-piperidinecarboxylate (D34)

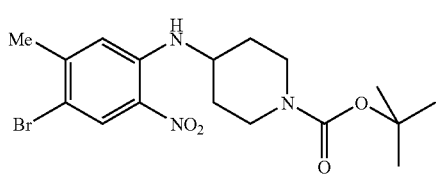

A solution of 1-bromo-4-fluoro-2-methyl-5-nitrobenzene (D33) (3 mmol, 702 mg) in dry dimethylformamide (20 mL) was treated with 1-Boc-4-piperidinamine (3 mmol, 601 mg, 1 eq) and diisopropylethylamine (3 mmol, 520 μL, 1 eq), and the mixture stirred under argon and heated to 80° C. for 17 h. The reaction mixture was concentrated under reduced pressure, water added and the product extracted using ethyl acetate (×2). The organic layers were combined, dried ($MgSO_4$) and the solvent removed under reduced pressure to afford the product as an orange solid (2.3 mmol, 0.95 g, 77%). $MH^+$=360.1.

DESCRIPTION 35

1,1-Dimethylethyl-4-[(2-amino-4-bromo-5-methylphenyl)amino]-1-piperidinecarboxylate (D35)

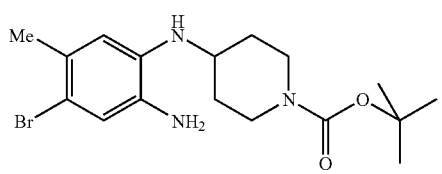

1,1-Dimethylethyl-4-[(4-bromo-5-methyl-2-nitrophenyl)amino]-1-piperidinecarboxylate (D34) (2.3 mmol, 0.95 g) was dissolved in ethanol (40 mL) and Raney Nickel (50% aqueous suspension, 5 mL) was added. A solution of hydrazine hydrate (23 mmol, 1.15 mL, 10 eq) was added drop wise to the stirred mixture over 10 min. The mixture was then heated to 45° C. for 1 h. The mixture was filtered through Celite, washed with ethanol and the solvent removed under reduced pressure to afford the product as a brown oil (2.1 mmol, 0.82 g, 92%).
$MH^+$=386.2.

DESCRIPTION 36

1,1-Dimethylethyl 4-(5-bromo-6-methyl-2-oxo-2,3-dihydro-1H-benzimidazol-1-yl)-1-piperidinecarboxylate (D36)

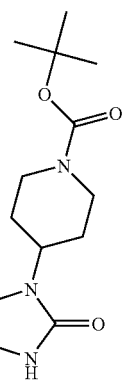

1,1-Dimethylethyl-4-[(2-amino-4-bromo-5-methylphenyl)amino]-1-piperidinecarboxylate (D35) (2.1 mmol, 0.82 g) was dissolved in dry tetrahydrofuran (10 mL) and N,N'-carbonyldiimidazole (3.45 mmol, 553 mg, 1.5 eq) added and the mixture heated to 50° C. for 17 h. The mixture was concentrated under reduced pressure, aqueous Na$_2$CO$_3$ (10%, 80 ml) added and the product extracted with ethyl acetate (2×20 ml). The organic layers were combined, dried (MgSO$_4$) and the solvent removed under reduced pressure to yield the crude product. The product was purified by chromatography, eluting with 5% to 60% ethyl acetate in pet ether 60-80 (5 CVs), to yield the product as a yellow solid (1.32 mmol, 541 mg, 57%)

MH$^+$=412.1.

DESCRIPTION 37

5-Bromo-6-methyl-1-(4-piperidinyl)-1,3-dihydro-2H-benzimidazol-2-one (D37)

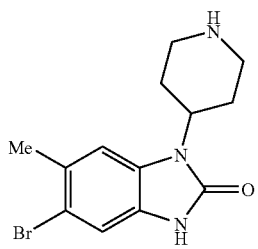

1,1-Dimethylethyl 4-(5-bromo-6-methyl-2-oxo-2,3-dihydro-1H-benzimidazol-1-yl)-1-piperidinecarboxylate (D36) (1.32 mmol, 541 mg) was dissolved in dichloromethane (5 mL), trifluoroacetic acid (5 mL) added and the mixture stirred under argon at room temperature for 1 h. The reaction mixture was concentrated under reduced pressure, Na$_2$CO$_3$ (10% aqueous solution) added and the product extracted with ethyl acetate (×3). The organic layers were combined, dried (MgSO$_4$) and the solvent removed under reduced pressure to afford the product as a yellow solid (1.16 mmol, 359 mg, 88%)

MH$^+$=311.99, 309.99.

DESCRIPTION 38

N-(4,5-Dichloro-2-nitrophenyl)-1-(tetrahydro-2H-pyran-4-yl)-4-piperidinamine (D38)

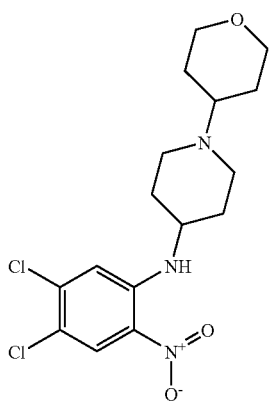

4,5-Dichloro-2-fluoronitrobenzene (315 mg) was dissolved in dry dimethylformamide (10 ml) and diisopropylethylamine (0.85 ml), and 1-(tetrahydro-2H-pyran-4-yl)-4-piperidinamine dihydrochloride (D40) (450 mg) were added at room temperature. The mixture was stirred at 80° C. for 1 h, then cooled to room temperature and water and ethyl acetate added. The organic layer was dried over MgSO$_4$, filtered and evaporated to give the title compound, 350 mg.

DESCRIPTION 39

N-(4,5-Dichloro-2-aminophenyl)-1-(tetrahydro-2H-pyran-4-yl)-4-piperidinamine (D39)

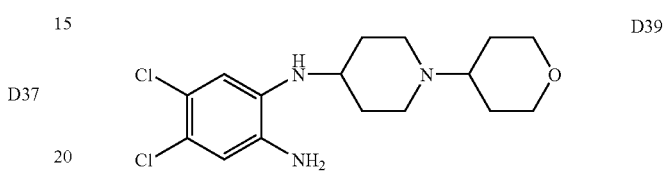

N-(4,5-Dichloro-2-nitrophenyl)-1-(tetrahydro-2H-pyran-4-yl)-4-piperidinamine (D38) (320 mg) was dissolved in ethanol (20 ml) and Raney nickel (50% aqueous suspension, 0.5 ml) was added at room temperature; the mixture was heated to 40° C. and hydrazine monohydrate (0.4 ml) was added over 20 min. After 30 min more, the reaction mixture was cooled to room temperature, filtered through Celite and the solvent was evaporated. Chromatography on silica gel eluting with methanol-dichloromethane mixtures yielded the title compound, 150 mg.

DESCRIPTION 40

1-(Tetrahydro-2H-pyran-4-yl)-4-piperidinamine dihydrochloride (D40)

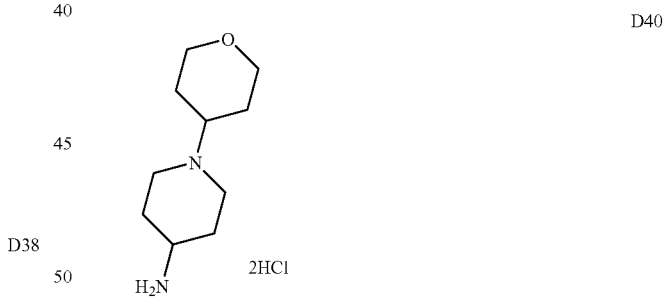

Sodium triacetoxyborohydride (22.47 g, 106 mmole) was added in portions to a stirred mixture of 4-BOC-aminopiperidine (10.60 g, 53 mmole) and tetrahydro-4H-pyran-4-one (5.57 g, 55.7 mmole) in dichloromethane (300 ml). The mixture was subsequently stirred at room temperature overnight, and then treated with dilute potassium carbonate solution (100 ml). After stirring for 10 mins the organic phase was separated washed with water and brine, dried over MgSO$_4$ and concentrated to dryness under vacuum. The solid residue was dissolved in ethanol (200 ml) and treated with concentrated HCl (25 ml) and stirred and heated to reflux for 2 hrs. The cooled mixture was concentrated to dryness under vacuum and the colourless solid residue was collected from diethyl ether and dried under vacuum to afford the title compound 10.92 g, 80% $^1$H NMR δ(DMSO-d6) 1.71 (2H, m), 2.04 (3H, m), 2.11 (3H, m), 3.01 (2H, m), 3.30 (4H, m; partially obscured by H$_2$O signal), 3.52 (2H, m), 3.97 (2H, m), 8.43 (3H, m), and 10.96 (1H, m).

DESCRIPTION 41

2-Chloro-4-nitro-5-fluorophenol (D41)

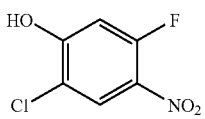

D41

A solution of 2-chloro-5-fluorophenol (1.5 g) in dichloromethane (50 ml) at 0° C. was treated with nitric acid (70%, 0.7 ml). The cooling bath was removed and after 15 min at room temperature the solution washed with water then dried over MgSO$_4$, filtered and evaporated. The product was crystallised from diethyl ether to yield the title compound, 500 mg.

DESCRIPTION 42

2-Chloro-4-nitro-5-fluoroanisole (D42)

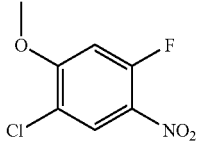

D42

A mixture of 2-chloro-4-nitro-5-fluorophenol (D41) (450 mg), potassium carbonate (600 mg), iodomethane (1 ml), and dimethylformamide (5 ml) stirred overnight at room temperature then diethyl ether added and the solution washed with water then dried over MgSO$_4$, filtered and evaporated The product was crystallised from hexane to yield the title compound, 350 mg.

DESCRIPTION 43

1,1-Dimethylethyl 4-[(4-fluoro-5-bromo-2-nitrophenyl)amino]-piperidinecarboxylate (D43)

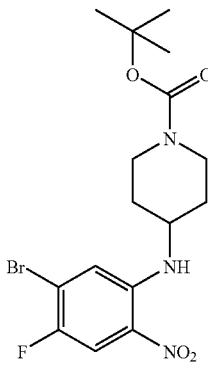

D43

4-Bromo-2,5-difluoronitrobenzene (0.60 g, 2.5 mmole) was dissolved in dry dimethylformamide (10 ml) and diisopropylethylamine (0.39 g, 3.0 mmole), and 1,1-dimethylethyl 4-amino-1-piperidinecarboxylate (0.53 g, 2.6 mmole) were added at room temperature and subsequently stirred for 1 hour. The mixture was then stirred at 80° C. for 2.5 h, then cooled to room temperature. The mixture was concentrated to dryness under vacuum and the residue partitioned between ethyl acetate and dilute aqueous potassium carbonate solution. The organic layer was dried over MgSO$_4$, filtered and evaporated, and the residue was purified by silica gel chromatography eluting with 10 to 50% diethyl ether in 40-60 pet ether to afford the title compound as an orange/red solid, 0.91 g, 87%. LC/MS—97% m/e-416/418 (M–H).

DESCRIPTION 44

1,1-Dimethylethyl 4-[(2-amino-4-fluoro-5-bromophenyl)amino]-1-piperidinecarboxylate (D44)

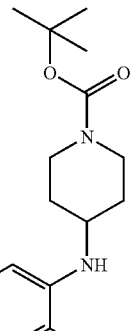

D44

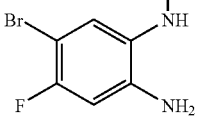

1,1-Dimethylethyl 4-[(4-fluoro5-bromo-2-nitrophenyl)amino]-piperidinecarboxylate (D43) (0.91 g, 2.2 mmoles) was suspended in ethanol (25 ml) and Raney nickel (50% aqueous suspension, 100 mg) was added at room temperature; the mixture was heated to 45° C. and hydrazine monohydrate (3.0 ml) was added over 10 min. After 1 hr more, the reaction mixture was cooled to room temperature, filtered through Celite and the solvent was evaporated to yield the title compound as an orange brown gum, 0.83 g, 98%. LC/MS—96% m/e 388/390 (M+H).

DESCRIPTION 45

1,1-Dimethylethyl 4-(5-fluoro-6-bromo-2-oxo-2,3-dihydro-1H-benzimidazol-1-yl)-1-piperidinecarboxylate (D45)

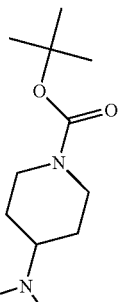

D45

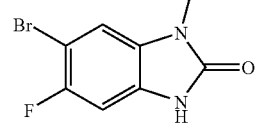

1,1-Dimethylethyl 4-[(2-amino-4-fluoro-5-bromophenyl)amino]-1-piperidinecarboxylate (D44) (0.83 g, 2.1 mmole) was dissolved in anhydrous tetrahydrofuran (20 ml) and carbonyl diimidazole (0.51 g, 3.2 mmole) was added in portions over 15 minutes. The mixture was stirred at rt for 1 hr and the at reflux temperature for 18 hrs. The cooled mixture was concentrated to dryness under vacuum and the residue purified by silica gel chromatography eluting with 15-100% ethyl acetate in n-pentane to afford the title compound as a buff solid, 0.54 g, 51% LC/MS—85% m/e 412/414 (MH−).

DESCRIPTION 46

5-Fluoro-6-bromo-1-(4-piperidinyl)-1,3-dihydro-2H-benzimidazol-2-one (D46)

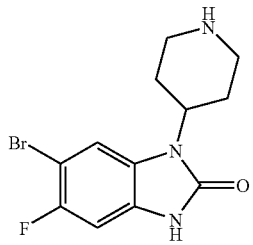

D46

A stirred mixture of 1,1-dimethylethyl 4-(5-fluoro-6-bromo-2-oxo-2,3-dihydro-1H-benzimidazol-1-yl)-1-piperidinecarboxylate (D45) (0.54 g, 1.3 mmole) and 6N HCl (1 ml) in ethanol (15 ml) was heated to reflux temperature for 4 hrs. The mixture was concentrated to dryness under vacuum and the residue treated with aq. sodium carbonate and extracted with ethyl acetate. The organic extract was dried ($MgSO_4$) and concentrated to dryness under vacuum to afford the title compound as pale buff powder, 0.35 g, 85%. LC/MS—92% 314/316 (M+H).

DESCRIPTION 47

1,1-Dimethylethyl 4-[(5-methoxy-4-chloro-2-nitrophenyl)amino]-piperidinecarboxylate (D47)

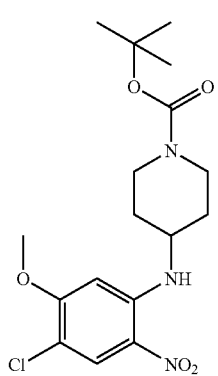

D47

2-Chloro-4-nitro-5-fluoroanisole (D42) (300 mg) was dissolved in dry dimethylformamide (3 ml) and diisopropylethylamine (0.3 ml), and 1,1-dimethylethyl 4-amino-1-piperidinecarboxylate (330 mg) were added at room temperature. The mixture was stirred for 3 h, then water and ethyl acetate added. The organic layer was dried over $MgSO_4$, filtered and evaporated, and the residue was crystallised from diethyl ether to afford the title compound, 400 mg.

DESCRIPTION 48

1,1-Dimethylethyl 4-[(2-amino-4-chloro-5-methoxyphenyl)amino]-1-piperidinecarboxylate (D48.)

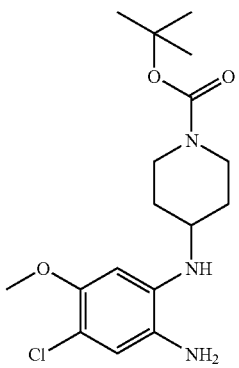

D48

1,1-Dimethylethyl 4-[(5-methoxy-4-chloro-2-nitrophenyl)amino]-piperidinecarboxylate (D47) (400 mg) was dissolved in ethanol (10 ml) and Raney nickel (50% aqueous suspension, 1.0 ml) was added at room temperature; the mixture was heated to 40° C. and hydrazine monohydrate (0.5 ml) was added over 30 min. After 30 min more, the reaction mixture was cooled to room temperature, filtered through Celite evaporated and chromatographed on silica gel eluting with ethyl acetate-hexane mixtures to yield the title compound, 300 mg.

DESCRIPTION 49

1,1-Dimethylethyl 4-(6-methoxy-5-chloro-2-oxo-2,3-dihydro-1H-benzimidazol-1-yl)-1-piperidinecarboxylate (D49)

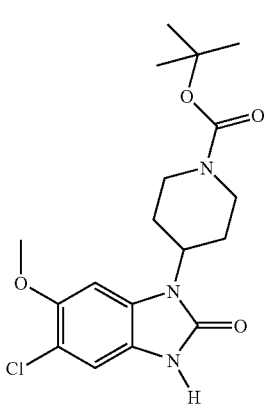

D49

1,1-Dimethylethyl 4-[(2-amino-4-chloro-5-methoxyphenyl)amino]-1-piperidinecarboxylate (D48) (280 mg) was dissolved in 5 ml of dichloromethane at 0° C. and phosgene (20% in toluene, 0.5 ml) and triethylamine (0.3 ml) were added and the mixture was stirred at 0° C. for 1 h, then washed with aqueous citric acid, then water, dried over MgSO$_4$, filtered and evaporated The product was chromatographed on silica gel eluting with methanol-dichloromethane mixtures, crystallised from diethyl ether, and then further purified by MDAP to yield the title compound, 40 mg.

DESCRIPTION 50

6-Methoxy-5-chloro-1-(4-piperidinyl)-1,3-dihydro-2H-benzimidazol-2-one hydrochloride (D50)

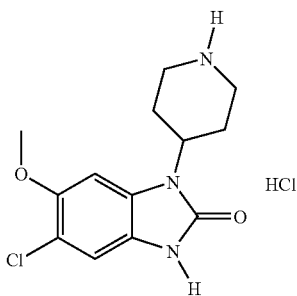

D50

1,1-Dimethylethyl 4-(6-methoxy-5-chloro-2-oxo-2,3-dihydro-1H-benzimidazol-1-yl)-1-piperidinecarboxylate (D49) (35 mg) was dissolved in ethanol (1 ml) and HCl (4M in 1,4-dioxane, 1 ml) was added at room temperature. The mixture was stirred at room temperature for 4 h then evaporated to give the title compound, 30 mg.

DESCRIPTION 51

N-(5-chloro-4-trifluoromethyl-2-nitrophenyl)-1-(tetrahydro-2H-pyran-4-yl)-4-piperidinamine (D51)

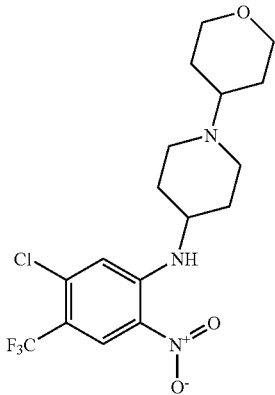

D51

2,4-Dichloro-5-nitrobenzenetrifluoride (0.70 g, 2.7 mmole), diisopropylethylamine (1.05 g, 8.1 mmole), and 1-(tetrahydro-2H-pyran-4-yl)-4-piperidinamine dihydrochloride (0.75 g, 2.9 mmole) were dissolved in dry dimethylformamide (20 ml). The mixture was stirred at 90° C. for 18 h, then cooled to room temperature and concentrated to dryness under vacuum. The residue was dissolved in dichloromethane (75 ml) and washed successively with dilute potassium carbonate solution, water and brine. The organic layer was dried over MgSO$_4$, filtered and evaporated and the residue purified by silica gel chromatography eluting with 1 to 5% methanol in dichloromethane to give the title compound as a yellow solid, 0.64 g, 58%. MH$^+$=408 and 410.

DESCRIPTION 52

5-Chloro-N-[1-(tetrahydro-2H-pyran-4-yl)-4-piperidinyl]-4-trifluoromethyl-1,2-benzenediamine (D52)

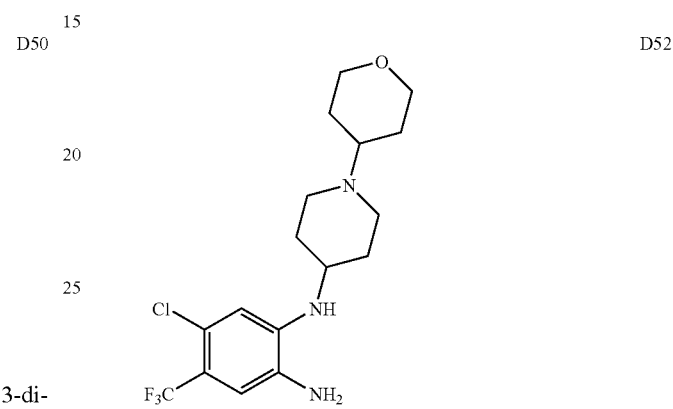

D52

N-(5-Chloro-4-trifluoromethyl-2-nitrophenyl)-1-(tetrahydro-2H-pyran-4-yl)-4-piperidinamine (D51) (0.64 g, 1.57 mmole) was dissolved in ethanol (25 ml) and Raney nickel (50% aqueous suspension, 100 mg) was added at room temperature; the mixture was heated to 60° C. and hydrazine monohydrate (0.8 ml) was added over 30 min. After 2 hr more, the reaction mixture was cooled to room temperature, filtered through Celite and the solvent was evaporated to dryness. The residue was purified by silica gel chromatography eluting with 2 to 20% methanol in dichloromethane to yield the title compound as a cream solid, 0.34 g, 58%. MH$^+$=378 and 380.

DESCRIPTION 53

1-Bromo-5-fluoro-4-nitro-2-(trifluoromethyl)benzene (D53)

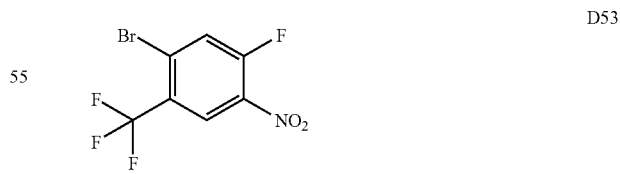

D53

A stirred solution of 2-bromo-4-fluorobenzotrifluoride (1.0 g, 4.1 mmole) in concentrated sulphuric acid (10 ml) at 0° C. was treated portionwise with KNO$_3$ (0.46 g, 4.6 mmole) and maintained at 0° C. for 0.5 hr before warming to room temp. over 2 hr. The mixture was added to well stirred ice/water (100 ml) and then extracted with ethyl acetate. The extract was dried and concentrated under vacuum to afford

DESCRIPTION 54

N-[5-Bromo-2-nitro-4-(trifluoromethyl)phenyl]-1-(tetrahydro-2H-pyran-4-yl)-4-piperidinamine (D54)

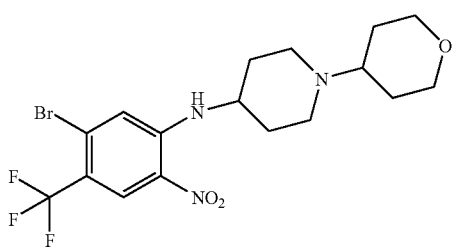

A stirred solution of 1-bromo-5-fluoro-4-nitro-2-(trifluoromethyl)benzene (D53) (0.30 g, 1.04 mmole) in dimethylformamide (5 ml) at room temperature under argon was treated with diisopropylethylamine (0.59 ml, 3.3 mmoles) and 1-(tetrahydro-2H-pyran-4-yl)-4-piperidinamine dihydrochloride (D40) (0.28 g, 1.1 mmole) and heated at 70° C. for 1 hr. The mixture was concentrated under vacuum and the residue treated with 10% $Na_2CO_3$ solution and extracted with ethyl acetate. The extract was dried and concentrated under vacuum to leave an orange solid which was purified by chromatography on silica gel eluting with 0-20% methanol/ethyl acetate to afford the title compound as a bright yellow solid (0.38 g, 81%). MH$^+$=452, 454.

$^1$H NMR (400 MHz, CDCl$_3$) δ: 1.55-1.80 (m, 6H), 2.07-2.17 (m, 2H), 2.40-2.60 (m, 3H), 2.88-2.98 (m, 2H), 3.40 (dt, 2H), 3.5-3.62 (m, 1H), 4.00-4.09 (m, 2H), 7.18 (s, 1H), 8.30 (d, 1H), 8.50 (s, 1H).

DESCRIPTION 55

5-Bromo-N-[1-(tetrahydro-2H-pyran-4-yl)-4-piperidinyl]-4-(trifluoromethyl)-1,2-benzenediamine (D55)

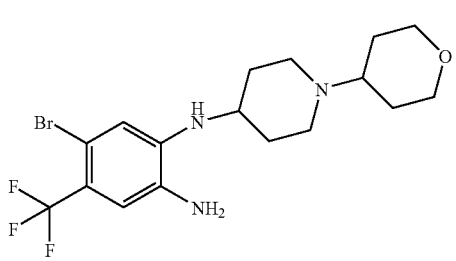

A stirred suspension of N-[5-bromo-2-nitro-4-(trifluoromethyl)phenyl]-1-(tetrahydro-2H-pyran-4-yl)-4-piperidinamine (D54) (380 mg, 0.84 mmole) in ethanol (20 ml) at room temperature under argon was treated with Raney Nickel (20 mg) followed by the dropwise addition of hydrazine hydrate (0.25 ml, 8.0 mmole). The mixture was maintained at room temp. for 0.5 hr, then heated at 45° C. for 1 hr producing a grey solution, which was filtered through Kieselguhr and the filtrate concentrated under vacuum to afford the title compound as a pale yellow solid (350 mg, 99%). MH$^+$=422, 424.

DESCRIPTION 56

1-Fluoro-5-methyl-2-nitro-4-(trifluoromethyl)benzene (D56)

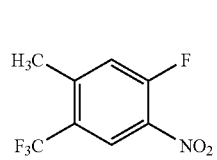

4-Fluoro-2-methyl-1-(trifluoromethyl)benzene (5.6 mmol, 1 g) was dissolved in concentrated sulphuric acid (7 ml) and cooled to 0° C.; KNO$_3$ (1 eq., 5.6 mmol, 566 mg) was added at to 0° C. in one pot and the mixture was stirred at to 0° C. for 4 hours. The crude mixture was poured onto ice and extracted with ethyl acetate; the organics were combined dried over Na$_2$SO$_4$, filtered and the solvent was evaporated to afford the title compound, 1.1 g, 88%.

$^1$HNMR δ(DMSO, 400 MHz) 2.555 (1H, s), 7.808 (1H, d), 8.372 (1H, d).

DESCRIPTION 57

1,1-Dimethylethyl 4-{[5-methyl-2-nitro-4-(trifluoromethyl)phenyl]amino}-1-piperidinecarboxylate (D57)

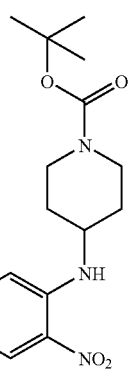

1-Fluoro-5-methyl-2-nitro-4-(trifluoromethyl)benzene (D56) (4.9 mmol, 1.1 g) was dissolved in dry dimethylformamide (3 ml) and diisopropylethylamine (1 eq., 4.9 mmol, 0.460 ml), 1,1-dimethylethyl 4-amino-1-piperidinecarboxylate (1 eq., 4.9 mmol, 981 mg) were added at room temperature and the mixture was stirred at 80° C. for 3 hours. The crude mixture was then cooled to room temperature and water was added; the aqueous solution was extracted with ethyl acetate; organics were alternatively washed with brine and water. The organics were combined dried over Na$_2$SO$_4$, filtered and the solvent was evaporated to afford the crude

DESCRIPTION 58

1,1-Dimethylethyl 4-{[2-amino-5-methyl-4-(trifluoromethyl)phenyl]amino}-1-piperidinecarboxylate (D58)

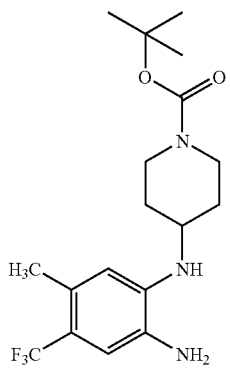

1,1-Dimethylethyl 4-{[5-methyl-2-nitro-4-(trifluoromethyl)phenyl]amino}-1-piperidine-carboxylate (D57) (3.17 mmol, 1.29 g) was dissolved in ethanol (20 ml) and an aqueous suspension of Raney-Nickel (3 ml) was added at room temperature; the mixture was heated to 40-50° C. and hydrazine monohydrate (15 eq., 48 mmol, 1.5 ml) was added over 20-30 min. The reaction mixture was then cooled to room temperature, filtered through celite and the solvent was evaporated to yield the title compound, 1.1 g, 92%, M$^+$-Boc+H=274.

DESCRIPTION 59

1,1-Dimethylethyl 4-[6-methyl-2-oxo-5-(trifluoromethyl)-2,3-dihydro-1H-benzimidazol-1-yl]-1-piperidinecarboxylate (D59)

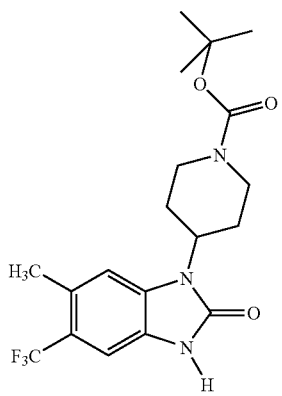

1,1-Dimethylethyl 4-{[2-amino-5-methyl-4-(trifluoromethyl)phenyl]amino}-1-piperidine-carboxylate (D58) (2.92 mmol, 1.1 g) was dissolved in 5 ml of tetrahydrofuran and CDI (1,1'-(oxomethanediyl)bis-1H-imidazole) (1.5 eq., 4.4 mmol, 0.71 g) was added at room temperature; the mixture was stirred at 50-60° C. overnight. The mixture was cooled to room temperature and it was partitioned in ethyl acetate/H$_2$O; the two layers were separated and the aqueous phase was extracted with ethyl acetate (2×); the organic phases were combined and washed with citric acid solution (10% aqueous), brine and they were dried over Na$_2$SO$_4$, filtered and the solvent was evaporated to afford the crude compound that was purified by chromatography (ethyl acetate-n-hexane)) to yield the title compound, 900 mg, 81%, M$^+$-H=398.

DESCRIPTION 60

6-Methyl-1-(4-piperidinyl)-5-(trifluoromethyl)-1,3-dihydro-2H-benzimidazol-2-one hydrochloride (D60)

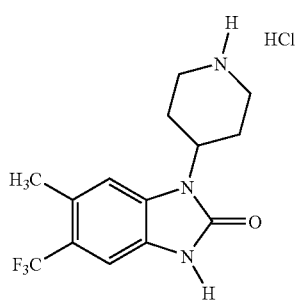

1,1-Dimethylethyl 4-[6-methyl-2-oxo-5-(trifluoromethyl)-2,3-dihydro-1H-benzimidazol-1-yl]-1-piperidinecarboxylate (D59) (2.23 mmol, 900 mg) was treated with HCl (10 ml of a 4M solution in 1,4-dioxane) at room temperature; the mixture was stirred at room temperature overnight. Solvent was evaporated to afford the title compound, mono hydrochloride salt, complete conversion, M$^+$+H=300.

DESCRIPTION 61

1,1-Dimethylethyl 4-[(4-trifluoromethyl-5-chloro-2-nitrophenyl)amino]-1-piperidinecarboxylate (D61)

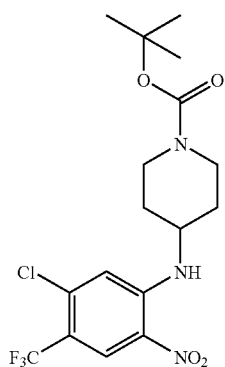

1,5-Dichloro-2-nitro-4-(trifluoromethyl)benzene (5.5 g) was dissolved in dry dimethylformamide (50 ml) and diisopropylethylamine (5.1 ml), and 1,1-dimethylethyl 4-amino- 1-piperidinecarboxylate (5.0 g) were added at room temperature. The mixture was stirred at 80° C. for 2.5 h, then water and ethyl acetate added. The organic layer was washed with water then brine, dried over MgSO₄, filtered and evaporated, and the residue was crystallised from diethyl ether to afford the subtitle compound, 6.7 g.

DESCRIPTION 62

1,1-Dimethylethyl 4-[(2-amino-5-chloro-4-trifluoromethylphenyl)amino]-1-piperidinecarboxylate (D62)

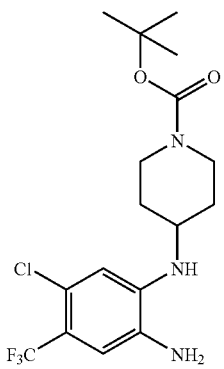

1,1-Dimethylethyl 4-[(4-trifluoromethyl-5-chloro-2-nitrophenyl)amino]-1-piperidinecarboxylate (D61, 6.7 g) was dissolved in ethanol (100 ml) and Raney nickel (50% aqueous suspension, 5 ml) was added at room temperature; the mixture was heated to 50° C. and hydrazine monohydrate (3 ml) was added over 30 min. After 1 h more, the reaction mixture was cooled to room temperature, filtered through Celite, evaporated, re-evaporated from toluene, and the residue crystallised from dichloromethane to yield the subtitle compound, 4.0 g.

DESCRIPTION 63

1,1-Dimethylethyl 4-(5-trifluoromethyl-6-chloro-2-oxo-2,3-dihydro-1H-benzimidazol-1-yl)-1-piperidinecarboxylate (D63)

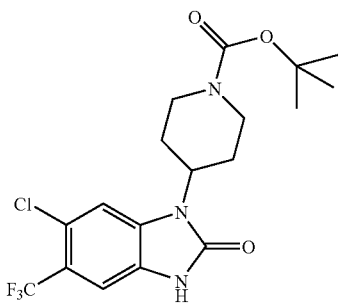

1,1-Dimethylethyl 4-[(2-amino-5-chloro-4-trifluoromethylphenyl)amino]-1-piperidinecarboxylate (D62, 2.2 g) was dissolved in 25 ml of dichloromethane at 0° C. and triphosgene (0.6 g) and diisopropylethylamine (1.0 ml) were added and the mixture was stirred at 0° C. for 1 h, then washed with aqueous citric acid, dried over MgSO₄, filtered and evaporated The product was chromatographed on silica gel eluting with methanol-dichloromethane mixtures, then crystallised from diethyl ether to yield the subtitle compound, 1.0 g.

DESCRIPTION 64

5-Trifluoromethyl-6-chloro-1-(4-piperidinyl)-1,3-dihydro-2H-benzimidazol-2-one hydrochloride (D64)

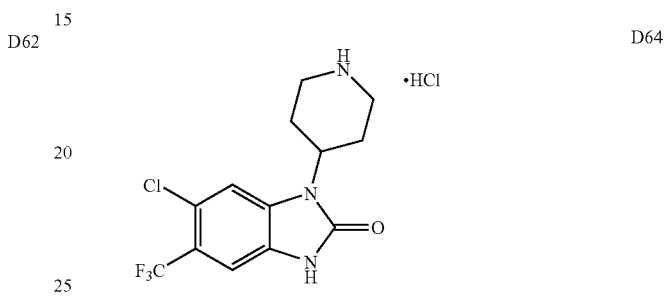

1,1-Dimethylethyl 4-(5-trifluoromethyl-6-chloro-2-oxo-2,3-dihydro-1H-benzimidazol-1-yl)-1-piperidinecarboxylate (D63, 1.0 g) was dissolved in dichloromethane (10 ml) and HCl (4M in 1,4-dioxane, 2.5 ml) was added at room temperature. The mixture was stirred at room temperature for 4 h then evaporated to give the subtitle compound, 850 mg.

DESCRIPTION 65

4-{4-[6-Chloro-2-oxo-5-(trifluoromethyl)-2,3-dihydro-1H-benzimidazol-1-yl]-1-piperidinyl}tetrahydro-2H-pyran-4-carbonitrile (D65)

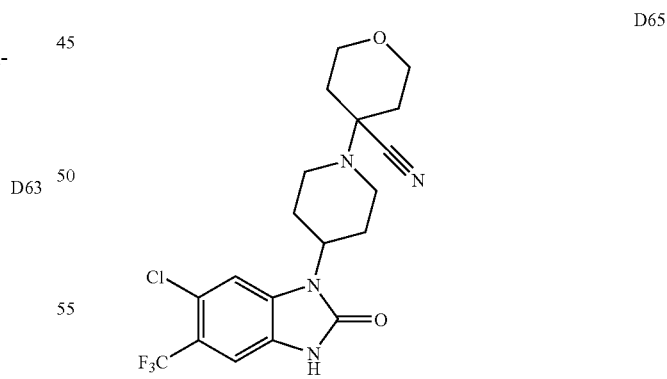

5-Trifluoromethyl-6-chloro-1-(4-piperidinyl)-1,3-dihydro-2H-benzimidazol-2-one hydrochloride (D64, 850 mg) was converted to the free base using SCX then combined with acetone cyanohydrin (400 mg), tetrahydropyran-4-one (500 mg) magnesium sulphate (1.5 g) and dimethylacetamide (2.5 ml), and the mixture heated under a slow stream of argon for 18 h at 60° C. To the cooled mixture were added water and ethyl acetate. The organic layer was dried over MgSO₄, filtered and evaporated, and the residue was crystallised from diethyl ether to afford the subtitle compound, 160 mg.

DESCRIPTION 66

1,1-Dimethylethyl 4-{[5-bromo-2-nitro-4-(trifluoromethyl)phenyl]amino}-1-piperidinecarboxylate (D66)

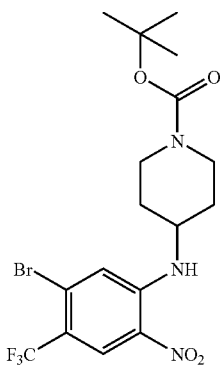

D66

A stirred solution of 2-bromo-4-fluoro-5-nitrobenzotrifluoride (1.15 g, 4.0 mmol) in dimethylformamide (15 ml) at room temperature under argon was treated with diisopropylethylamine (1.8 ml, 10 mmol) and 1,1-dimethylethyl 4-amino-1-piperidinecarboxylate (0.90 g, 4.5 mmol), then heated at 75° C. for 3 hrs. The solution was concentrated under vacuum and the residue treated with 10% $Na_2CO_3$ solution (30 ml) and extracted with ethyl acetate (2×40 ml). The combined extract was washed with brine (40 ml), then dried ($Na_2SO_4$) and concentrated under vacuum to leave an orange solid which was purified by chromatography on silica gel (20 g) eluting with dichloromethane to afford the title compound as a yellow solid (1.08 g, 58%).

$^1$HNMR δ(CDCl$_3$, 400 MHz): 8.51 (1H, s), 8.27 (1H, d), 7.20 (1H, s), 4.15-4.00 (2H, m), 3.75-3.63 (1H, m), 3.15-3.00 (2H, m), 2.12-2.02 (2H, m), 1.65-1.50 (2H, m), 1.48 (9H, s).

DESCRIPTION 67

1,1-Dimethylethyl 4-{[2-amino-5-bromo-4-(trifluoromethyl)phenyl]amino}-1-piperidinecarboxylate (D67)

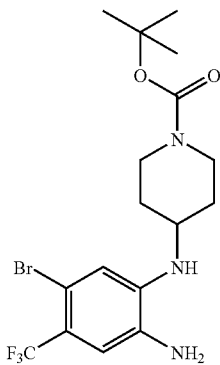

D67

A stirred suspension of 1,1-dimethylethyl 4-{[5-bromo-2-nitro-4-(trifluoromethyl)phenyl]amino}-1-piperidinecarboxylate (D66, 1.10 g, 2.3 mmol) in ethanol (50 ml) at room temperature under argon was treated with Raney Nickel (30 mg) followed by dropwise addition over 10 minutes of hydrazine hydrate (0.50 ml, 16 mmol). The mixture was stirred well at room temperature for 20 minutes, then heated at 45° C. for 1 hr, before cooling to 20° C. and filtering through Kieselguhr. The filtrate was concentrated under vacuum to afford the title compound as a white solid (0.98 g, 95%).

$^1$HNMR δ (CDCl$_3$, 400 MHz): 7.01 (1H, s), 6.82 (1H, s), 4.06 (2H, br s), 3.75-3.68 (1H, m), 3.50-3.40 (1H, m), 3.28 (2H, br s), 2.97 (2H, t), 2.04 (2H, dd), 1.50-1.35 (2H, m), 1.47 (9H, s).

DESCRIPTION 68

1,1-Dimethylethyl 4-[6-bromo-2-oxo-5-(trifluoromethyl)-2,3-dihydro-1H-benzimidazol-1-yl]-1-piperidinecarboxylate (D68)

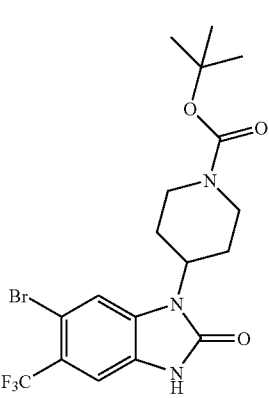

D68

A stirred solution of 1,1-dimethylethyl 4-{[2-amino-5-bromo-4-(trifluoromethyl)phenyl]amino}-1-piperidinecarboxylate (D67, 0.98 g, 2.2 mmol) in tetrahydrofuran (25 ml) at room temperature under argon was treated with diisopropylethylamine (0.78 ml, 4.4 mmol) followed by ethyl chloroformate (0.24 ml, 2.5 mmol) and maintained for 20 hrs. The solution was concentrated under vacuum and the residue treated with 10% $Na_2CO_3$ solution and extracted with ethyl acetate. The extract was dried ($Na_2SO_4$) and concentrated under vacuum to leave a beige solid, which was dissolved in dimethylformamide (20 ml) and heated with stirring under argon for 1.5 hrs. The mixture was concentrated under vacuum and the residue treated with 10% $Na_2CO_3$ solution and extracted with ethyl acetate. The extract was dried ($Na_2SO_4$) and concentrated under vacuum to afford the title compound as a light brown solid (0.95 g, 91%).

$^1$HNMR δ (CDCl$_3$, 400 MHz): 9.77 (1H, br s), 7.44 (1H, s), 7.42 (1H, s), 4.50-4.25 (3H, m), 2.95-2.80 (2H, m), 2.35-2.20 (2H, m), 1.84 (2H, d), 1.52 (9H, s).

DESCRIPTION 69

6-Bromo-1-(4-piperidinyl)-5-(trifluoromethyl)-1,3-dihydro-2H-benzimidazol-2-one hydrochloride
(D69)

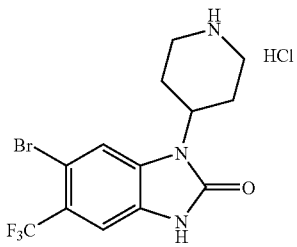

A solution of 1,1-dimethylethyl 4-[6-bromo-2-oxo-5-(trifluoromethyl)-2,3-dihydro-1H-benzimidazol-1-yl]-1-piperidinecarboxylate (D68, 0.95 g, 2.0 mmol) in diethyl ether (50 ml) and methanol (10 ml) was treated at room temperature with 1M HCl/diethyl ether (10 ml, 10 mmol) and stirred for 20 hrs. The precipitate was filtered off, washed with diethyl ether and dried to afford the title compound as a beige solid (0.71 g, 87%).

$^1$HNMR δ (d$^6$DMSO, 400 MHz): 11.55 (1H, s), 9.21 (1H, br d), 9.03 (1H, br m), 7.97 (1H, s), 7.35 (1H, s), 4.65-4.55 (1H, m), 3.5-3.35 (2H, m), 3.13-3.00 (2H, m), 2.70-2.50 (2H, m), 1.88 (2H, d).

DESCRIPTION 70

4-{4-[6-Bromo-2-oxo-5-(trifluoromethyl)-2,3-dihydro-1H-benzimidazol-1-yl]-1-piperidinyl}tetrahydro-2H-pyran-4-carbonitrile
(D70)

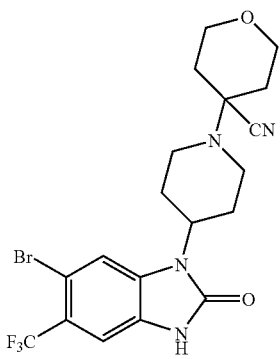

A stirred solution of 6-bromo-1-(4-piperidinyl)-5-(trifluoromethyl)-1,3-dihydro-2H-benzimidazol-2-one (free base of D69, 0.28 g, 0.77 mmol) in N,N-dimethylacetamide (3 ml) at room temperature under argon was treated with acetone cyanohydrin (0.13 g, 1.5 mmol) and dry magnesium sulphate (0.50 g), then heated at 60° C. whilst a gentle stream of argon was passed over the well stirred mixture. After 48 hrs the mixture containing a thick pale yellow precipitate was cooled to room temperature and treated with dichloromethane (25 ml), then stirred for 15 minutes. The liquid which contained the fine suspension of the solid precipitate was decanted off from the magnesium sulphate which had settled to the base of the flask. The decanted mixture was then filtered to afford the title compound as a white solid (>90% purity) (0.24 g, 66%).

$^1$HNMR δ (d$^6$DMSO, 400 MHz): 11.7 (1H, vbr s), 8.23 (1H, s), 7.67 (1H, s), 4.72-4.61 (1H, m), 4.32 (2H, d), 3.82 (2H, t), 3.60 (2H, d), 2.82-2.70 (2H, m), 2.61-2.50 (4H, m), 2.16 (2H, d), 2.10-1.95 (2H, m).

DESCRIPTION 71

4-{4-[6-Methyl-2-oxo-5-(trifluoromethyl)-2,3-dihydro-1H-benzimidazol-1-yl]-1-piperidinyl}tetrahydro-2H-pyran-4-carbonitrile
(D71)

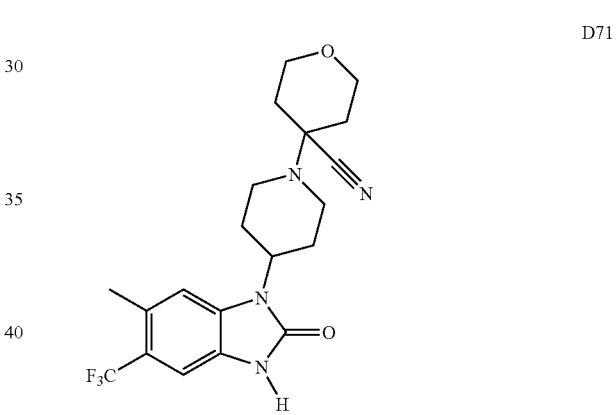

6-Methyl-1-(4-piperidinyl)-5-(trifluoromethyl)-1,3-dihydro-2H-benzimidazol-2-one (free base of D60, 0.473 g, 1.47 mmol), 2-hydroxy-2-methylpropanenitrile (2 eq., 2.94 mmol, 0.268 ml), tetrahydro-4H-pyran-4-one (2 eq., 2.94 mmol, 0.27 ml), MgSO$_4$ (880 mg) and N,N-dimethylacetamide (4 ml) were heated at 60° C. under argon for 24 hours. The mixture was subsequently cooled to room temperature and dichloromethane/water (70 ml/70 ml) were added and the biphasic mixture obtained was sonicated at room temperature for 20 minutes. The two phases were separated and the organic phase was dried by hydromatrix cartridge. The organic solvent was subsequently evaporated and the solid obtained was triturated with diethyl ether to afford the title compound (440 mgs, 70%).

$^1$HNMR δ(d$^6$DMSO, 400 MHz): 1.645 (2H, m), 1.782 (2H, d), 2.178 (4H, m), 2.420 (2H, m), 3.262 (2H, d), 3.459 (2H, t), 3.957 (2H, d), 4.220 (1H, m), 7.161 (1H, s), 7.382 (1H, s), 11.1 (1H, s broad).

DESCRIPTION 72

4-[4-(5-Fluoro-6-methyl-2-oxo-2,3-dihydro-1H-benzimidazol-1-yl)piperidin-1-yl]tetrahydro-2H-pyran-4-carbonitrile (D72)

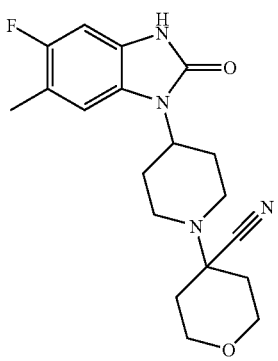

D72

A mixture of 5-fluoro-6-methyl-1-piperidin-4-yl-1,3-dihydro-2H-benzimidazol-2-one (D30, 0.6 g, 2.4 mmol), 2-hydroxy-2-methylpropanenitrile, (380 mg, 4.8 mmol), tetrahydro-4H-pyran-4-one (480 mg) magnesium sulphate (1.4 g) and N,N-dimethylacetamide (2.4 ml) were stirred at 65° C. under a slow stream of argon. Extra 2 ml DMA was added and stirred for a further 4 hours. The mixture was partitioned between dichloromethane and water. The dichloromethane layer was separated, dried by passing through a 3 g hydromatrix cartridge. The solvent was removed and the title compound was obtained as a off white solid from ether (617 mg). $M^+$ 359.

$^1$H NMR δ (d$^6$DMSO): 1.65 (2H, m), 1.75 (2H, m), 2.20 (4H, m), 2.23 (3H, s), 2.35 (2H, m), 3.25 (2H, d), 3.45 (2H, m), 3.95 (2H, m), 4.15 (1H, m), 6.77 (1H, d), 7.17 (1H, d), 10.87 (1H, s). $^{19}$F NMR δ (d$^6$DMSO): 126.05

DESCRIPTION 73

4-Fluoro-2-methyl-5-nitrophenyl 1-methylethyl ether (D73)

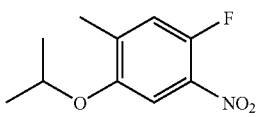

D73

A solution of 4-fluoro-2-methyl-5-nitrophenol (D16) (0.85 mmol, 145 mg) in tetrahydrofuran (5 mL) was treated with 2-propanol (0.85 mmol, 51.1 mg, 1 eq), diphenyl-2-pyridylphosphine (1.28 mmol, 335.7 mg, 1.5 eq) and di-tert-butyl azodicarboxylate (1.28 mmol, 293.5 mg, 1.5 eq) under argon at room temperature. The mixture was stirred for 3 h and then a solution of hydrogen chloride in ether (1M) was added and the mixture was stirred for 1 h. A gummy precipitate appeared. The mixture was concentrated under reduced pressure and the residue was dissolved in ether, washed twice with 5M aqueous hydrogen chloride solution for 30 min then washed twice with 10% aqueous sodium carbonate solution. The organic (ether) phase was dried and concentrated under reduced pressure to give a residue which was purified by chromatography on silica (ethyl acetate/petrol ether) to give the title compound as a pale yellow solid (0.53 mmol, 115 mg, 63% yield).

DESCRIPTION 74

1,1-Dimethylethyl 4-({5-methyl-4-[(1-methylethyl)oxy]-2-nitrophenyl}amino)-1-piperidinecarboxylate (D74)

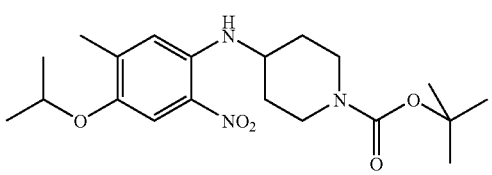

D74

A solution of 4-fluoro-2-methyl-5-nitrophenyl 1-methylethyl ether (D73) (0.53 mmol, 115 mg) in dimethylformamide (3 mL) was treated with 1,1-dimethylethyl 4-amino-1-piperidinecarboxylate (0.53 mmol, 106 mg, 1 eq) and diisopropylethylamine (0.53 mmol, 68.5 mg, 1 eq) under argon at room temperature and then heated at 80° C. overnight. The mixture was then concentrated under reduced pressure, then treated with 10% aqueous sodium carbonate solution and extracted with ether/ethyl acetate. The organics were dried, concentrated under reduced pressure and purified by chromatography on silica (ethyl acetate/petrol ether) to give the title compound as a solid (0.2 mmol, 80 mg, 39% yield). M+H 338.1 for main fragment (loss of tert-butyl group).

DESCRIPTION 75

1,1-Dimethylethyl 4-({2-amino-5-methyl-4-[(1-methylethyl)oxy]phenyl}amino)-1-piperidinecarboxylate (D75)

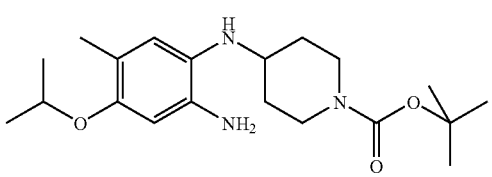

D75

A suspension/solution of 1,1-dimethylethyl 4-({5-methyl-4-[(1-methylethyl)oxy]-2-nitrophenyl}amino)-1-piperidinecarboxylate (D74) (0.2 mmol, 80 mg) in ethanol (10 mL) was treated with Raney Nickel, then hydrazine hydrate (2 mmol, 100 mg, 10 eq) was added dropwise over 5 min under argon at room temperature. The mixture was then heated at 45° C. for 30 min. The catalyst was then filtered off and washed with ethanol and methanol. The filtrate was concentrated under reduced pressure to give the title compound as a solid (0.16 mmol, 60 mg, 83% yield). M+H 364.3, 308.2, 264.2 (full molecule and fragments for loss of tert-butyl group and loss of Boc group).

DESCRIPTION 76

1,1-Dimethylethyl 4-{6-methyl-5-[(1-methylethyl)oxy]-2-oxo-2,3-dihydro-1H-benzimidazol-1-yl}-1-piperidinecarboxylate (D76)

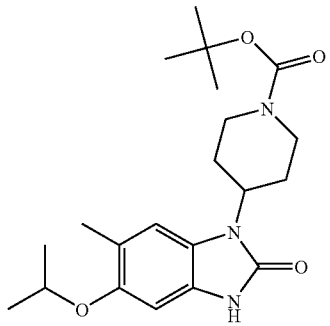

D76

A solution of 1,1-dimethylethyl 4-({2-amino-5-methyl-4-[(1-methylethyl)oxy]phenyl}amino)-1-piperidinecarboxylate (D75) (0.16 mmol, 60 mg) in tetrahydrofuran (0.5 mL) was treated with N,N'-carbonyldiimidazole (0.24 mmol, 38.5 mg, 1.5 eq) under argon at room temperature, then the mixture was heated at 50° C. for 1 h, concentrated under reduced pressure, and the residue was treated with 10% aqueous sodium carbonate solution and extracted twice with ethyl acetate. The organics were combined, dried and concentrated under reduced pressure. The residue was finally purified by chromatography on silica (ethyl acetate/petrol ether then methanol) to give the title compound (0.14 mmol, 53 mg, 85% yield). M+H 390.3, 334.3, 316.3 (full molecule and fragments for loss of tert-butyl group and loss of Boc group).

DESCRIPTION 77

6-Methyl-5-[(1-methylethyl)oxy]-1-(4-piperidinyl)-1,3-dihydro-2H-benzimidazol-2-one (D77)

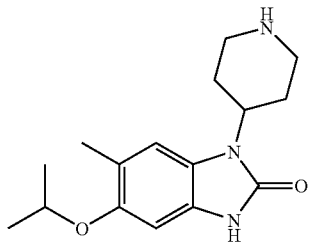

D77

A solution of 1,1-dimethylethyl 4-{6-methyl-5-[(1-methylethyl)oxy]-2-oxo-2,3-dihydro-1H-benzimidazol-1-yl}-1-piperidinecarboxylate (D76) (0.14 mmol, 53 mg) in dichloromethane (1 mL) was treated with trifluoroacetic acid (1 mL) under argon at room temperature and was allowed to stir for 1 h. The mixture was then concentrated under reduced pressure, the residue was treated with 10% aqueous sodium carbonate solution and extracted 3 times with ethyl acetate. The organics were combined, dried and concentrated under reduced pressure to give the title compound (118 mg, >>100%). M+H 290.3.

DESCRIPTION 78

N-(5-Bromo-4-fluoro-2-nitrophenyl)-1-(tetrahydro-2H-pyran-4-yl)-4-piperidinamine (D78)

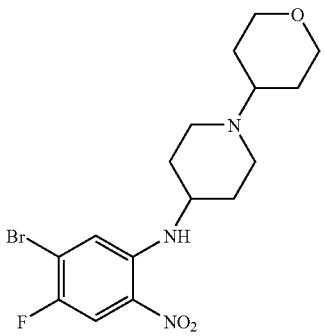

D78

A mixture of 4-bromo-2,5-difluoro-1-nitrobenzene (1 g, 4.2 mmol), 1-(tetrahydro-2H-pyran-4yl)piperidin-4-amine dihydrochloride salt (D40, 1.08 g, 4.2 mmol), and di-isopropylethylamine (2.2 ml, 1.26 mmol) in dimethylformamide (10 ml) was heated in microwave reactor for 5 min at 200° C. The mixture was washed with water, then extracted with dichloromethane and the extract dried over MgSO$_4$ and concentrated under vacuum. The crude material was purified on silica column (100 g of silica, ethyl acetate/methanol: 1.0% to 0%, 3CV; 2.0% to 100% 2CV 3. 100% to 100% 5CV) to leave 1.82 g (96%) of a mixture of title compound and an unknown impurity (~3:1 by HPLC).

MH$^+$=401, 402, 403 and 404.

DESCRIPTION 79

N-(5-Ethenyl-4-fluoro-2-nitrophenyl)-1-(tetrahydro-2H-pyran-4-yl)-4-piperidinamine (D79)

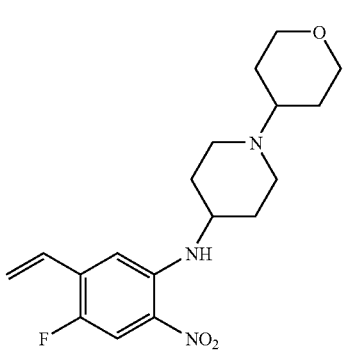

D79

A solution of N-(5-bromo-4-fluoro-2-nitrophenyl)-1-(tetrahydro-2H-pyran-4-yl)-4-piperidinamine (D78, 800 mg, ~75% purity) and n-tributylvinyltin (0.697 ml, 2.3 mmol) in toluene (30 ml) was treated, under a positive flow of argon, with triphenylphosphine (129.8 mg, 0.5 mmol) and bis (dibenzylideneacetone)palladium(0) (170.1 mg, 0.297 mmol), then stirred and heated under argon atmosphere at 130° C. for 1.5 h. The mixture was filtered through a celite pad. The organic layer was washed with NH$_4$OH (10% aq) and water, then dried over MgSO$_4$ and concentrated. The mixture was purified on silica column (100 g of silica, methanol/dichloromethane, 5% to 20%, 15CV) to afford 550 mg of title compound.

MH$^+$=350 and 351.

DESCRIPTION 80

(2-Amino-5-ethyl-4-fluorophenyl)-[1-(tetrahydro-2H-pyran-4-yl)-4-piperidinyl]amine (D80)

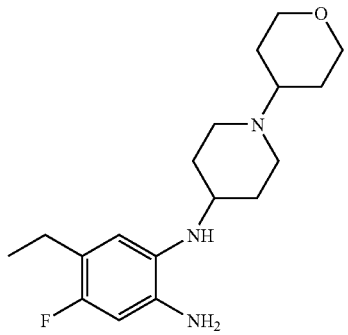

A mixture of N-(5-ethenyl-4-fluoro-2-nitrophenyl)-1-(tetrahydro-2H-pyran-4-yl)-4-piperidinamine (D79, 300 mg, 0.86 mmol) and ammonium formate (536 mg, 8.6 mmol) in methanol (50 ml), under argon, was treated with 10% Pd—C, then stirred overnight at room temperature. The mixture was filtered through a celite pad and the solvent evaporated under vacuum. The residue was dissolved in dichloromethane Na$_2$SO$_4$ and concentrated under vacuum to leave 230 mg of title compound as a brown oil (83% yield).

MH$^+$=322, 323.

DESCRIPTION 81

N-(5-Cyclopropyl-4-fluoro-2-nitrophenyl)-1-(tetrahydro-2H-pyran-4-yl)-4-piperidinamine (D81)

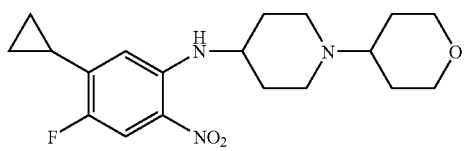

A solution of 1-(tetrahydro-2H-pyran-4-yl)-4-piperidinamine dihydrochloride (D40, 0.70 g) in water (5 ml) was basified to pH 12 with solid K$_2$CO$_3$, then extracted with dichloromethane and the combined organic extract was dried (MgSO$_4$) and concentrated under vacuum to dryness, to afford 1-(tetrahydro-2H-pyran-4-yl)-4-piperidinamine as a pale yellow solid (0.22 g).

A mixture of 4-cyclopropyl-2,5-difluoro-1-nitrobenzene (Fluorochem; 150 mg, 0.75 mmol), 1-(tetrahydro-2H-pyran-4-yl)-4-piperidinamine (153 mg, 0.83 mmol) and diisopropylethylamine (103 mg, 0.80 mmol) in dimethylformamide (2 ml) was heated in a microwave reactor at 200° C. for 3 minutes. The solution was concentrated under vacuum and the residue partitioned between ethyl acetate and dilute K$_2$CO$_3$ solution. The organic phase was separated, washed with water and brine, dried (MgSO$_4$) and concentrated to dryness under vacuum to afford an orange-brown solid (214 mg, 61% purity).

Another batch of the title product was made by a similar procedure to the above and using the following amounts: 4-cyclopropyl-2,5-difluoro-1-nitrobenzene (200 mg, 1.0 mmol), 1-(tetrahydro-2H-pyran-4-yl)-4-piperidinamine (308 mg, 1.2 mmol), diisopropylethylamine (464 mg, 3.6 mmol) and dimethylformamide (3 ml).

The two batches of crude products were combined and purified by silica gel chromatography eluting with 1-10% methanol/dichloromethane to afford the title compound as an orange solid.

$^1$H NMR δ (CDCl$_3$, 400 MHz): 0.80-0.87 (2H, m), 1.08-1.16 (2H, m), 1.55-1.70 (4H, m), 1.70-1.80 (2H, m), 2.00-2.14 (3H, m), 2.38-2.58 (3H, m), 2.82-2.94 (2H, m), 3.40 (2H, dt), 3.45-3.55 (1H, m), 4.04 (2H, dd), 6.28 (1H, d), 7.82 (1H, d), 8.07 (1H, d).

DESCRIPTION 82

5-Cyclopropyl-4-fluoro-N-[1-(tetrahydro-2H-pyran-4-yl)-4-piperidinyl]-1,2-benzenediamine (D82)

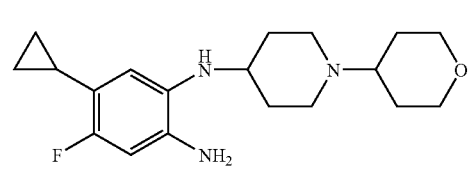

A stirred mixture of N-(5-cyclopropyl-4-fluoro-2-nitrophenyl)-1-(tetrahydro-2H-pyran-4-yl)-4-piperidinamine (D81, 0.38 g, 1.05 mmol), tin (II) chloride (0.8 mg, 4.20 mmol) and conc. HCl acid (~0.9 ml) in abs ethanol (30 ml) was heated at gentle reflux temperature for 18 hrs. After cooling, the majority of solvent was removed by concentration under reduced pressure and the residue treated with dilute K$_2$CO$_3$ solution (50 ml) and extracted with ethyl acetate, filtering the mixture to remove tin residues. The separated organic phase was dried (MgSO$_4$) and concentrated to dryness under vacuum to afford the title compound as a pale brown oil (340 mg, 97%).

$^1$H-NMR δ (CDCl$_3$, 400 MHz): 0.56-0.62 (2H, m), 0.84-0.90 (2H, m), 1.40-1.52 (2H, m), 1.53-2.07 (7H, m), 2.29 (2H, dt), 2.43-2.54 (1H, m), 2.87-2.97 (2H, m), 3.03-3.14 (1H, m), 3.39 (2H, dt), 3.47 (2H, br s), 4.03 (2H, dd), 6.22 (1H, d), 6.42 (1H, d). NH not discernible from spectra.

DESCRIPTION 83

5-Chloro-2-fluoro-4-[(1-methylethyl)oxy]-1-nitrobenzene (D83)

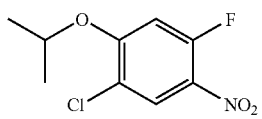

D83

A mixture of 2-chloro-5-fluoro-4-nitrophenol (287 mg, 1.5 mmol), propan-2-ol (90 mg, 1.5 mmol), diphenyl-2-pyridylphosphine (592 mg, 2.25 mmol) and di-tert-butyl azodicarboxylate (518 mg, 2.25 mmol) in tetrahydrofuran (10 ml) was stirred at room temperature under argon for 22 hrs. The mixture was treated with 1M HCl/diethyl ether (10 ml) and stirred at room temperature for 1 hr, then concentrated under vacuum and the residue dissolved in diethyl ether (10 ml), treated with 5M HCl acid (10 ml) and stirred for 30 mins. The organic layer was separated, washed with 5M HCl acid (10 ml), then 10% $Na_2CO_3$ solution (2×10 ml), dried ($MgSO_4$) and concentrated under vacuum. The residue was purified by chromatography on silica gel eluting with 5-70% ethyl acetate/60-80 petrol ether to afford the title compound as a yellow solid (153 mg, 43%).

$^1$H NMR δ($CDCl_3$, 250 MHz): 1.45 (6H, d), 4.65 (1H, septet), 6.76 (1H, d), 8.19 (1H, d).

DESCRIPTION 84

1,1-Dimethylethyl 4-({4-chloro-5-[(1-methylethyl) oxy]-2-nitrophenyl}amino)-1-piperidinecarboxylate (D84)

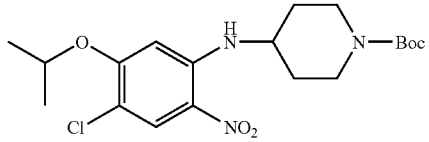

D84

A solution of 5-chloro-2-fluoro-4-[(1-methylethyl)oxy]-1-nitrobenzene (D83, 153 mg, 0.65 mmol) in dimethylformamide (5 ml) was treated with 1,1-dimethylethyl 4-amino-1-piperidinecarboxylate (130 mg, 0.65 mmol) and diisopropylethylamine (0.113 ml, 0.65 mmol) and stirred at approx. 80° C. for 17 hrs. The mixture was concentrated under vacuum and the residue treated with water and extracted with diethyl ether (×2). The combined extract was dried ($MgSO_4$) and concentrated under vacuum to afford the title compound as a yellow solid (260 mg, 97%).

DESCRIPTION 85

1,1-Dimethylethyl 4-({2-amino-4-chloro-5-[(1-methylethyl)oxy]phenyl}amino)-1-piperidinecarboxylate (D85)

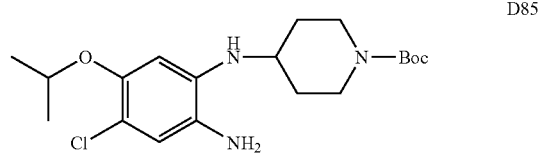

D85

A solution of 1,1-dimethylethyl 4-({4-chloro-5-[(1-methylethyl)oxy]-2-nitrophenyl}amino)-1-piperidinecarboxylate (D84, 260 mg, 0.63 mmol) in ethanol (40 ml) was treated with Raney Nickel followed by dropwise addition over 10 minutes of a solution of hydrazine hydrate (0.315 ml, 6.3 mmol) in ethanol. The mixture was heated at 45° C. for 1 hr, then the Raney Nickel was filtered off washing with ethanol and the filtrate concentrated under vacuum to afford the title compound as a purple coloured oil (200 mg, 83%).

DESCRIPTION 86

1,1-Dimethylethyl 4-{5-chloro-6-[(1-methylethyl) oxy]-2-oxo-2,3-dihydro-1H-benzimidazol-1-yl}-1-piperidinecarboxylate (D86)

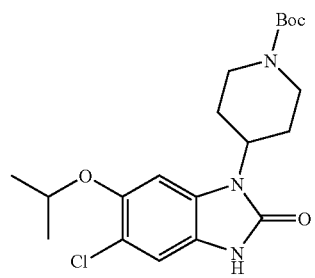

D86

A solution of 1,1-dimethylethyl 4-({2-amino-4-chloro-5-[(1-methylethyl)oxy]phenyl}amino)-1-piperidinecarboxylate (D85, 200 mg, 0.52 mmol) in tetrahydrofuran (2 ml) was treated with N,N'-carbonyldiimidazole (125 mg, 0.78 mmol) and heated at 50° C. for 17 hrs. The mixture was concentrated under vacuum and the residue treated with $Na_2CO_3$ solution (5 ml) and extracted with ethyl acetate (2×10 ml). The combined extract was dried (MgSO₄), concentrated under vacuum to leave the title compound as an oil (140 mg, 65%). M⁺−H=408.2.

DESCRIPTION 87

5-Chloro-6-[(1-methylethyl)oxy]-1-(4-piperidinyl)-1,3-dihydro-2H-benzimidazol-2-one (D87)

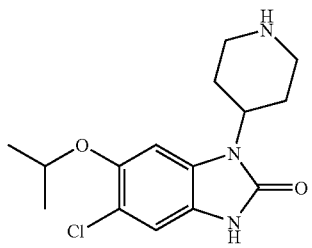

A solution of 1,1-dimethylethyl 4-{5-chloro-6-[(1-methylethyl)oxy]-2-oxo-2,3-dihydro-1H-benzimidazol-1-yl}-1-piperidinecarboxylate (D86, 140 mg, 0.34 mmol) in dichloromethane (3 ml) was treated with trifluoroacetic acid (3 ml) and stirred at room temperature under argon for 1 hr. The mixture was concentrated under vacuum and the residue treated with 10% Na₂CO₃ solution and extracted with ethyl acetate (×3). The combined extract was dried (MgSO₄) and concentrated under vacuum to leave the title compound as a red oil (94 mg, 83%). M⁺+H=310.0.

DESCRIPTION 88

5,6-Difluoro-1-[1-(phenylmethyl)-1,2,3,6-tetrahydro-4-pyridinyl]-1,3-dihydro-2H-benzimidazol-2-one (D88)

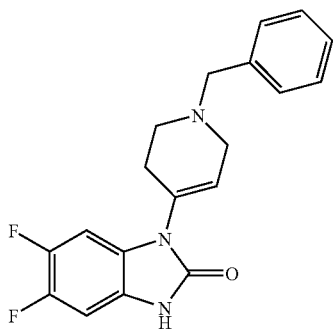

A suspension of 4,5-difluoro-1,2-benzenediamine (3 mmol, 432 mg) in xylene (20 mL) was treated with 1-benzyl-3-carbethoxy-4-piperidone (3 mmol, 783.9 mg) under argon and then heated under reflux for 8 h. The mixture was allowed to stand at room temperature for 7 h, then the mixture was heated under reflux again for 24 h. Xylene was removed under reduced pressure and the residue was chromatographed on silica (ethyl acetate/petrol ether) to give the title compound as an orange solid (1.41 mmol, 482 mg, 47% yield).

¹H NMR δ(CDCl₃): 9.7 (1H, s), 7.3 (5H, m), 6.9 (2H, m), 5.9 (1H, s), 3.7 (2H, s), 3.25 (2H, q), 2.8 (2H, t), 2.6 (2H, d).

DESCRIPTION 89

5,6-Difluoro-1-(4-piperidinyl)-1,3-dihydro-2H-benzimidazol-2-one (D89)

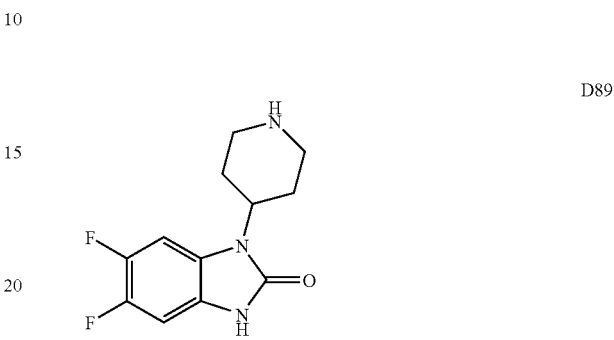

A solution of 5,6-difluoro-1-[1-(phenylmethyl)-1,2,3,6-tetrahydro-4-pyridinyl]-1,3-dihydro-2H-benzimidazol-2-one (D88) (0.7 mmol, 240 mg) in ethanol (10 mL) and acetic acid (2 mL) was treated under argon with 10% palladium on charcoal (50 mg, ~0.25 eq wt) and the mixture was stirred overnight under 25-30 PSI, then 8 h under 50 PSI of hydrogen at room temperature. The mixture was concentrated under reduced pressure to give a yellow/orange oil which crystallized with a touch of methanol (from evaporation of the methanol). The residue was dissolved again in 10 mL ethanol and 2 mL of acetic acid, then 50 mg of palladium on charcoal was added again under argon and the mixture was stirred under 50 PSI of hydrogen for 9 days, until completion of the reaction. The mixture was concentrated under reduced pressure to give the title compound as the acetate salt. M+H 254.2, M−H 252.2

DESCRIPTION 90

4-Fluoro-2-methyl-5-nitrobenzonitrile (D90)

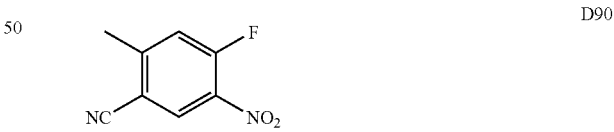

4-Fluoro-2-methylbenzonitrile (10 mmol, 1.35 g) was dissolved in concentrated sulphuric acid (10 mL) under argon then treated with potassium nitrate (10 mmol, 1.01 g, 1 eq) at 0° C. portionwise to keep the temperature around 0° C. The mixture was allowed to stir for 2 h while warming up to room temperature. The mixture was then poured onto ice and extracted twice with ether. The organics were combined, dried and concentrated under reduced pressure to give the title compound as a solid (9.4 mmol, 1.7 g, 94% yield).

¹H NMR δ(CDCl₃): 8.38 (1H, d), 7.3 (1H, d), 2.67 (3H, s).

DESCRIPTION 91

1,1-Dimethylethyl 4-[(4-cyano-5-methyl-2-nitrophenyl)amino]-1-piperidinecarboxylate (D91)

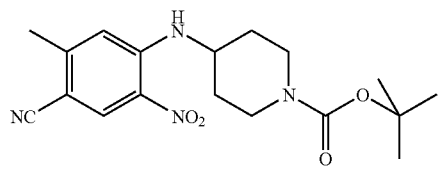

A solution of 4-fluoro-2-methyl-5-nitrobenzonitrile (D90) (3 mmol, 540.3 mg) in dimethylformamide (20 mL) was treated with 1,1-dimethylethyl 4-amino-1-piperidinecarboxylate (3 mmol, 600.9 mg, 1 eq) and diisopropylethylamine (3 mmol, 387.6 mg, 1 eq) under argon at room temperature and then heated at 80° C. overnight. The mixture was then concentrated under reduced pressure then treated with 10% aqueous sodium carbonate solution and extracted with ether/ethyl acetate. The organics were dried and concentrated under reduced pressure to give the title compound as a solid (3.3 mmol, 1.19 mg, >100% yield). M+H 304.97 for main fragment (loss of tert-butyl group).

DESCRIPTION 92

1,1-Dimethylethyl 4-[(2-amino-4-cyano-5-methylphenyl)amino]-1-piperidinecarboxylate (D92)

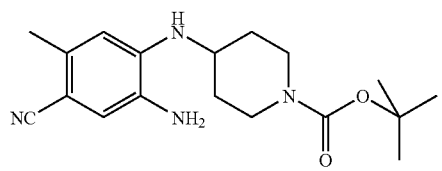

A suspension of 1,1-dimethylethyl 4-[(4-cyano-5-methyl-2-nitrophenyl)amino]-1-piperidinecarboxylate (D91) (3 mmol) in ethanol (30 mL) was treated with Raney Nickel and hydrazine hydrate (30 mmol, 1.5 g, 10 eq) under argon at room temperature. The mixture was then heated at 45° C. for 1 h. The catalyst was then filtered off and washed with ethanol and methanol. The filtrate was concentrated under reduced pressure to give the title compound as a solid (2.55 mmol, 840 mg, 85% yield). M+H 331.3, 275.2, 231.2 (full molecule and fragments for loss of tert-butyl group and loss of Boc group).

DESCRIPTION 93

1,1-Dimethylethyl 4-(5-cyano-6-methyl-2-oxo-2,3-dihydro-1H-benzimidazol-1-yl)-1-piperidinecarboxylate (D93)

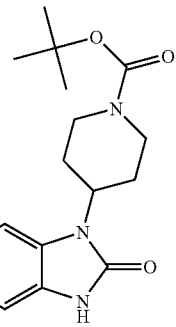

A solution of 1,1-dimethylethyl 4-[(2-amino-4-cyano-5-methylphenyl)amino]-1-piperidinecarboxylate (D92) (2.55 mmol, 840 mg) in tetrahydrofuran (8 mL) was treated with N,N'-carbonyldiimidazole (3.83 mmol, 613 mg, 1.5 eq) under argon at room temperature, then the mixture was heated at 50° C. for 1 h, concentrated under reduced pressure, and the residue was treated with 10% aqueous sodium carbonate solution and extracted twice with ethyl acetate. The organics were combined, dried and concentrated under reduced pressure to give the title compound (3.23 mmol, 1.15 g, >100% yield). M+H 357.3, 301.2 (full molecule and fragment for loss of the tert-butyl group).

DESCRIPTION 94

6-Methyl-2-oxo-1-(4-piperidinyl)-2,3-dihydro-1H-benzimidazole-5-carbonitrile (D94)

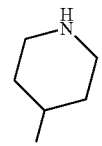

A solution of 1,1-dimethylethyl 4-(5-cyano-6-methyl-2-oxo-2,3-dihydro-1H-benzimidazol-1-yl)-1-piperidinecarboxylate (D93) (2.6 mmol, 1.15 g crude material) in dichloromethane (3 mL) was treated with trifluoroacetic acid (3 mL) under argon at room temperature and was allowed to stir for 1 h. The mixture was then concentrated under reduced pressure, the residue was treated with 10% aqueous sodium carbonate solution and extracted 3 times with ethyl acetate. The organics were combined, dried and concentrated under reduced pressure to give the title compound (2.66 mmol, 680 mg, ~100%). M+H 257.2.

DESCRIPTION 95

2-Chloro-4-fluoro-5-nitrobenzaldehyde (D95)

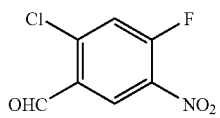

D95

A stirred solution of 2-chloro-4-fluorobenzaldehyde (1.0 g, 6.3 mmol) in conc. sulphuric acid (8 ml) at 0° C. under argon was treated portionwise with potassium nitrate (0.70 g, 6.9 mmol) and maintained at 0° C. for 30 minutes, before warming to room temperature over 1.5 hrs. The reaction mixture was added to well stirred ice/water (100 ml) and then extracted with ethyl acetate. The extract was dried and concentrated to leave the title compound as a pale yellow oil (1.15 g, 90%).

$^1$H NMR δ (CDCl$_3$, 400 MHz): 7.50 (1H, dd), 8.66 (1H, dd), 10.41 (1H, s).

DESCRIPTION 96

1-Chloro-2-(difluoromethyl)-5-fluoro-4-nitrobenzene (D96)

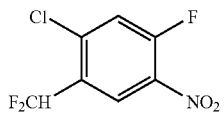

D96

A stirred solution of 2-chloro-4-fluoro-5-nitrobenzaldehyde (D95, 1.15 g, 5.6 mmol) in dichloromethane (25 ml) at 0° C. under argon was treated dropwise with (diethylamino)sulphur trifluoride (1.77 g, 11 mmol) and the resulting mixture allowed to warm to room temperature and stir for 66 hrs. The solution was then added to well stirred NaHCO$_3$ solution and maintained for 45 minutes. The mixture was extracted with dichloromethane and the extract dried and concentrated under vacuum to leave the title compound as a yellow oil (1.15 g, 91%).

$^1$H NMR δ (CDCl$_3$, 400 MHz): 6.92 (1H, t, J=54 Hz), 7.46 (1H, dd), 8.43 (1H, dd).

DESCRIPTION 97

N-[5-Chloro-4-(difluoromethyl)-2-nitrophenyl]-1-(tetrahydro-2H-pyran-4-yl)-4-piperidinamine (D97)

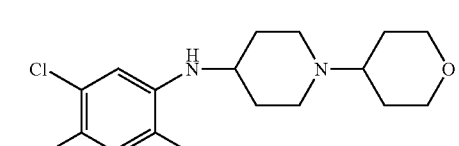

D97

A stirred solution of 1-chloro-2-(difluoromethyl)-5-fluoro-4-nitrobenzene (D96, 200 mg, 0.89 mmol) in dimethylformamide (4 ml) at room temperature under argon was treated with N,N-diisopropylethylamine (0.47 ml, 2.7 mmol), followed by 1-(tetrahydro-2H-pyran-4-yl)-4-piperidinamine dihydrochloride (D40, 240 mg, 0.94 mmol) and then heated at 70° C. for 1.5 hrs. The reaction mixture was concentrated under vacuum and the residue treated with 10% Na$_2$CO$_3$ solution and extracted with ethyl acetate. The extract was dried and concentrated under vacuum to leave an orange solid. This was purified by chromatography on silica gel eluting with 0-20% methanol/ethyl acetate to afford the title compound as a yellow solid (330 mg, 96%).

$^1$H NMR δ (CDCl$_3$, 400 MHz): 1.55-1.80 (6H, m), 2.05-2.18 (2H, m), 2.40-2.60 (3H, m), 2.88-3.00 (2H, m), 3.39 (2H, dt), 3.50-3.62 (1H, m), 4.04 (2H, dd), 6.79 (1H, t, J=54 Hz), 6.90 (1H, s), 8.25 (1H, d), 8.48 (1H, s).

DESCRIPTION 98

5-Chloro-4-(difluoromethyl)-N-[1-(tetrahydro-2H-pyran-4-yl)-4-piperidinyl]-1,2-benzenediamine (D98)

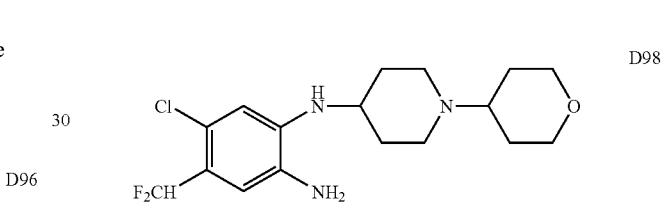

D98

A stirred suspension of N-[5-chloro-4-(difluoromethyl)-2-nitrophenyl]-1-(tetrahydro-2H-pyran-4-yl)-4-piperidinamine (D97, 330 mg, 0.84 mmol) in ethanol (20 ml) at room temperature under argon was treated with Raney Nickel (20 mg) followed by dropwise addition of hydrazine hydrate (0.25 ml, 8.0 mmol). The mixture was maintained at room temperature for 30 minutes, then heated at 45° C. for 1 hr. The mixture was filtered through a pad of Kieselguhr and the filtrate concentrated under vacuum to leave the title compound as a yellow solid (180 mg of ~88% purity, 59% yield).

$^1$H NMR δ (CDCl$_3$, 400 MHz): 1.45-1.70 (4H, m), 1.73-1.85 (2H, m), 2.09 (2H, br d), 2.37 (2H, t), 2.48-2.60 (1H, m), 2.97 (2H, br d), 3.10-3.60 (3H, br), 3.40 (2H, t), 3.56-3.70 (1H, m), 4.04 (2H, dd), 6.54 (1H, s), 6.85 (1H, t, J=54 Hz), 6.95 (1H, s).

DESCRIPTION 99

5,6-Dimethyl-1-[1-(phenylmethyl)-1,2,3,6-tetrahydro-4-pyridinyl]-1,3-dihydro-2H-benzimidazol-2-one (D99)

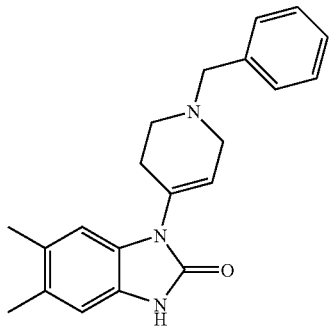

D99

A solution of 1-benzyl-3-carbethoxy-4-piperidone (3 mmol, 784 mg) in xylene (20 mL) was treated at room temperature with 4,5-dimethyl-1,2-benzenediamine (3 mmol, 408.6 mg, 1 eq) and the suspension was stirred under reflux under argon overnight then further for 5 h. The mixture was concentrated under reduced pressure to give a brown residue, which was treated with ethyl acetate and a touch of methanol. Beige crystals formed from the brown solution and were filtered off and dried under reduced pressure (vacuum oven) to give the title compound (1.05 mmol, 350 mg, 35% yield). M+H 334.3.

$^1$H NMR δ(d$^6$DMSO): 10.7 (1H, s), 7.35 (4H, m), 7.27 (1H, m), 6.82 (1H, s), 6.77 (1H, s), 5.82 (1H, t), 3.63 (2H, s), 3.12 (2H, d), 2.67 (2H, t), 2.44 (2H, d), 2.19 (6H, s).

DESCRIPTION 100

5,6-Dimethyl-1-(1,2,3,6-tetrahydro-4-pyridinyl)-1,3-dihydro-2H-benzimidazol-2-one (D100)

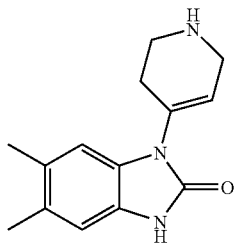

D100

A solution of 5,6-dimethyl-1-[1-(phenylmethyl)-1,2,3,6-tetrahydro-4-pyridinyl]-1,3-dihydro-2H-benzimidazol-2-one (D99) (1.05 mmol, 350 mg) in ethanol (10 mL) and acetic acid (2 mL) was treated with 10% palladium on charcoal (0.25 eq wt, 90 mg) then shaken under 50 PSI of hydrogen pressure for 24 h. The catalyst was filtered off and the filtrate was concentrated under reduced pressure to give the acetate salt of the title compound also containing some saturated analogue (reduction of the C=C double bond in the piperidine core) as a beige solid (1.2 mmol, 370 mg, >100% yield) M+H 246.2, M−H 242.3.

DESCRIPTION 101

4-[4-(5,6-Dimethyl-2-oxo-2,3-dihydro-1H-benzimidazol-1-yl)-3,6-dihydro-1(2H)-pyridinyl]tetrahydro-2H-pyran-4-carbonitrile (D101)

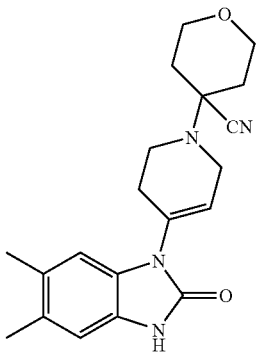

D101

A solution of 5,6-dimethyl-1-(1,2,3,6-tetrahydro-4-pyridinyl)-1,3-dihydro-2H-benzimidazol-2-one (D100) as HCl salt in water (5 mL) was treated with a few drops of acetic acid and then some sodium hydrogen carbonate to adjust the pH to 3-4. Then tetrahydro-4H-pyran-4-one (1.16 mmol, 116 mg, 1.4 eq) was added and the mixture was stirred under argon at room temperature for 20 min. Potassium cyanide (1.08 mmol, 70 mg, 1.3 eq) was added and stirred for further 6 h, then overnight. The mixture was allowed to stand for 2.5 days then was concentrated under reduced pressure and the residue was partitioned between ethyl acetate and water. LC/MS showed some title compound in the final residue (after removal of organic solvents under reduced pressure). The solid was engaged in the next procedure.

A solution of the previous solid in N,N-dimethylacetamide (1 mL) was treated under argon at room temperature with tetrahydro-4H-pyran-4-one (1.6 mmol, 160 mg, 2 eq), acetone cyanohydrin (1.6 mmol, 128 mg, 2 eq) and magnesium sulphate (480 mg). The mixture was then heated at 60° C. overnight. The mixture was concentrated under reduced pressure and partitioned between dichloromethane and 10% aqueous sodium carbonate solution. The aqueous phase was extracted twice with dichloromethane, the organics were combined, dried and concentrated under reduced pressure then the residue was triturated with ether to give the title compound as a solid (0.32 mmol, 113 mg, 40% overall yield)

still containing the corresponding reduced piperidine derivative. M+H 355.2, M−H 351.2.

DESCRIPTION 102

5,6-Dimethyl-1-[1-(4-methyltetrahydro-2H-pyran-4-yl)-1,2,3,6-tetrahydro-4-pyridinyl]-1,3-dihydro-2H-benzimidazol-2-one (D102)

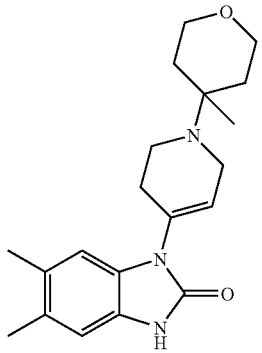

D102

A suspension of 4-[4-(5,6-dimethyl-2-oxo-2,3-dihydro-1H-benzimidazol-1-yl)-3,6-dihydro-1(2H)-pyridinyl]tetrahydro-2H-pyran-4-carbonitrile (D101) (0.32 mmol, 113 mg) in tetrahydrofuran (10 mL) was treated at room temperature under argon with methyl magnesium bromide (0.96 mmol, 0.32 mL of 3M solution in tetrahydrofuran, 3 eq) dropwise over 2 min. The mixture became a solution and was stirred for 45 min. Then 6 more equivalents of methyl magnesium bromide were added and stirred for 3 h. The mixture was cooled down to 0° C. and 1M aqueous ammonium chloride solution was added until everything was solubilised. Tetrahydrofuran was removed under reduced pressure and the mixture was diluted with water and extracted 3 times with ethyl acetate. The organics were combined, dried and concentrated to give a white solid (0.26 mmol, 89 mg, 81% crude yield). This solid was dissolved in 3 mL of dichloromethane and treated with 1 mL 1M ethereal hydrogen chloride. A yellow gum crashed out of the mixture. More ether was added and the gum turned into crystals upon trituration. The crystals were filtered off and dried to give the title compound as its hydrochloride salt (0.2 mmol, 75 mg, 62% yield) still containing hydrogenated compound (no double C=C bond in the piperidine core). M+H 342.1, 344.1, M−H 340.3.

EXAMPLE 1

6-Chloro-5-fluoro-1-[1-(tetrahydro-2H-pyran-4-yl)-4-piperidinyl]-1,3-dihydro-2H-benzimidazol-2-one hydrochloride (E1)

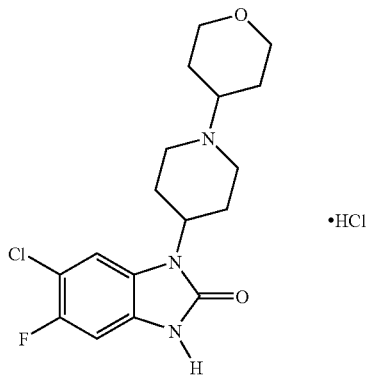

E1

6-Chloro-5-fluoro-1-(4-piperidinyl)-1,3-dihydro-2H-benzimidazol-2-one hydrochloride (D5) (0.286 mmol, 77 mg), Ti(iPrO)$_4$ (2 eq., 0.572 mmol, 0.170 ml), tetrahydro-4H-pyran-4-one (2 eq., 0.572 mmol, 0.053 ml) were stirred together at room temperature for one hour; dry methanol (2 ml) followed by NaBH$_3$CN (2 eq., 0.572 mmol, 36 mgs) were added and the mixture was stirred under argon at room temperature for 3 hours. The crude mixture was subsequently quenched with water (5 ml) and it was firstly purified by SCX followed by chromatography (methanol-NH$_3$-dichloromethane) to yield 6-chloro-5-fluoro-1-[1-(tetrahydro-2H-pyran-4-yl)-4-piperidinyl]-1,3-dihydro-2H-benzimidazol-2-one, 15 mg, 13%, M$^+$+H=353, which was converted into the hydrochloride salt using 1M HCl in diethyl ether.

$^1$H NMR (free base) δ(DMSO, 400 MHz) 1.45 (2H, m), 1.677 (4H, t), 2.29 (4H, m), 2.99 (2H, d), 3.28 (2H, t), 3.90 (2H, dd), 4.08 (1H, m broad), 7.03 (1H, d), 7.50 (1H, d), 11.1 (1H, s broad); remaining $^1$H signals not discernible in spectrum.

EXAMPLE 2

6-Chloro-5-methyl-1-[1-(tetrahydro-2H-pyran-4-yl)-4-piperidinyl]-1,3-dihydro-2H-benzimidazol-2-one hydrochloride (E2)

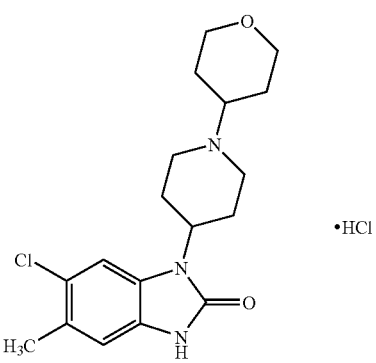

E2

6-Chloro-5-methyl-1-(4-piperidinyl)-1,3-dihydro-2H-benzimidazol-2-one hydrochloride (D9) (~0.2 mmol, 60 mg), Ti(iPrO)$_4$ (2 eq., 0.400 mmol, 0.130 ml), tetrahydro-4H-pyran-4-one (2 eq., 0.400 mmol, 40 ul) were stirred together at room temperature for one hour; dry MeOH (2 ml) followed by NaBH$_3$CN (2 eq., ~30 mgs) were added and the mixture was stirred under argon at room temperature for 3 hours. The crude mixture was subsequently quenched with water (5 ml) and it was firstly purified by SCX followed by chromatography (methanol-NH$_3$-dichloromethane) to yield 6-chloro-5-methyl-1-[1-(tetrahydro-2H-pyran-4-yl)-4-piperidinyl]-1,3-dihydro-2H-benzimidazol-2-one, 10 mg, 14%, M$^+$+H=350, which was converted into the hydrochloride salt using 1M HCl in diethyl ether.

$^1$H NMR (free base) δ (DMSO, 400 MHz) 1.45 (2H, m), 1.68 (4H, t), 2.24 (4H, m), 2.29 (3H, s), 3.00 (2H, d), 3.283 (2H, t), 3.90 (2H, dd), 4.07 (1H, m broad), 6.93 (1H, d), 7.24 (1H, d), 10.91 (1H, s broad); remaining $^1$H signals not discernible in spectrum.

EXAMPLE 3

5-Chloro-1-[1-(tetrahydro-2H-pyran-4-yl)-4-piperidinyl]-6-(trifluoromethyl)-1,3-dihydro-2H-benzimidazol-2-one hydrochloride (E3)

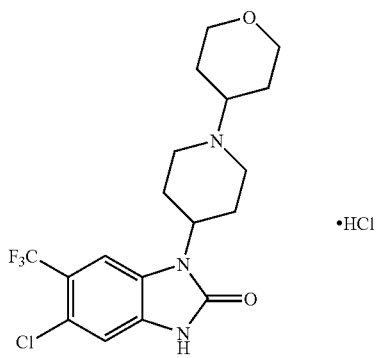

5-Chloro-1-(4-piperidinyl)-6-(trifluoromethyl)-1,3-dihydro-2H-benzimidazol-2-one hydrochloride (0.228 mmol, 82 mg) was dissolved in dichloromethane (6 ml) and triethylamine (3 eq., 0.68 mmol, 50 microliters), tetrahydro-4H-pyran-4-one (7 eq., 1.6 mmol, 160 mg), sodium triacetoxyborohydride (7 eq., 1.6 mmol, 340 mg) were added at room temperature and the mixture was stirred at room temperature for 3 hours. More triethylamine (4 ml), tetrahydro-4H-pyran-4-one (3.5 eq, 0.8 mmol, 80 mg), sodium triacetoxyborohydride (3.5 eq, 0.8 mmol, 170 mg) were added at room temperature and the mixture was stirred at room temperature for two extra hours. The solvent was evaporated and the mixture was worked up with sodium bicarbonate and DCM. The solvent was evaporated and triethylamine (3 eq., 0.68 mmol, 50 microliters), tetrahydro-4H-pyran-4-one (7 eq, 1.6 mmol, 160 mg), sodium triacetoxyborohydride (7 eq, 1.59 mmol, 340 mg) and DCE (4 ml) were introduced and all mixed together for 1 hour at room temperature. The mixture was quenched with water/NaHCO$_3$ (saturated solution) and DCM. The organic phase was separated from the aqueous phase (by hydrophobic filters) and the organic solvent was evaporated to afford the crude product that was purified by chromatography (MeOH—NH$_3$-dichloromethane) to afford 5-chloro-1-[1-(tetrahydro-2H-pyran-4-yl)-4-piperidinyl]-6-(trifluoromethyl)-1,3-dihydro-2H-benzimidazol-2-one, 29 mg, 31%, M$^+$+H=403, which was subsequently converted into the mono-hydrochloride salt using HCl (2 eq. from a 1M solution of HCl in diethyl ether).

$^1$HNMR δ(DMSO, 400 MHz, HCl salt) 1.73 (2H, m), 1.96 (4H, d), 2.72 (2H, m), 3.19 (2H, q), 3.44 (1H, m), 3.62 (2H, d), 4.00 (2H, dd), 7.28 (1H, s), 7.76 (1H, s), 11.51 (1H, s broad); remaining $^1$H signals not discernible in spectrum.

EXAMPLE 4

6-Methyl-5-(methyloxy)-1-[1-(tetrahydro-2H-pyran-4-yl)-4-piperidinyl]-1,3-dihydro-2H-benzimidazol-2-one hydrochloride (E4)

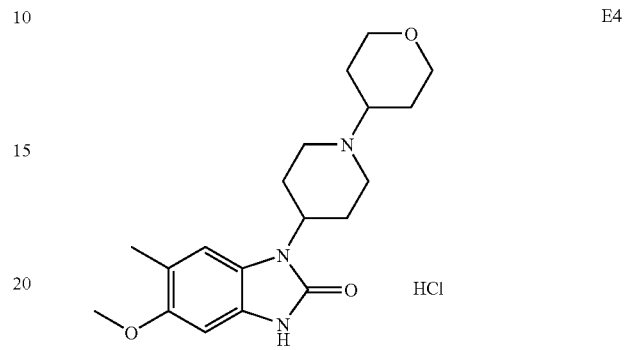

The title compound was prepared from D21 in a similar manner as 5-fluoro-6-methyl-1-[1-(tetrahydro-2H-pyran-4-yl)-4-piperidinyl]-1,3-dihydro-2H-benzimidazol-2-one (E6) and 0.1 mmol (40 mg) of product was obtained in 30% yield, which was converted into the hydrochloride salt using 1M HCl in diethyl ether.

M+H=346.04, $^1$H NMR (HCl salt) (DMSO-d6) δ: 11.13 (1H, s), 10.76 (1H, s), 7.62 (1H, s), 6.60 (1H, s), 4.54 (1H, m), 3.97 (2H, dd), 3.74 (3H, s), 3.62 (2H, d), 3.34 (3H, m), 3.17 (2H, q), 2.87 (2H, q), 2.16 (3H, s), 2.07 (2H, d), 1.83 (2H, d), 1.75 (2H, m).

EXAMPLE 5

5-Chloro-6-methyl-1-[1-(tetrahydro-2H-pyran-4-yl)-4-piperidinyl]-1,3-dihydro-2H-benzimidazol-2-one hydrochloride (E5)

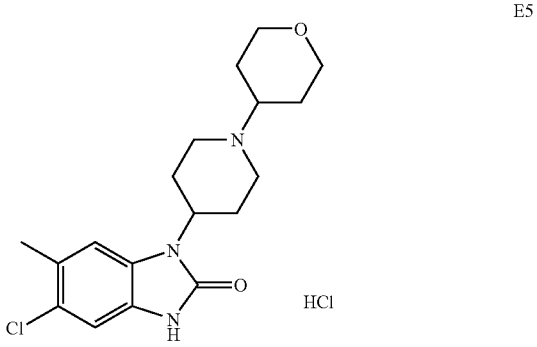

The title compound was prepared from D26 in a similar manner as 5-fluoro-6-methyl-1-[1-(tetrahydro-2H-pyran-4-yl)-4-piperidinyl]-1,3-dihydro-2H-benzimidazol-2-one (E6) and 0.23 mmol (90 mg) of product was obtained in 24% yield, which was converted into the hydrochloride salt using 1M HCl in diethyl ether.

M+H=350.08, ¹H NMR (HCl salt) (DMSO-d6) δ: 11.20 (1H, s), 10.97 (1H, s), 7.87 (1H, s), 6.98 (1H, s), 4.57 (1H, m), 3.98 (2H, dd), 3.58 (2H, d), 3.43 (1H, m), 3.34 (2H, t), 3.21 (2H, q), 2.90 (2H, q), 2.34 (3H, s), 2.07 (2H, d), 1.81 (2H, d), 1.75 (2H, m).

EXAMPLE 6

5-Fluoro-6-methyl-1-[1-(tetrahydro-2H-pyran-4-yl)-4-piperidinyl]-1,3-dihydro-2H-benzimidazol-2-one hydrochloride (E6)

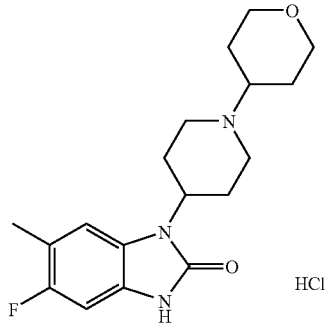

E6

5-Fluoro-6-methyl-1-(4-piperidinyl)-1,3-dihydro-2H-benzimidazol-2-one (D30) (0.64 mmol, 160 mg) in methanol (3 mL) was treated under argon at room temperature with tetrahydro-4H-pyran-4-one (1.28 mmol, 128 mg, 2 eq), then titanium tetra-isopropoxide (1.28 mmol, 364 mg, 2 eq). The mixture was stirred under argon for 1.5 h, then sodium cyanoborohydride (1.28 mmol, 80.4 mg, 2 eq) was added and stirred for 1.5 h. The mixture was loaded on an SCX cartridge, washed with 6 CV methanol and eluted with 6 CV 2M ammonia in methanol and dichloromethane. The eluate was concentrated under reduced pressure and purified 5-100% 2 m NH₃ in MeOH/DCM to give 5-fluoro-6-methyl-1-[1-(tetrahydro-2H-pyran-4-yl)-4-piperidinyl]-1,3-dihydro-2H-benzimidazol-2-one, which was transformed into the corresponding HCl salt (0.27 mmol, 100 mg, 42% yield), using 1M HCl in diethyl ether. M+H=334.12

¹H NMR (DMSO-d6) (free base) δ: 10.95 (1H, s), 7.65 (1H, d), 7.80 (1H, d), 4.56 (1H, m), 3.99 (2H, dd), 3.59 (2H, d), 3.38 (2H, m), 3.18 (3H, q), 2.86 (2H, q), 2.24 (3H, s), 2.05 (2H, d), 1.87 (2H, d), 1.75 (2H, m).

¹H NMR (DMSO-d6, HCl salt) 1.72 (2H, bdq), 1.83 (2H, bd), 2.04 (2H, bd), 2.33 (3H, d, J=2 Hz), 2.75 (2H, bq), 3.19 (2H, bq), 3.3-3.5 (5H, m), 4.02 (2H, bd), 6.80 (1H, d, J=10 Hz), 7.57 (1H, d, J=7 Hz), 10.63 (1H, bs), and 10.93 (1H, s).

EXAMPLE 7

5,6-Dimethyl-1-[1-(tetrahydro-2H-pyran-4-yl)-4-piperidinyl]-1,3-dihydro-2H-benzimidazol-2-one hydrochloride (E7)

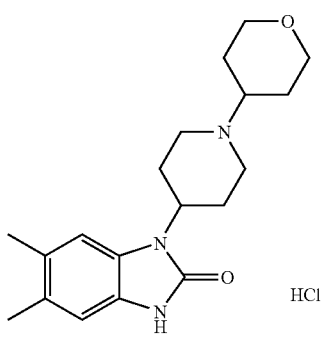

E7

5,6-Dimethyl-1-(4-piperidinyl)-1,3-dihydro-2H-benzimidazol-2-one (D32) (330 mg, 0.6 mmol) as suspension in dichloromethane (10 ml) was treated under argon at room temperature with triethylamine (4.2 mmol, 425 mg, 7 eq) and tetrahydro-4H-pyran-4-one (4.2 mmol, 420 mg, 7 eq). Then sodium triacetoxyborohydride (4.2 mmol, 890 mg, 7 eq) was added and the mixture was stirred overnight. Then 7 eq of fresh borohydride and the ketone were added again and stirred for 2 h 15 min. Methanol (3 mL) was added and stirred for 2 h. 7 eq of borohydride and the ketone were added again and stirred for 3.5 h. Then sodium cyanoborohydride (3 mmol, 188 mg, 5 eq) was added and the mixture was allowed to stand overnight. The mixture was loaded on an SCX cartridge, washed with methanol and eluted with 2M ammonia in methanol and dichloromethane. The eluate was concentrated under reduced pressure and chromatographed to give 5,6-dimethyl-1-[1-(tetrahydro-2H-pyran-4-yl)-4-piperidinyl]-1,3-dihydro-2H-benzimidazol-2-one as a white solid, which was transformed into the corresponding HCl salt. M+H=330.10, ¹H NMR (free base) (CDCl₃), δ: 9.29 (1H, s), 7.09 (1H, s), 6.89 (1H, s), 4.34 (1H, m), 4.06 (2H, dd), 3.41 (2H, t), 3.13 (2H, d), 2.56 (1H, m), 2.44 (4H, m), 2.28 (3H, s), 2.26 (3H, s), 1.87-1.60 (6H, m).

EXAMPLE 8

5-Bromo-6-methyl-1-[1-(tetrahydro-2H-pyran-4-yl)-4-piperidinyl]-1,3-dihydro-2H-benzimidazol-2-one hydrochloride (E8)

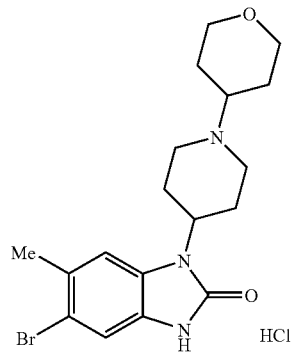

E8

5-Bromo-6-methyl-1-(4-piperidinyl)-1,3-dihydro-2H-benzimidazol-2-one (D37) (1.16 mmol, 359 mg) was dissolved in dichloromethane (20 mL) and tetrahydropyran-4-one (8.12 mmol, 7 eq, 813 mg), sodium triacetoxyborohydride (8.12 mmol, 1.72 g, 7 eq) and triethylamine (3.48 mmol, 352 mg, 3 eq, 0.48 ml) added. The reaction mixture was stirred at room temperature for 20 h. The reaction mixture was diluted with dichloromethane, washed with aqueous NaOH (pH 12), and the product extracted with dichloromethane (×2). The combined organic layers were washed with aqueous NaOH (pH 12), dried (MgSO₄) and the solvent removed under reduced pressure to afford the crude product. The product was purified by chromatography, eluting with 12+M, DCM/50% MeOH in DCM, 00%-50%, 8CVs), to afford 5-bromo-6-methyl-1-[1-(tetrahydro-2H-pyran-4-yl)-4-piperidinyl]-1,3-dihydro-2H-benzimidazol-2-one as a pale yellow solid (0.3 mmol, 111 mg, 26%). This was dissolved in dichloromethane (5 mL) and HCl (1M solution in ether) was added. The mixture was stirred at room temperature for 15 minutes. The solvents were removed under reduced pressure to afford the title compound as a white solid (0.02 mmol, 9 mg, 7%)

MH⁺=396.2.

EXAMPLE 9

5,6-Dichloro-1-[1-(tetrahydro-2H-pyran-4-yl)-4-piperidinyl]-1,3-dihydro-2H-benzimidazol-2-one hydrochloride (E9)

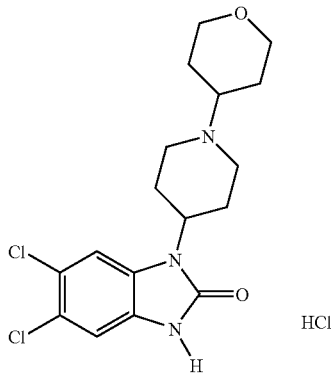

E9

N-(4,5-Dichloro-2-aminophenyl)-1-(tetrahydro-2H-pyran-4-yl)-4-piperidinamine (D39) (140 mg, 0.4 mmol) was dissolved in 10 ml of dichloromethane at 0° C. and phosgene (20% in toluene, 0.25 ml) and triethylamine (0.2 ml, 1.5 mmol) were added and the mixture was stirred at 0° C. for 1 h, then washed with aqueous sodium bicarbonate, dried over MgSO$_4$, filtered and evaporated The product was chromatographed on silica gel eluting with methanol-dichloromethane mixtures, and then further purified by MDAP to yield 5,6-dichloro-1-[1-(tetrahydro-2H-pyran-4-yl)-4-piperidinyl]-1,3-dihydro-2H-benzimidazol-2-one, 22 mg, which was converted into the hydrochloride salt using 4M HCl in dioxan.

MH$^+$=370, 372, and 374, $^1$H NMR (HCl salt) (DMSO-d6) δ: 1.72 (2H, m), 1.90 (2H, m), 2.02 (2H, m), 2.78 (2H, m), 3.18 (2H, m), 3.35 2H, m), 3.48 (1H, m), 4.01 (2H, m), 4.59 (1H, m), 6.52 (1H, d, J=12 Hz), 7.19 (1H, s), 7.88 (1H, s), 10.69 (1H, bs) and 11.42 (1H, s).

EXAMPLE 10

5-Chloro-6-methoxy-1-[1-(tetrahydro-2H-pyran-4-yl)-4-piperidinyl]-1,3-dihydro-2H-benzimidazol-2-one hydrochloride (E10)

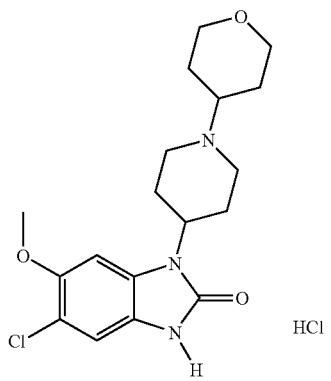

E10

6-Methoxy-5-chloro-1-(4-piperidinyl)-1,3-dihydro-2H-benzimidazol-2-one hydrochloride (D50) (30 mg, 0.1 mmol), Ti(iPrO)$_4$ (0.15 ml, 0.5 mmol), and tetrahydro-4H-pyran-4-one (50 mg, 0.5 mmol) were stirred together at room temperature for 1 h; dry methanol (1 ml) followed by NaBH$_3$CN (30 mg, 0.5 mmol) were added and the mixture was stirred at room temperature for 2 h. The crude mixture was then quenched with methanol and it was purified first by SCX column chromatography followed by silica gel chromatography (10% methanol-NH$_3$-dichloromethane) to afford 5-chloro-6-methoxy-1-[1-(tetrahydro-2H-pyran-4-yl)-4-piperidinyl]-1,3-dihydro-2H-benzimidazol-2-one. Conversion to the hydrochloride gave the title compound, 10 mg, MH$^+$=366 and 368.

$^1$H NMR. δ (DMSO-d6) 1.72 (2H, m), 1.90 (2H, m), 2.03 (2H, m), 2.81 (2H, m), 3.15 (2H, m), 3.56 (1H, m), 3.91 (3H, s), 3.96 (2H, m), 4.62 (1H, m), 7.01 (1H, s), 7.36 (1H, s), and 10.89 (2H, bs); remaining $^1$H signals not discernible in spectrum.

EXAMPLE 11

5-Fluoro-6-bromo-1-[1-(tetrahydro-2H-pyran-4-yl)-4-piperidinyl]-1,3-dihydro-2H-benzimidazol-2-one hydrochloride (E11)

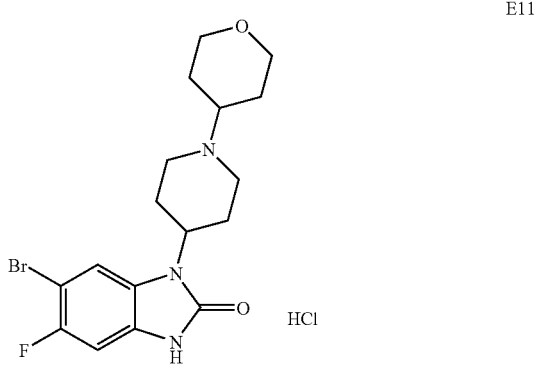

E11

To a stirred solution of fluoro-6-bromo-1-(4-piperidinyl)-1,3-dihydro-2H-benzimidazol-2-one (D46) (50 mg, 0.16 mmol), tetrahydro-4H-pyran-4-one (112 mg, 1.12 mmol) and triethylamine (49 mg, 0.48 mmol) in dichloromethane (5 ml) under argon was added portionwise sodium triacetoxyborohydride (240 mg, 1.12 mmol). The mixture was stirred at room temperature for 24 hrs, diluted with dichloromethane (5 ml) washed with 0.5N sodium hydroxide solution, dried (MgSO$_4$) and concentrated in approx half volume before adding to a silica gel column which was subsequently eluted with 2-20% methanol in dichloromethane to afford 5-fluoro-6-bromo-1-[1-(tetrahydro-2H-pyran-4-yl)-4-piperidinyl]-1,3-dihydro-2H-benzimidazol-2-one. The isolated product was converted to the hydrochloride salt which was obtained as a colourless solid, 34 mg, 49%. MH$^+$=398, and 400, $^1$H NMR (HCl salt) (DMSO-d6) δ: 1.24 (2H, m), 1.73 (3H, m), 1.89 (2H, m), 2.03 (2H, m), 2.83 (2H, m), 3.17 (2H, m), 3.58 (2H, m), 3.76 (1H, m), 4.59 (2H, m) 7.04 (1H, d, J=8 Hz) 7.94 (1H, d, J=5 Hz), 10.89 (1H, bs) and 11.32 (1H, s).

EXAMPLE 12

6-Chloro-5-trifluoromethyl-1-[1-(tetrahydro-2H-pyran-4-yl)-4-piperidinyl]-1,3-dihydro-2H-benzimidazol-2-one hydrochloride (E12)

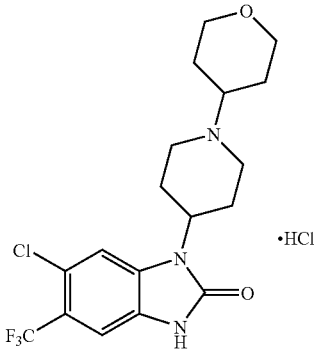

A stirred solution of 5-chloro-N-[1-(tetrahydro-2H-pyran-4-yl)-4-piperidinyl]-4-trifluoromethyl-1,2-benzenediamine (D52) (0.34 g, 0.9 mmol) in anhydrous tetrahydrofuran (40 ml) was treated with carbonyl diimidazole (0.29 g, 1.80 mmol)—added in portion over 5 minutes. The mixture was stirred at room temperature under argon for 4 hours. The mixture was warmed to a gentle reflux. After 18 hours, a further 0.29 g, 1.8 mmole of carbonyl diimidazole was added and the mixture maintained at reflux for another 24 hours. The mixture was cooled to room temperature and was treated with ethyl acetate (40 ml) and washed with water and brine then dried over MgSO$_4$ and concentrated to dryness. The residue was purified by silica gel chromatography eluting with 1 to 10% methanol in dichloromethane to afford 6-chloro-5-trifluoromethyl-1-[1-(tetrahydro-2H-pyran-4-yl)-4-piperidinyl]-1,3-dihydro-2H-benzimidazol-2-one, which was subsequently converted to the hydrochloride salt and isolated as a cream powder. 0.25 g, 73%. MH$^+$=404 and 406

$^1$H NMR (HCl salt) δ(DMSO-d6) 1.75 (2H, m), 1.94 (2H, m), 2.05 (2H, m), 2.84 (2H, m), 3.17 (2H, m), 3.33 (2H, m; partially obscured by H$_2$O signal), 3.43 (1H, m), 3.62 (2H, m), 4.01 (2H, m), 4.63 (1H, m), 7.33 (1H, s), 8.27 (1H, s), 10.88 (1H, bs) and 11.50 (1H, s).

EXAMPLE 13

6-Bromo-1-[1-(tetrahydro-2H-pyran-4-yl)-4-piperidinyl]-5-(trifluoromethyl)-1,3-dihydro-2H-benzimidazol-2-one hydrochloride (E13)

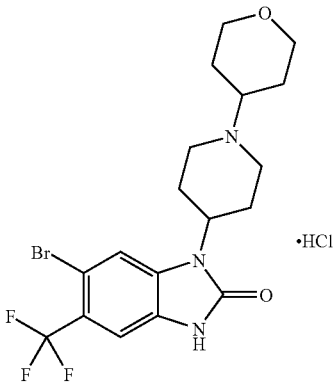

A stirred solution of 5-bromo-N-[1-(tetrahydro-2H-pyran-4-yl)-4-piperidinyl]-4-(trifluoromethyl)-1,2-benzenediamine (D55) (0.34 mmol) in tetrahydrofuran (8 ml) at room temperature under argon was treated with diisopropylethylamine (0.12 ml, 0.68 mmol) followed by ethyl chloroformate (40 mg, 0.38 mmol) and then heated under reflux for 2 hrs. The mixture was concentrated under vacuum and the residue dissolved in dimethylformamide, treated with more diisopropylethylamine (0.12 ml) and heated at 150° C. for 0.75 hr. The solution was then concentrated under vacuum and the residue treated with 10% Na$_2$CO$_3$ solution and extracted with ethyl acetate. The extract was dried and concentrated under vacuum. The residue was triturated with diethyl ether to afford 6-bromo-1-[1-(tetrahydro-2H-pyran-4-yl)-4-piperidinyl]-5-(trifluoromethyl)-1,3-dihydro-2H-benzimidazol-2-one as a beige solid. This was converted to its HCl salt as a beige solid (55 mg, 33%). MH$^+$=448, 450.

$^1$H NMR free base (400 MHz, d$^6$DMSO) δ: 1.39-1.52 (m, 2H), 1.62-1.75 (m, 4H), 2.20-2.40 (m, 4H), 2.45-2.55 (m, 1H), 2.94-3.08 (m, 2H), 3.23-3.35 (m, 2H), 3.85-3.95 (m, 2H), 4.10-4.22 (m, 1H), 7.30 (s, 1H), 7.71 (s, 1H), 11.30 (br s, 1H).

EXAMPLE 14

6-Methyl-1-[1-(tetrahydro-2H-pyran-4-yl)-4-piperidinyl]-5-(trifluoromethyl)-1,3-dihydro-2H-benzimidazol-2-one hydrochloride (E14)

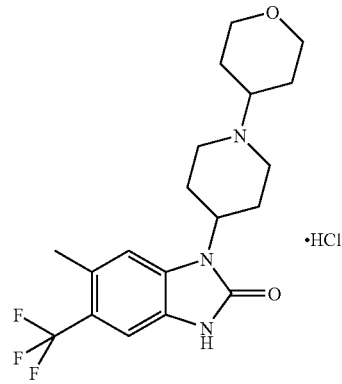

6-Methyl-1-(4-piperidinyl)-5-(trifluoromethyl)-1,3-dihydro-2H-benzimidazol-2-one hydrochloride (D60) (2.2 mmol), was dissolved in 1,2-dichloroethane (50 ml) and triethylamine (7 ml), tetrahydro-4H-pyran-4-one (7 eq., 15.4 mmol, 1.4 ml), sodium triacetoxyborohydride (7 eq., ~3.2 g) were added in that order at room temperature and the mixture was stirred at room temperature for 2 hours. Reaction mixture was quenched with 10 ml of NaHCO$_3$ (saturated solution) and diluted with dichloromethane; the two phases were separated and the organic solvent was evaporated to afford the crude product. The crude obtained was dissolved again in 1,2-dichloroethane (50 ml) and triethylamine (7 ml), tetrahydro-4H-pyran-4-one (7 eq., 15.4 mmol, 1.4 ml), sodium triacetoxyborohydride (7 eq., ~3.2 g) were added at room temperature and the mixture was stirred at room temperature for three hours. Reaction mixture was quenched with 10 ml of NaHCO$_3$ (saturated solution) and diluted with dichloromethane; the two phases were separated and the organic solvent was evaporated to afford the crude product that was purified by chromatography (methanol-NH$_3$-dichloromethane) to afford 6-methyl-1-[1-(tetrahydro-2H-pyran-4-yl)-4-piperidinyl]-5-(trifluoromethyl)-1,3-dihydro-2H-benzimidazol-2-one, 240 mg, 30%, M$^+$+H=384, which was subsequently converted into the hydrochloride salt using HCl solution (1M in diethyl ether, 2 eq).

$^1$HNMR δ (DMSO, 400 MHz, free base) 1.459 (2H, m), 1.688 (4H, t), 2.291 (4H, m), 2.452 (3H, s), 3.023 (2H, d), 3.252 (2H, t), 3.903 (2H, dd), 4.112 (1H, m broad), 7.161 (1H, d), 7.291 (1H, d), 11.1 (1H, s broad); remaining $^1$H signals not discernible in spectrum

EXAMPLE 15

6-Chloro-1-[1-(4-methyltetrahydro-2H-pyran-4-yl)-4-piperidinyl]-5-(trifluoromethyl)-1,3-dihydro-2H-benzimidazol-2-one hydrochloride (E15)

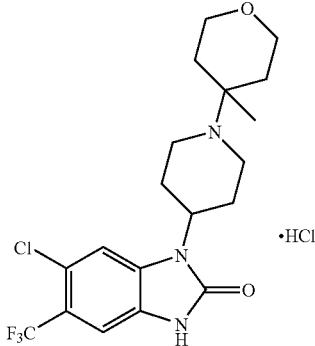

E15

A solution of 4-{4-[6-chloro-2-oxo-5-(trifluoromethyl)-2,3-dihydro-1H-benzimidazol-1-yl]-1-piperidinyl}tetrahydro-2H-pyran-4-carbonitrile (D65, 1160 mg, 0.37 mmol) in tetrahydrofuran (5 ml) was treated with methylmagnesium bromide (3M in diethyl ether, 1.0 ml, 3.0 mmol). After 2 h at room temperature the solution was partitioned between aqueous Rochelle salt solution and dichloromethane, and the organic layer was dried (MgSO$_4$) and evaporated The residue was chromatographed on silica gel eluting with methanol-dichloromethane mixtures to afford the title compound, which was isolated as the hydrochloride salt triturated from diethyl ether (110 mg). MH$^+$=418 and 420, $^1$H NMR (HCl salt) δ (d$^6$DMSO): 1.4 (3H, s), 2.0 (6H, m), 2.8 (2H, m), 3.2 (2H, m), 3.4 (2H, m), 3.6 (2H, m), 3.9 (2H, m), 4.7 (1H, m), 7.3 (1H, s), 7.9 (1H, s), 10.30 (1H, bs) and 11.5 (1H, s).

EXAMPLE 16

6-Bromo-1-[1-(4-methyltetrahydro-2H-pyran-4-yl)-4-piperidinyl]-5-(trifluoromethyl)-1,3-dihydro-2H-benzimidazol-2-one hydrochloride (E16)

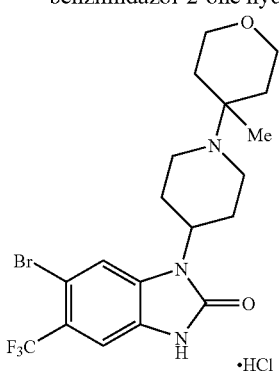

E16

A stirred suspension of 4-{4-[6-bromo-2-oxo-5-(trifluoromethyl)-2,3-dihydro-1H-benzimidazol-1-yl]-1-piperidinyl}tetrahydro-2H-pyran-4-carbonitrile (D70, 1100 mg, 0.21 mmol) in tetrahydrofuran (8 ml) at room temperature under argon was treated with 3M methylmagnesium bromide solution in diethyl ether (0.15 ml, 0.46 mmol) and the insoluble material rapidly dissolved. Further methylmagnesium bromide solution was added after a total of 50 minutes (0.15 ml) and a total of 70 minutes (0.20 ml). After another 15 minutes the reaction mixture was cooled to 0° C. and treated dropwise with 1M aq. NH$_4$Cl solution (3 ml), then diluted with water (15 ml) and extracted with ethyl acetate. The extract was washed with brine, dried (Na$_2$SO$_4$) and concentrated under vacuum to afford the title compound as a white solid. This was converted to its HCl salt as a white solid (95 mg, 90%).

$^1$H NMR (free base) δ (CDCl$_3$, 400 MHz): 10.37 (1H, br s), 7.55 (1H, s), 7.46 (1H, s), 4.37-4.24 (1H, m), 3.98-3.90 (2H, m), 3.62-3.53 (2H, m), 3.16 (2H, d), 2.38-2.25 (4H, m), 1.92-1.75 (4H, m), 1.62-1.52 (2H, m), 1.04 (3H, s).

EXAMPLE 17

6-Methyl-1-[1-(4-methyltetrahydro-2H-pyran-4-yl)-4-piperidinyl]-5-(trifluoromethyl)-1,3-dihydro-2H-benzimidazol-2-one hydrochloride (E17)

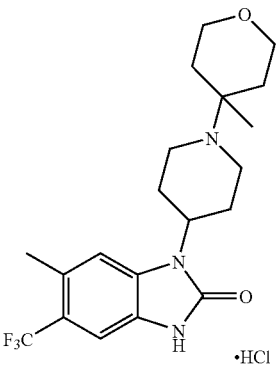

E17

4-{4-[6-Methyl-2-oxo-5-(trifluoromethyl)-2,3-dihydro-1H-benzimidazol-1-yl]-1-piperidinyl}tetrahydro-2H-pyran-4-carbonitrile (D71, 200 mg, 0.47 mmol) was dissolved in dry tetrahydrofuran (10 ml) and MeMgBr (5 eq., 2.3 mmol, ~0.8 ml) was added at room temperature and the mixture stirred at room temperature for 2 hours. MeMgBr (5 eq.) was added again and the mixture stirred at room temperature overnight. The mixture was cooled to 0° C. and quenched with NH$_4$Cl solution. The tetrahydrofuran was removed by reduced pressure and water was added, then the aqueous mixture was extracted with dichloromethane followed by ethyl acetate. The organics were combined and the solvent was evaporated to afford the title compound which was purified by chromatography (ethyl acetate-n-hexane) to afford a white solid, 50 mgs, 26%. The title compound was subsequently converted into the hydrochloride salt using HCl solution (1M in Et$_2$O, 2 eq.).

$^1$H NMR δ (d$^6$DMSO, 400 MHz, free base): 0.955 (3H, s), 1.470 (2H, m, broad), 1.681 (4H, m), 2.170 (2H, t), 2.294 (2H, m), 2.458 (3H, s), 3.053 (2H, d), 3.438 (2H, m), 3.764 (2H, m), 4.106 (1H, m), 7.161 (1H, s), 7.288 (1H, s), 11.1 (1H, s broad).

EXAMPLE 18

5-Fluoro-6-methyl-1-[1-(4-methyltetrahydro-2H-pyran-4-yl)piperidin-4-yl]-1,3-dihydro-2H-benzimidazol-2-one hydrochloride (E18)

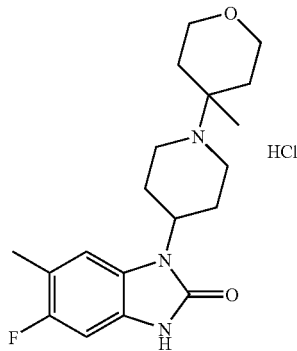

4-[4-(5-Fluoro-6-methyl-2-oxo-2,3-dihydro-1H-benzimidazol-1-yl)piperidin-1-yl]tetrahydro-2H-pyran-4-carbonitrile (D72, 300 mg) in tetrahydrofuran (10 ml) was treated with methylmagnesium bromide 3M solution in tetrahydrofuran (1.4 ml) over 5 minutes and stirred for 1 hours then treated with saturated ammonium chloride solution (5 ml). The mixture was treated with dichloromethane and water. The dichloromethane layer was separated, dried by passing through a hydromatrix cartridge and the solvent was removed. The white solid from Et$_2$O was dissolved in a mixture of methanol and dichloromethane and treated with hydrogen chloride in ether. The solvent was removed and the title compound as a white solid (211 mg) from ether. M$^+$ 348

$^1$H NMR (HCl salt) δ (d$^6$DMSO): 1.39 (3H, s), 1.9 (4H, m), 2.10 (2H, m), 2.24 (3H, s), 2.87 (2H, m), 3.20 (2H, m), 3.45 (2H, m), 3.6 (obscured), 3.9 (2H, m), 4.6 (1H, m), 6.80 (1H, d), 7.68 (1H, d) 10.25 (1H, s), 10.9 (1H, s).

$^{19}$F NMR δ (d$^6$DMSO): 125.69

EXAMPLE 19

6-Methyl-5-[(1-methylethyl)oxy]-1-[1-(tetrahydro-2H-pyran-4-yl)-4-piperidinyl]-1,3-dihydro-2H-benzimidazol-2-one hydrochloride (E19)

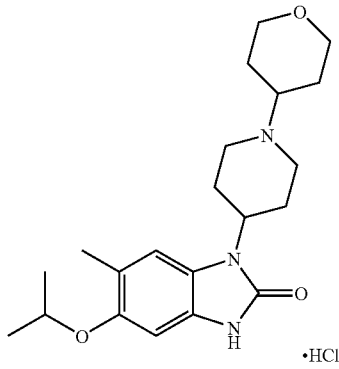

A solution of 6-methyl-5-[(1-methylethyl)oxy]-1-(4-piperidinyl)-1,3-dihydro-2H-benzimidazol-2-one (D77) (assumed 0.14 mmol—crude material) in dichloromethane (2 mL) was treated with tetrahydro-4H-pyran-4-one (1.4 mmol, 140 mg, 10 eq) and triethylamine (1.4 mmol, 141.7 mg, 10 eq) at room temperature under argon, then sodium triacetoxyborohydride (1.4 mmol, 296.8 mg, 10 eq) was added and the mixture was allowed to stir for 3 h and to stand overnight. The mixture was diluted with dichloromethane and treated with aqueous sodium hydroxide so that the pH was maintained around 12. The aqueous phase was extracted, the organics were combined, washed with aqueous sodium hydroxide solution (pH~12), dried and concentrated under reduced pressure. The residue was purified by chromatography (methanol/dichloromethane, 0-10% 5CV) to give a gum, which was dissolved in dichloromethane and methanol, treated with ethereal hydrogen chloride, then concentrated under reduced pressure to give the title compound as its hydrochloride salt-white solid (0.071 mmol, 29 mg, 51% yield). M+H 374.1.

EXAMPLE 20

6-Ethyl-5-fluoro-1-[1-(tetrahydro-2H-pyran-4-yl)-4-piperidinyl]-1,3-dihydro-2H-benzimidazol-2-one hydrochloride (E20)

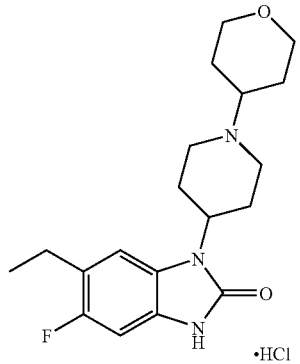

A stirred solution of (2-amino-5-ethyl-4-fluorophenyl)-[1-(tetrahydro-2H-pyran-4-yl)-4-piperidinyl]amine (D80, 230 mg, 0.71 mmol) in dichloromethane (10 ml) at room temperature under argon was treated with carbonyl diimidazole (345 mg, 2.13 mmol) and stirred overnight under argon. The mixture was washed with water and extracted with dichloromethane. The organic fractions were collected and dried over MgSO$_4$ and concentrated under vacuum. The solid residue was recrystallised from diethyl ether and collected by filtration to afford 140 mg of clean free base (0.4 mmol, 57% yield). The free base was dissolved in methanol and 1M HCl in diethyl ether solution (1 ml) was added. The hydrochloride salt was recovered by evaporation of the solvent. MH$^+$=348 and 349.

$^1$H NMR (HCl salt) δ (CD$_3$OD, 400 MHz): 1.3 (3H, t), 1.85 (2H, m), 2.1 (4H, m), 2.7 (2H, m), 2.85 (2H, q) 3.25 (2H, m), 3.5 (3H, m), 3.75 (2H, m), 4.1 (2H, m), 4.55 (1H, m), 6.8 (1H, d), 7.2 (1H, d); remaining $^1$H signals not discernible in spectrum.

EXAMPLE 21

6-Cyclopropyl-5-fluoro-1-[1-(tetrahydro-2H-pyran-4-yl)-4-piperidinyl]-1,3-dihydro-2H-benzimidazol-2-one hydrochloride (E21)

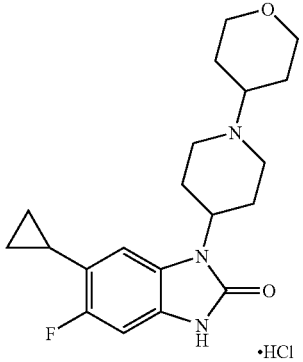

E21

A stirred mixture of 5-cyclopropyl-4-fluoro-N-[1-(tetrahydro-2H-pyran-4-yl)-4-piperidinyl]-1,2-benzenediamine (D82, 0.33 g, 1.0 mmol) and carbonyl diimidazole (0.32 g, 2.0 mmol) in anhydrous tetrahydrofuran (20 ml) was heated under reflux for 8 hrs. The mixture was cooled, diluted with ethyl acetate (25 ml) and washed with water (×4) and brine (×2), then dried (MgSO$_4$) and concentrated under vacuum. The residue was triturated with diethyl ether, and the solid filtered off and dried under vacuum to afford the title compound as a cream coloured solid (242 mg, 67%). This was suspended in ethanol (8 ml) and treated with 1M HCl/diethyl ether (3 ml) to give a clear solution, which was concentrated under vacuum to dryness to give the HCl salt of the title compound as a cream coloured powder. M+H 360.0.

$^1$H NMR (HCl salt) δ (CD$_3$OD, 400 MHz): 0.75-0.80 (2H, m), 0.93-1.00 (2H, m), 1.78-1.90 (2H, m), 2.03-2.20 (5H, m), 2.78-2.92 (2H, m), 3.20-3.35 (2H, m), 3.40-3.60 (3H, m), 3.70-3.80 (2H, m), 4.10 (2H, dd), 4.50-4.62 (1H, m), 6.80 (1H, d), 6.93 (1H, d).

EXAMPLE 22

5-Chloro-6-[(1-methylethyl)oxy]-1-[1-(tetrahydro-2H-pyran-4-yl)-4-piperidinyl]-1,3-dihydro-2H-benzimidazol-2-one hydrochloride (E22)

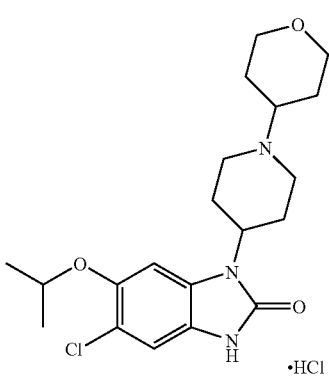

E22

A solution of 5-chloro-6-[(1-methylethyl)oxy]-1-(4-piperidinyl)-1,3-dihydro-2H-benzimidazol-2-one (D87, 94 mg, 0.30 mmol) in dichloromethane (3 ml) was treated with tetrahydro-4H-pyran-4-one (0.213 g, 0.21 mmol, 7 eq), sodium triacetoxyborohydride (0.445 g, 0.21 mmol, 7 eq) and triethylamine (0.101 g, 1 mmol, 3 eq) and stirred at room temperature under argon overnight. The mixture was diluted with dichloromethane and washed with aqueous NaOH solution (pH12). The NaOH wash was extracted with dichloromethane (×2) and the combined extracts was washed with aqu, NaOH solution, dried (MgSO$_4$) and concentrated under vacuum. The residue was purified by MDAP to afford the title compound as a white solid (14 mg, 0.04 mol, 13%). M$^+$+H=394.2.

$^1$H NMR (HCl salt) δ(d$^6$DMSO, 400 MHz): 1.27 (6H, d), 1.68-1.80 (2H, m), 1.93 (2H, br d), 2.02 (2H, br d), 2.72-2.87 (2H, m), 3.10-3.22 (2H, m), 3.55-3.66 (2H, m), 3.99 (2H, br d), 4.5-4.60 (1H, m), 4.65-4.75 (1H, m), 7.00 (1H, s), 7.32 (1H, s), 10.35 (1H, br s), 11.00 (1H, s). Remaining 1H not discernible from spectrum.

EXAMPLE 23

5,6-Difluoro-1-[1-(tetrahydro-2H-pyran-4-yl)-4-piperidinyl]-1,3-dihydro-2H-benzimidazol-2-one hydrochloride (E23)

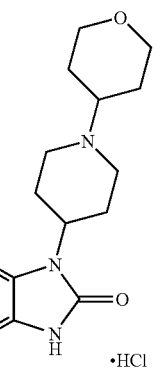

E23

A solution of 5,6-difluoro-1-(4-piperidinyl)-1,3-dihydro-2H-benzimidazol-2-one acetate salt (D89, 0.51 mmol, 159 mg) in tetrahydrofuran (10 mL) was treated with triethylamine (2.55 mmol, 258 mg, 5 eq) and tetrahydro-4H-pyran-4-one (2.55 mmol, 255 mg, 5 eq) under argon at room temperature, then sodium cyanoborohydride (2.55 mmol, 160 mg, 5 eq) was added. The mixture was stirred at room temperature overnight, then methanol (5 mL) was added and stirred for 4 h. The mixture was allowed to stand for 7 days, then acetic acid (10 eq) was added, stirred for 1 h and the mixture stood over the weekend. The mixture was concentrated under vacuum and the title compound was isolated as a white solid from the residue by SCX cartridge, then transformed into its hydrochloride salt (1 ml HCl/ether (1M)+5 ml DCM), white solid (0.14 mmol, 53 mg, 28% overall yield). M+H 338.2, $^1$H NMR (HCl salt) δ(D$_2$O): 7.15 (1H, t), 7.0 (1H, t), 4.4 (1H, m), 4.0 (2H, dd), 3.68 (2H, d), 3.5 (3H, m), 3.13 (2H, t), 2.6 (2H, dq), 2.1 (2H, d), 2.0 (2H, d), 1.75 (2H, dq).

EXAMPLE 24

6-Methyl-2-oxo-1-[1-(tetrahydro-2H-pyran-4-yl)-4-piperidinyl]-2,3-dihydro-1H-benzimidazole-5-carbonitrile hydrochloride (E24)

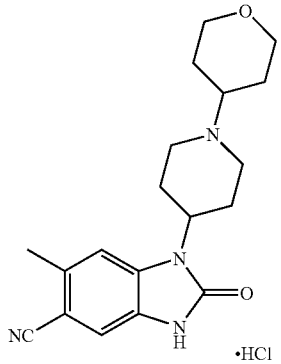

E24

A solution of 6-methyl-2-oxo-1-(4-piperidinyl)-2,3-dihydro-1H-benzimidazole-5-carbonitrile (D94) (μmol, 256 mg) in dichloromethane (10 mL) was treated with tetrahydro-4H-pyran-4-one (10 mmol, 1.0 g, 10 eq) and triethylamine (3 mmol, 303.6 mg, 3 eq) at room temperature under argon, then sodium triacetoxyborohydride (10 mmol, 2.12 g, 10 eq) was added and the mixture was allowed to stir for 6.5 h and to stand overnight. The mixture was diluted with dichloromethane and treated with aqueous sodium hydroxide so that the pH was maintained around 12. The aqueous phase was extracted with dichloromethane and the organics were combined, washed with an aqueous sodium hydroxide solution (pH ~12), dried and concentrated under reduced pressure. The residue was purified by chromatography (methanol/dichloromethane) to give a gum which was dissolved in dichloromethane and methanol, treated with hydrogen chloride (in ether, 2M) then concentrated under reduced pressure to give the title compound as its hydrochloride salt-beige solid (0.22 mmol, 83 mg, 22% yield). M+H 341.1.

$^1$H NMR (HCl salt) δ (DMSO, 400 MHz): 11.27 (1H, s), 10.7 (1H, s), 7.81 (1H, s), 7.32 (1H, s), 4.6 (1H, m), 4.0 (2H, dd), 3.6 (2H, d), 3.3 (2H, m), 3.17 (2H, m), 2.83 (2H, q), 2.03 (2H, d), 1.92 (2H, d), 1.74 (2H, m).

EXAMPLE 25

6-Chloro-5-(difluoromethyl)-1-[1-(tetrahydro-2H-pyran-4-yl)-4-piperidinyl]-1,3-dihydro-2H-benzimidazol-2-one hydrochloride (E25)

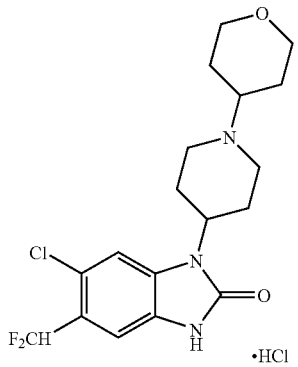

E25

A stirred solution of 5-chloro-4-(difluoromethyl)-N-[1-(tetrahydro-2H-pyran-4-yl)-4-piperidinyl]-1,2-benzenediamine (D98, 180 mg, 0.50 mmol) in tetrahydrofuran (8 ml) at room temperature under argon was treated with N,N-diisopropylethylamine (0.18 ml, 1.0 mmol) followed by ethyl chloroformate (65 mg, 0.60 mmol) and maintained for 1 hr. The solution was concentrated under vacuum and the residue dissolved in dimethylformamide (5 ml) and heated at 150° C. under argon for 1.5 hrs. The solution was concentrated under vacuum and the residue treated with 10% $Na_2CO_3$ solution and extracted with ethyl acetate. The extract was dried and concentrated under vacuum to leave an orange solid, which was washed with diethyl ether. The remaining solid was converted to its HCl salt, which was again washed with diethyl ether to afford the HCl salt of the title compound as a pale yellow solid (92 mg, 47%).

$^1$H NMR (free base) δ ($CDCl_3$, 400 MHz): 1.55-1.95 (6H, m), 2.30-2.45 (4H, m), 2.52-2.65 (1H, m), 3.10-3.20 (2H, m), 3.41 (2H, t), 4.00-4.12 (2H, m), 4.28-4.40 (1H, m), 6.99 (1H, t, J=54 Hz), 7.35 (1H, s), 7.39 (1H, s), 10.04 (1H, br s).

EXAMPLE 26

5,6-Dimethyl-1-[1-(4-methyltetrahydro-2H-pyran-4-yl)-4-piperidinyl]-1,3-dihydro-2H-benzimidazol-2-one hydrochloride (E26)

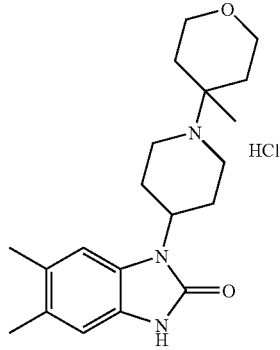

E26

A solution of 5,6-dimethyl-1-[1-(4-methyltetrahydro-2H-pyran-4-yl)-1,2,3,6-tetrahydro-4-pyridinyl]-1,3-dihydro-2H-benzimidazol-2-one (D102) as hydrochloride salt (0.2 mmol, 75 mg) in methanol (7 ml) was treated under argon with 10% palladium on charcoal and shaken under 50 PSI of hydrogen pressure for 4 days. The catalyst was filtered off and the mixture was concentrated to give the title compound as a white solid (0.07 mmol, 27 mg, 35% yield). M+H 344.3

$^1$H NMR (HCl salt) δ (DMSO, 400 MHz): 10.65 (1H, s), 7.68 (1H, s), 6.77 (1H, s), 4.61 (1H, t), 3.88 (2H, dd), 3.59 (2H, d), 3.44 (2H, t), 3.17 (2H, q), 2.95 (2H, q), 2.23 (3H, s), 2.19 (3H, s), 1.83 (integration unclear, m), 1.35 (3H, d).

All $^1$H & $^{19}$F NMR are consistent with the structures shown.

All publications, including but not limited to patents and patent applications, cited in this specification are herein incorporated by reference as if each individual publication were specifically and individually indicated to be incorporated by reference herein as though fully set forth.

The application of which this description and claims forms part may be used as a basis for priority in respect of any subsequent application. The claims of such subsequent application may be directed to any feature or combination of features described herein. They may take the form of product, composition, process or use claims and may include, by way of example and without limitation, one or more of the following claims:

The invention claimed is:
1. A compound of formula (I) or a salt thereof:

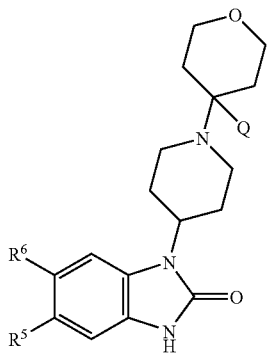

wherein:
R$^5$ is selected from halogen, C$_{1-6}$alkyl, C$_{1-6}$alkyl substituted with one or more fluorine atoms, C$_{1-6}$alkoxy, C$_{1-6}$alkoxy substituted with one or more fluorine atoms, and cyano;
R$^6$ is selected from halogen, C$_{1-6}$alkyl, C$_{1-6}$alkyl substituted with one or more fluorine atoms, C$_{3-6}$cycloalkyl, C$_{3-6}$cycloalkyl substituted with one or more fluorine atoms, C$_{1-6}$ alkoxy, C$_{1-6}$ alkoxy substituted with one or more fluorine atoms, and cyano; and
Q is hydrogen or C$_{1-6}$alkyl.

2. A compound as claimed in claim 1 wherein R$^5$ is selected from halogen, C$_{1-4}$alkyl, C$_{1-4}$alkyl substituted with one or more fluorine atoms, C$_{1-4}$alkoxy, C$_{1-4}$alkoxy substituted with one or more fluorine atoms, and cyano.

3. A compound as claimed in claim 1 wherein R$^5$ is selected from fluoro, chloro, bromo, methyl, methoxy, methylethyloxy, cyano, difluoromethyl and trifluoromethyl.

4. A compound as claimed in claim 1 wherein R$^6$ is selected from chloro, bromo, fluoro, C$_{1-4}$alkyl, C$_{1-4}$alkyl substituted with one or more fluorine atoms, C$_{3-6}$cycloalkyl, C$_{1-4}$alkoxy, and C$_{1-4}$alkoxy substituted with one or more fluorine atoms.

5. A compound as claimed in wherein R$^6$ is selected from chloro, bromo, fluoro, methyl, ethyl, isopropyl, cyclopropyl, methoxy, methylethyloxy, trifluoromethoxy and trifluoromethyl.

6. A compound as claimed in claim 1 wherein Q is hydrogen or methyl.

7. A compound as claimed in claim 1 which is selected from:
6-Chloro-5-fluoro-1-[1-(tetrahydro-2H-pyran-4-yl)-4-piperidinyl]-1,3-dihydro-2H-benzimidazol-2-one
6-Chloro-5-methyl-1-[1-(tetrahydro-2H-pyran-4-yl)-4-piperidinyl]-1,3-dihydro-2H-benzimidazol-2-one
6-Chloro-1-[1-(tetrahydro-2H-pyran-4-yl)-4-piperidinyl]-5-(trifluoromethyl)-1,3-dihydro-2H-benzimidazol-2-one
6-Methyl-5-(methyloxy)-1-[1-(tetrahydro-2H-pyran-4-yl)-4-piperidinyl]-1,3-dihydro-2H-benzimidazol-2-one
5-Chloro-6-methyl-1-[1-(tetrahydro-2H-pyran-4-yl)-4-piperidinyl]-1,3-dihydro-2H-benzimidazol-2-one
5-Fluoro-6-methyl-1-[1-(tetrahydro-2H-pyran-4-yl)-4-piperidinyl]-1,3-dihydro-2H-benzimidazol-2-one 5,6-Dimethyl-1-[1-(tetrahydro-2H-pyran-4-yl)-4-piperidinyl]-1,3-dihydro-2H-benzimidazol-2-one
5-Bromo-6-methyl-1-[1-(tetrahydro-2H-pyran-4-yl)-4-piperidinyl]-1,3-dihydro-2H-benzimidazol-2-one
5,6-Dichloro-1-[1-(tetrahydro-2H-pyran-4-yl)-4-piperidinyl]-1,3-dihydro-2H-benzimidazol-2-one
5-Chloro-6-methoxy-1-[1-(tetrahydro-2H-pyran-4-yl)-4-piperidinyl]-1,3-dihydro-2H-benzimidazol-2-one
5-Fluoro-6-bromo-1-[1-(tetrahydro-2H-pyran-4-yl)-4-piperidinyl]-1,3-dihydro-2H-benzimidazol-2-one
6-Chloro-5-trifluoromethyl-1-[1-(tetrahydro-2H-pyran-4-yl)-4-piperidinyl]-1,3-dihydro-2H-benzimidazol-2-one
6-Bromo-1-[1-(tetrahydro-2H-pyran-4-yl)-4-piperidinyl]-5-(trifluoromethyl)-1,3-dihydro-2H-benzimidazol-2-one, or
6-Methyl-1-[1-(tetrahydro-2H-pyran-4-yl)-4-piperidinyl]-5-(trifluoromethyl)-1,3-dihydro-2H-benzimidazol-2-one
6-Chloro-1-[1-(4-methyltetrahydro-2H-pyran-4-yl)-4-piperidinyl]-5-(trifluoromethyl)-1,3-dihydro-2H-benzimidazol-2-one
6-Bromo-1-[1-(4-methyltetrahydro-2H-pyran-4-yl)-4-piperidinyl]-5-(trifluoromethyl)-1,3-dihydro-2H-benzimidazol-2-one
6-Methyl-1-[1-(4-methyltetrahydro-2H-pyran-4-yl)-4-piperidinyl]-5-(trifluoromethyl)-1,3-dihydro-2H-benzimidazol-2-one
5-Fluoro-6-methyl-1-[1-(4-methyltetrahydro-2H-pyran-4-yl)piperidin-4-yl]-1,3-dihydro-2H-benzimidazol-2-one
6-Methyl-5-[(1-methylethyl)oxy]-1-[1-(tetrahydro-2H-pyran-4-yl)-4-piperidinyl]-1,3-dihydro-2H-benzimidazol-2-one
6-Ethyl-5-fluoro-1-[1-(tetrahydro-2H-pyran-4-yl)-4-piperidinyl]-1,3-dihydro-2H-benzimidazol-2-one 6-Cyclopropyl-5-fluoro-1-[1-(tetrahydro-2H-pyran-4-yl)-4-piperidinyl]-1,3-dihydro-2H-benzimidazol-2-one
5-Chloro-6-[(1-methylethyl)oxy]-1-[1-(tetrahydro-2H-pyran-4-yl)-4-piperidinyl]-1,3-dihydro-2H-benzimidazol-2-one
5,6-Difluoro-1-[1-(tetrahydro-2H-pyran-4-yl)-4-piperidinyl]-1,3-dihydro-2H-benzimidazol-2-one
6-Methyl-2-oxo-1-[1-(tetrahydro-2H-pyran-4-yl)-4-piperidinyl]-2,3-dihydro-1H-benzimidazole-5-carbonitrile
6-Chloro-5-(difluoromethyl)-1-[1-(tetrahydro-2H-pyran-4-yl)-4-piperidinyl]-1,3-dihydro-2H-benzimidazol-2-one
5,6-Dimethyl-1-[1-(4-methyltetrahydro-2H-pyran-4-yl)-4-piperidinyl]-1,3-dihydro-2H-benzimidazol-2-one
and salts thereof.

8. A pharmaceutical composition comprising a compound as claimed in claim 1, and a pharmaceutically acceptable carrier thereof.

9. A method of treating a psychotic disorder or cognitive impairment, which comprises administering to a mammal in need thereof an effective amount of a compound as claimed in claim 1.

10. A process for preparing a compound of formula (I) or a salt thereof as defined in claim 1, which process is selected from:

process (A1) which comprises coupling a compound of formula (II)

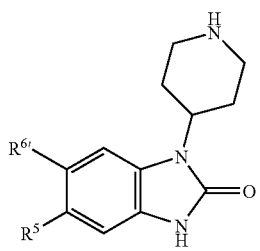
(II)

with a compound of formula (III)

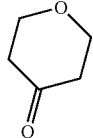
(III)

wherein $R^{5'}$ is a group $R^5$ as defined in claim 1, or a group convertible to $R^5$ and $R^{6'}$ is a group $R^6$ as defined in claim 1, or a group convertible to $R^6$, under conditions suitable for reductive alkylation;

and process (A2) which comprises reacting a compound of formula (II) with a compound of formula (III) in the presence of a source of cyanide to form the cyano intermediate (XXXX) which can be reacted with an alkyl Grignard reagent QMgX to form compounds of formula (I);

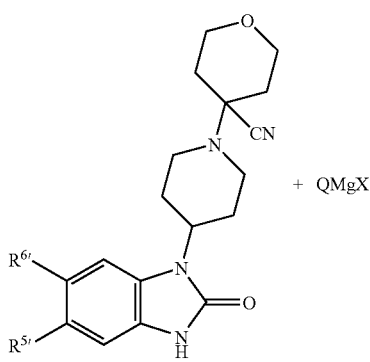
(XXXX)

wherein $R^{5'}$ is a group $R^5$ as defined in claim 1, or a group convertible to $R^5$, $R^{6'}$ is a group $R^6$ as defined in claim 1, or a group convertible to $R^6$, and Q is hydrogen or $C_{1-6}$alkyl under conditions suitable for Grignard reactions;

and process (B) which comprises coupling a compound of formula (IV)

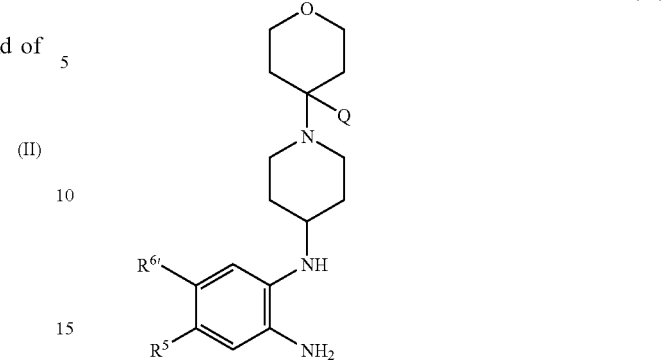
(IV)

with a compound of formula (V)

(V)

wherein $R^{5'}$ is a group $R^5$ as defined in claim 1, or a group convertible to $R^5$ and $R^{6'}$ is a group $R^6$ as defined in claim 1, or a group convertible to $R^6$, Q is hydrogen or $C_{1-6}$alkyl; and X and Y both represent leaving groups optionally in an inert solvent, optionally in the presence of a base, and optionally with heating;

and process (C) which comprises treatment of a compound of formula (VI)

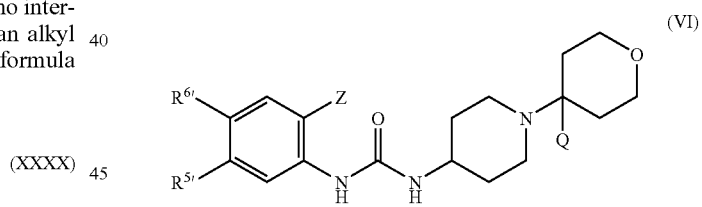
(VI)

with a palladium or copper catalyst (VII) to effect an intramolecular cyclisation, wherein $R^{5'}$ is a group $R^5$ as defined in claim 1, or a group convertible to $R^5$ and $R^{6'}$ is a group $R^6$ as defined in claim 1, or a group convertible to $R^6$, Q is hydrogen or $C_{1-6}$alkyl; and Z is a leaving group such as bromo, iodo, chloro or triflate;

and process (D) which comprises coupling a compound of formula (VIII)

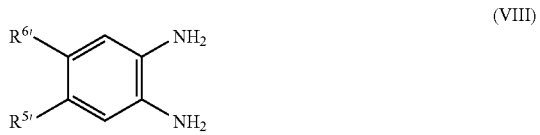
(VIII)

with a compound of formula (IX)

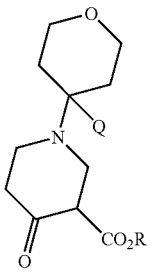

(IX)

wherein R⁵' is a group R⁵ as defined in claim 1, or a group convertible to R⁵ and R⁶' is a group R⁶ as defined in claim 1, or a group convertible to R⁶, Q is hydrogen or $C_{1-6}$alkyl; and R is a $C_{1-5}$ alkyl group by heating in an inert solvent, for example xylene, followed by reduction of the piperidine double bond;
and
  process (E) which comprises reaction of a compound of formula (X)

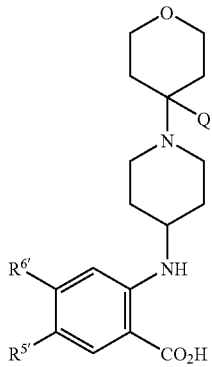

(X)

with a reagent/combination of reagents to effect the Curtius rearrangement of compound (X), followed by intramolecular cyclisation;
wherein R⁵' is a group R⁵ as defined in claim 1, or a group convertible to R⁵ and R⁶' is a group R⁶ as defined in claim 1, or a group convertible to R⁶ and Q is hydrogen or $C_{1-6}$alkyl; and
  process (F) which comprises coupling a compound of formula (XI)

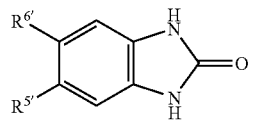

(XI)

with a compound of formula (XII)

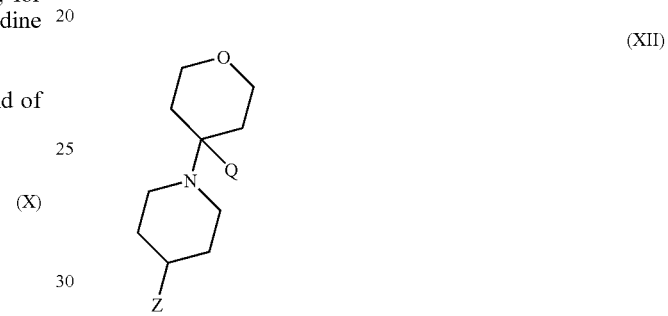

(XII)

wherein R⁵' is a group R⁵ as defined in claim 1, or a group convertible to R⁵ and R⁶' is a group R⁶ as defined in claim 1, or a group convertible to R⁶, Q is hydrogen or $C_{1-6}$alkyl and Z is hydroxy or a leaving group under alkylation or Mitsunobu reaction conditions and optionally thereafter, for any of the above processes:
  removing any protecting groups; and/or
  converting a compound of formula (I) or a salt thereof to another compound of formula (I) or a salt thereof.

* * * * *